(12) United States Patent
Schuch et al.

(10) Patent No.: US 11,524,046 B2
(45) Date of Patent: Dec. 13, 2022

(54) BIOFILM PREVENTION, DISRUPTION AND TREATMENT WITH BACTERIOPHAGE LYSIN

(71) Applicant: ContraFect Corporation, Yonkers, NY (US)

(72) Inventors: Raymond Schuch, Mountain Lakes, NJ (US); Robert C. Nowinski, New York, NY (US); Michael Wittekind, Bainbridge Island, WA (US); Babar Khan, Kingston, NY (US); Jimmy Rotolo, New York, NY (US)

(73) Assignee: CONTRAFECT CORPORATION, Yonkers, NY (US)

( * ) Notice: Subject to any disclaimer, the term of this patent is extended or adjusted under 35 U.S.C. 154(b) by 46 days.

(21) Appl. No.: 16/391,272

(22) Filed: Apr. 22, 2019

(65) Prior Publication Data
US 2019/0387745 A1 Dec. 26, 2019

Related U.S. Application Data

(63) Continuation of application No. 15/293,586, filed on Oct. 14, 2016, now abandoned, which is a continuation of application No. 14/399,588, filed as application No. PCT/US2013/040340 on May 9, 2013, now Pat. No. 9,499,594.

(60) Provisional application No. 61/736,813, filed on Dec. 13, 2012, provisional application No. 61/644,799, filed on May 9, 2012.

(51) Int. Cl.
| | | |
|---|---|---|
| *A61K 38/16* | (2006.01) | |
| *C12N 9/50* | (2006.01) | |
| *A01N 63/50* | (2020.01) | |
| *A61L 29/08* | (2006.01) | |
| *A61L 29/16* | (2006.01) | |
| *C07K 14/315* | (2006.01) | |
| *A61K 38/47* | (2006.01) | |
| *A61K 45/06* | (2006.01) | |

(52) U.S. Cl.
CPC .............. *A61K 38/16* (2013.01); *A01N 63/50* (2020.01); *A61K 38/164* (2013.01); *A61K 38/47* (2013.01); *A61K 45/06* (2013.01); *A61L 29/08* (2013.01); *A61L 29/16* (2013.01); *C07K 14/315* (2013.01); *C12N 9/503* (2013.01); *C12Y 302/01017* (2013.01); *A61L 2300/404* (2013.01); *A61L 2300/406* (2013.01); *A61L 2420/00* (2013.01)

(58) Field of Classification Search
CPC ........... A61L 2300/404; A61L 2420/00; A61L 29/16; A61L 29/08; A61L 2300/406; A61K 38/164; A61K 38/47; A61K 45/06; A61K 38/16; C07K 14/315; A01N 63/50; A01N 63/40; C12Y 302/01017; C12N 9/503
See application file for complete search history.

(56) References Cited

U.S. PATENT DOCUMENTS

| | | | |
|---|---|---|---|
| 5,604,109 A | 2/1997 | Fischetti et al. | |
| 5,985,271 A | 11/1999 | Fischetti et al. | |
| 6,017,528 A | 1/2000 | Fischetti et al. | |
| 6,056,955 A | 5/2000 | Fischetti et al. | |
| 6,248,324 B1 | 6/2001 | Fischetti et al. | |
| 6,254,866 B1 | 7/2001 | Fischetti et al. | |
| 6,264,945 B1 | 7/2001 | Fischetti et al. | |
| 7,402,309 B2 | 7/2008 | Fischetti et al. | |
| 7,569,223 B2 | 8/2009 | Fischetti et al. | |
| 7,582,291 B2 | 9/2009 | Yoong et al. | |
| 7,638,600 B2 | 12/2009 | Fischetti et al. | |
| 2004/0213765 A1 | 10/2004 | Fischetti et al. | |
| 2006/0292135 A1 | 12/2006 | Loomis et al. | |
| 2008/0019956 A1 | 1/2008 | Kumar | |
| 2008/0221035 A1 | 9/2008 | Fischetti et al. | |
| 2010/0172918 A1 | 7/2010 | Yoon et al. | |
| 2012/0034456 A1 | 2/2012 | Hasegawa et al. | |
| 2013/0302306 A1 | 11/2013 | Schuch et al. | |
| 2014/0072549 A1 | 3/2014 | Fischetti et al. | |
| 2019/0290672 A1* | 9/2019 | Wittekind | A61K 38/12 |

FOREIGN PATENT DOCUMENTS

| | | |
|---|---|---|
| CN | 104073478 A | 10/2014 |
| CN | 104726439 A | 6/2015 |
| CN | 104805066 A | 7/2015 |
| EP | 2338916 A1 | 6/2011 |
| JP | 2010536354 A | 12/2010 |
| RU | 2009106069 A | 8/2010 |
| WO | 2008018854 A2 | 2/2008 |
| WO | 2009024327 A2 | 2/2009 |
| WO | 2009108406 A2 | 9/2009 |

(Continued)

OTHER PUBLICATIONS

Drumm et al, Genetic Variation and Clinical Heterogeneity in Cystic Fibrosis, Annu. Rev. Pathol. Mech. Dis., 2012, 7, pp. 267-282.*
Collaboration for Novel Anti-Staph Biologic, from https://fujifilmdiosynth.com/about-us/press-releases/collaboration-novel-anti-staph-biologic/, 2011, pp. 1-2.*
Korean Office Action issued in Korean Patent Application No. 10-2020-7005447 dated Sep. 5, 2020 with English language translation (7 pages).

(Continued)

*Primary Examiner* — Li N Komatsu
(74) *Attorney, Agent, or Firm* — MH2 Technology Law Group LLP

(57) ABSTRACT

The present invention provides methods for the prevention, control, disruption and treatment of bacterial biofilms with lysin, particularly lysin having capability to kill Staphlococcal bacteria, including drug resistant *Staphylococcus aureus*, particularly the lysin PlySs2. The invention also provides compositions and methods for use in treatment or modulation of bacterial biofilm(s) and biofilm formation.

43 Claims, 21 Drawing Sheets
Specification includes a Sequence Listing.

(56) References Cited

FOREIGN PATENT DOCUMENTS

| WO | 2010002959 A2 | 1/2010 |
|---|---|---|
| WO | 2010041970 A2 | 4/2010 |
| WO | 2011518543 A | 6/2011 |
| WO | 2011091412 A1 | 7/2011 |
| WO | 2011134998 A1 | 11/2011 |
| WO | 2011157448 A1 | 12/2011 |
| WO | 2012145573 A2 | 10/2012 |
| WO | 2012145630 A2 | 10/2012 |
| WO | 2012146738 A1 | 11/2012 |

OTHER PUBLICATIONS

Japanese Office Action issued in Japanese Patent Application No. 2018-031017 dated Oct. 27, 2020 with English language translation (8 pages).
Canadian Office Action issued in co-pending Canadian Patent Application No. 2872911 dated Feb. 5, 2019, pp. 1-6.
European Search Report in co-pending European Patent Application No. 13787555.5 dated Feb. 1, 2016, pp. 1-6.
Office Action in co-pending European Patent Application No. 13787555.5 dated Nov. 29, 2017, pp. 1-4.
Office Action in co-pending Korean Patent Application No. 110-2014-7034615 dated May 20, 2019, pp. 1-10 (including English language translation).
Office Action in co-pending Mexican Application No. MX/a/2014/013587 dated May 8, 2018, pp. 1-11 (including English language translation).
Office Action in co-pending Mexican Application No. MX/a/2014/013587 dated Aug. 17, 2017, pp. 1-7 (including English language translation).
Chinese Office Action issued in co-pending Chinese Patent Application No. 201380036474.5 dated Apr. 16, 2019, pp. 1-8 (including English language translation).
Russian Office Action issued in corresponding Russian Patent Application No. 2018102796 dated Oct. 17, 2018, pp. 1-14 (including English language translation).
Australian Office Action issued in corresponding Australian Patent Application No. 2018201736 dated Apr. 1, 2019, pp. 1-5.
European Office Action and search report issued in corresponding European Patent Application No. 19156777 dated Apr. 24, 2019, pp. 1-9.
Dong Q. et al. "Construction of a Chimeric Lysin Ply187N-V12C with Extended Lytic Activity against Staphylococci and Streptococci" Microbial Biotechnology 8.2 (2015): 210-220.
Huang, Y. et al., Molecular dissection of phage lysin PlySs2: integrity of the catalytic and cell wall binding domains is essential for its broad lytic activity, 2015, Virologica Sinica, 30(1): 45-51.
Rudinger, Peptide Hormones, J.A. Parsens, Ed. 1976, pp. 1-7.
Machine translation of CN 104073478 A, pp. 1-15, accessed Sep. 7, 2017.
Machine translation of CN 104726439 A, pp. 1-19, accessed Sep. 7, 2017.
Ben-David et al., Are there differences in hospital cost between patients with nosocomial methicillin-resistant *Staphylococcus aureus* bloodstream infection and those with methicillin-susceptible *S. aureus* bloodstream infection?, Infection Control and Hospital Epidemiology, 2009, 30:453-460.
Caldentey et al., The lytic enzyme of the Pseudomonas phage 06, purification and biochemical characterization, 1992, Biochimica et Biophysica Acta, 1159:44-50.
Costerton et al., Biofilms, the customized microniche, 1994, Journal of Bacteriology, 176:2137-2142.
Matias et al., Cryo-electron microscopy of cell division in *Staphylococcus aureus* reveals a mid-zone between nascent cross walls, Molecular Microbiology, 2007, 64:195-206.
Pettersen et al., UCSF chimera—a visualization system for exploratory research and analysis, J. Comput. Chem., 2004, 25:1605-1612.

Recsei et al., Cloning, sequence, and expression of the lysostaphin gene from *Staphylococcus simulans*, Proc. Natl. Acad. Sci. USA, 1987, 84:1127-1131.
Rossi et al., Structural Elucidation of the Cys-His-Glu-Asn proteolytic relay in the secreted CHAP domain enzyme from the human pathogen *Staphylococcus saprophyticus*, Proteins, 2009, 74:515-519.
Vasilev et al., Antibacterial surfaces for biomedical devices, 2009, Expert Rev. Med. Devices, 6:553-567.
Yang et al., Pattern differentiation in co-culture biofilms formed by *Staphylococcus aureus* and Pseudomonas aeruginosa, FEMS Immunol. Med. Microbiol., 2011, 62:339-347.
Zhang, Y., "I-TASSER server for protein 3D structure prediction", 2008, BMC Bioinformatics, 9:40, pp. 1-8.
Office Action in co-pending Japanese Patent Application No. 2015-511701 dated Oct. 23, 2017, pp. 1-11 (including English language translation).
Office Action in co-pending Indian Patent Application No. 2438/MUMNP/2014 dated Jul. 30, 2018, pp. 1-6.
Notice from Israel Patent Office in co-pending Israeli Patent Application No. 235526 dated Aug. 18, 2019, pp. 1-2 (including partial English language translation), Only English part.
Notice of Allowance from Israel Patent Office in co-pending Israeli Patent Application No. 235526 dated May 29, 2019, pp. 1-3 (including partial English language translation), Only English part.
Office Action in co-pending Israel Patent Application No. 235526 dated Aug. 16, 2018, pp. 1-3 (including partial English language translation), Only English part.
Office Action in co-pending Israel Patent Application No. 235526 dated Jan. 13, 2019, pp. 1-5 (including partial English language translation), Only English part.
Office Action in co-pending Chinese Patent Application No. 201380036474.5 dated Jan. 9, 2020, pp. 1-10 (including English language translation).
Office Action in co-pending Mexican Application No. MX/a/2014/013587 dated Dec. 13, 2018, pp. 1-4 (English language translation).
Extended European Search Report issued in co-pending European Application No. 13787555.5 dated Feb. 1, 2016, pp. 1-6.
New Zealand Office Action issued in corresponding New Zealand Patent Application No. 702067 dated Aug. 1, 2016, pp. 1-5.
New Zealand Office Action issued in corresponding New Zealand Patent Application No. 702067 dated Dec. 9, 2015, pp. 1-5.
Office Action in co-pending Mexican Application No. MX/a/2014/013587 dated Feb. 14, 2019, pp. 1-6 (including English language translation).
Galvez-Castillo, O. (Coordinator), Office Action in co-pending Mexican Application No. MX/a/2014/013587 dated May 28, 2015, (including English language translation), pp. 1-5.
Galvez-Castillo, O. (Coordinator), Office Action in co-pending Mexican Application No. MX/a/2014/013587 dated Nov. 26, 2014, pp. 1-4 (including English language translation).
Chinese Office Action issued in co-pending Chinese Patent Application No. 201380036474.5 dated Jan. 9, 2020, pp. 1-10 (including English language translation).
Australian Office Action issued in corresponding Australian Patent Application No. 2013259427 dated Feb. 3, 2017, pp. 1-5.
Canadian Office Action issued in co-pending Canadian Patent Application No. 2872911 dated Feb. 6, 2020, pp. 1-4.
Weisser, Dagmar, European Office Action issued in European Patent Application No. EP 19156777.5 dated Nov. 11, 2020 (3 pages).
Ako Fukakusa, Japanese Office Action issued in corresponding Japanese Application No. 2018-031017 dated Apr. 7, 2020, 4 pages.
Ako Fukakusa, Japanese Office Action issued in corresponding Japanese Application No. 2018-031017 dated Apr. 7, 2020, 6 pages.
Gilmer D.B. et al., Abstracts of the General Meeting of the American Society for Microbiology, 2011, vol. 111, Presentation No. 1514.
Israel Office Action issued in corresponding Israel Application No. 235526 dated Mar. 1, 2020, 5 pages.(including partial English language translation).
S. A. Ilchenko, Russian Office Action issued in corresponding Russian Application No. 2018102796 dated Jan. 13, 2020, 10 pages.

(56) References Cited

OTHER PUBLICATIONS

O'Flaherty et al., 2009, Bacteriophage and their lysins for elimination of infectious bacteria, FEMS Microbiol Rev, 33:801-819.
Kiedrowski, MR et al., 2011, New approaches for treating Staphylococcal biofilm infections Ann N Y Acad Sci 1241:104-121.
Designing Custom Peptides, SIGMA, retrieved from http://www.sigma-genosys.com/peptide_design.asp, Dec. 16, 2004, pp. 1-2.
Berendsen, A Glimpse of the Holy Grail, 1988, Science, 282: 642-643.
Voet et al., Biochemistry: Second Edition, John Wiley & Sons Inc. publishing, (1995) pp. 235-241.
Ngo et al., Computational Complexity: Protein Structure Protection, and the Levinthal Paradox, The Protein Folding Problem and Tertiary Structure Prediction, (1994) pp. 491-494.
Bradley et al., Limits of Cooperativity in a Structurally Modular Protein: Response of the Notch Ankyrin Domain to Analogous Alanine Substitutions in Each Repeat, J. Mol. Biol., 2002, 324: 373-386.
Gram-positive bacteria, pp. 1-17, accessed Dec. 30, 2015.
Curtin et al., Using Bacteriophages to Reduce Formation of Catheter-Associated Biofilms by *Staphylococcus epidermidis*, Antimicrobial Agents and Chemotherapy, 2006, 50:1268-1275.
Streit et al., Daptomycin tested against 915 bloodstream isolates of viridans group Streptococci (eight species) and *Streptococcus bovis*, Journal of Antimicrobial Chemotherapy, 2005, 55: 574-578.
Raad et al., Comparative Activities of Daptomycin, Linezolid, and Tigecycline against Catheter-Related Methicillin-Resistant *Staphylococcus bacteremic* Isolates Embedded in Biofilm, Antimicrobial Agents and Chemotherapy, 2007, 51:1656-1660.
Saginur et al., Multiple Combination Bactericidal Testing of Staphylococcal Biofilms from Implant-Associated Infections, Antimicrobial Agents and Chemotherapy, 2006, 50: 55-61.
Abad, CL et al., Antimicrobial therapy of sepsis and septic shock—when are two drugs better than one Critical Care Clinics, 2011, 27(2):e1-27.
Ahmed, AB et al., Evaluation of cell wall binding domain of *Staphylococcus aureus* autolysin as affinity reagent for bacteria and its application to bacterial detection, 2007, J. Biosci. Bioeng. 104(1):55-61.
Bateman, A et al., The CHAP domain: a large family of amidases including GSP amidase and peptidoglycan hydrolases Trends Biochem. Sci., 2011, 28(5):234-237.
Beres, SB et al., Contribution of exogenous genetic elements to the group A *Streptococcus metagenome* PLoS One, 2007, 2(8):e800 1-14.
Berti, AD et al., Altering the proclivity towards daptomycin resistance in methicillin-resistant *Staphylococcus aureus* using combinations with other antibiotics, 2012, Antimicrob. Agents Chemother., 56(10):5046-5053.
Blaser, M., Antibiotic overuse: Stop the killing of beneficial bacteria, 2011, Nature, 476(7361):393-394.
Brink, A.J., Does resistance in severe infections caused by methicillin-resistant *Staphylococcus aureus* give you the 'creeps', 2012, Curr. Opin. Cult. Care., 18(5):451-459.
Costerton, et al., Bacterial Biofilms: A Common Cause of Persistent Infections Science, 1999, 284(5418):1318-1322.
Cottarel et al., Combination drugs, an emerging option for antibacterial therapy, 2007, Trends Biotechnol., 25(12):547-555.
Crandon et al, Comparative efficacies of human simulated exposures of telavancin and vancomycin against methicillin-resistant *Staphylococcus aureus* with a range of vancomycin MICs in a murine pneumonia model, 2010, Antimicrob. Agents Chemother., 54(12):5115-5119.
Daniel et al., Synergism between a novel chimeric lysin and oxacillin protects against infection by methicillin-resistant *Staphylococcus aureus*, 2010, Antimicrob. Agents Chemother., 54(4):1603-1612.
Darouiche, R.O., Treatment of infections associated with surgical implants, 2004, N. Engl. J. Med., 350(14):1422-1429.

Dhand, A et al., Use of antistaphylococcal beta-lactams to increase daptomycin activity in eradicating persistent bacteremia due to methicillin-resistant *Staphylococcus aureus*: role of enhanced daptomycin binding, 2011, Clin. Infect. Dis., 53(2):158-163.
Document M07-A9; Methods for dilution antimicrobial susceptibility tests for bacteria that grow aerobically vol. 32 (Wayne (PA): Clinical and Laboratory Standards Institute (US) (2012).
Domenech, et al., In vitro destruction of *Streptococcus pneumoniae* biofilms with bacterial and phage peptidoglycan hydrolases, 2011, Antimicrob. Agents Chemother., 55(9):4144-4148.
Donlan et al., Biofilms: Survival Mechanisms of Clinically Relevant Microorganisms, 2002, Clin. Microbiol. Rev., 15(2):167-193.
Dror, N et al., Advances in microbial biofilm prevention on indwelling medical devices with emphasis on usage of acoustic energy, Sensors (Basel), 2009, 9(4):2538-2554.
Entenza et al., Role of sigmaB in the expression of *Staphylococcus aureus* cell wall adhesins ClfA and FnbA and contribution to infectivity in a rat model of experimental endocarditis, 2005, Infect. Immun., 73(2):990-998.
Entenza et al., Therapeutic effects of bacteriophage Cpl-1 lysin against *Streptococcus pneumoniae* endocarditis in rats, 2005, Antimicrob. Agents Chemother., 49(11):4789-4792.
Fenton et al., Recombinant bacteriophage lysins as antibacterials, 2010, Bioeng. Bugs, 1(1):9-16.
Fischbach, M.A., Combination therapies for combating antimicrobial resistance Current Opinion in Microbiology, 2011, 14(5):519-523.
Fischetti et al., Reinventing phage therapy: are the parts greater than the sum, 2006, Nat. Biotechnol., 24(12):1508-1511.
Fischetti, V.A., Bacteriophage lysins as effective antibacterials, 2008, Curr. Opin. Microbiol. 11(5):393-400.
Flemming et al., The EPS matrix: the "house of biofilm cells", 2007, J. Bacteriol., 189(22):7945-7947.
Friedman et al., Genetic changes that correlate with reduced susceptibility to daptomycin in *Staphylococcus aureus*, 2006, Antimicrob. Agents Chemother., 50(6):2137-2145.
Garcia et al., Molecular evolution of lytic enzymes of *Streptococcus pneumoniae* and its bacteriophages, 1988, Proc. Natl. Acad. Sci. USA, 85(3):914-918.
Garcia et al., Modular organization of the lytic enzymes of *Streptococcus pneumoniae* and its bacteriophages, 1990, Gene 86(1):81-88.
Gilmer et al., Novel Bacteriophage Lysin with Broad Lytic Activity Protects against Mixed Infection by Methicillin-Resistant *Staphylococcus aureus* and *Streptococcus pyogenes*, 2013, Antimicrob. Agents Chemother., 57(6):2743-2750, Epub Apr. 9, 2013.
Klevens et al., Invasive Methicillin-Resistant *Staphylococcus aureus* Infections in the United States, 2007, JAMA, 298(15):1763-1771.
Grandgirard et al., Phage lytic enzyme Cpl-1 for antibacterial therapy in experimental pneumococcal meningitis, 2008, J. Infect. Dis., 197(11):1519-1522.
Hazan et al., Effective prevention of microbial biofilm formation on medical devices by low-energy surface acoustic waves, 2006, Antimicrob. Agents Chemother., 50(12):4144-4152.
Jansen et al., Prevention of biofilm formation by polymer modification, 1995, J. Ind. Microbiol., 15(4):391-396.
Jobson et al., Retrospective observational study comparing vancomycin versus daptomycin as initial therapy for *Staphylococcus aureus* infections, 2011, Clin Ther., 33(10):1391-1399.
Johansen et al., Enzymatic removal and disinfection of bacterial biofilms, 1997, Appl. Environ. Microbiol., 63(9):3724-3728.
Kashyap et al., Peptidoglycan recognition proteins kill bacteria by activating protein-sensing two-component systems, 2011, Nat. Med., 17(6):676-683.
Kokai-Kun et al., Lysostaphin as a treatment for systemic *Staphylococcus aureus* infection in a mouse model, 2007, J. Antimicrob. Chemother., 60(5):1051-1059.
LaPlante et al., Activities of clindamycin, daptomycin, doxycycline, linezolid, trimethoprim-sulfamethoxazole, and vancomycin against community-associated methicillin-resistant *Staphylococcus aureus* with inducible clindamycin resistance in murine thigh infection and in vitro pharmacodynamic models, 2008, Antimicrob. Agents Chemother., 52(6):2156-2162.

(56) References Cited

OTHER PUBLICATIONS

Russian Office Action issued in corresponding Russian Patent Application No. 2018102796 dated Mar. 14, 2019, pp. 1-11 (including English language translation).
Japanese Office Action issued in corresponding Japanese Patent Application No. 2018-031017 dated Nov. 5, 2019, pp. 1-10 (including English language translation).
Australian Office Action issued in corresponding Australian Patent Application No. 2018201736 dated Oct. 22, 2019, pp. 1-4.
Schmitz, J., Expanding The Horizons Of Enzybiotic Identification, Graduate School Student Theses, The Rockefeller University, Jun. 2011, [Retrieved from internet on Jan. 19, 2017] URL: http://hdl.handle.net/10209/448.
Meng, X et al., Application of a bacteriophage lysin to disrupt biofilms formed by the animal pathogen *Streptococcus suis*, 2011, Appl. Environ. Microbiol., 77:8272-8279.
Russian Search Report issued in 201810276 dated Oct. 16, 2018, pp. 1-4, (including English language translation).
Loeffler et al., Rapid killing of *Streptococcus pneumoniae* with a bacteriophage cell wall hydrolase, Science, 2001, 294(5549):2170-2172.
Loeffler et al., Phage Lytic Enzyme Cpl-1 as a Novel Antimicrobial for Pneumococcal Bacteremia Infect. Immun., 2003, 71(11):6199-6204.
Loessner et al., Heterogeneous endolysins in Listeria monocytogenes bacteriophages: a new class of enzymes and evidence for conserved holin genes within the siphoviral lysis cassettes, 1995, Mol. Microbiol., 16(6):1231-1241.
Loessner, M.J., Bacteriophage endolysins—current state of research and applications, 2005, Curr. Opin. Microb., 8(4):480-487.
Lopez et al., Structural analysis and biological significance of the cell wall lytic enzymes of *Streptococcus pneumoniae* and its bacteriophage, 1992, FEMS Microbiol. Lett., 100(1-3):439-447.
Lopez et al.,1997, The pneumococcal cell wall degrading enzymes: a modular design to create new lysins, Microb. Drug Resist., 3(2):199-211.
Maki et al., Engineering out the risk for infection with urinary catheters, 2001, Emerg. Infect. Dis., 7(2):342-347.
Manoharadas et al., 2009, Antimicrobial activity of a chimeric enzybiotic towards *Staphylococcus aureus*, J. Biotechnol., 139(1):118-123.
McCullers et al., Novel Strategy to Prevent Otitis Media Caused by Colonizing *Streptococcus pneumoniae*, 2007, PLoS Pathog, 3(3):0001-0003.
Moise et al., Susceptibility relationship between vancomycin and daptomycin in *Staphylococcus aureus*: facts and assumptions, 2009, Lancet Infect. Dis., 9(10):617-624.
Mueller et al., 2004, Issues in Pharmacokinetics and Pharmacodynamics of Anti-Infective Agents: Kill Curves versus MIC, Antimicrob. Agents Chemother., 48(2):369-377.
Nelson et al. Prevention and elimination of upper respiratory colonization of mice by group A Streptococci by using a bacteriophage lytic enzyme, 2001, Proc. Natl. Acad. Sci. USA, 98(7):4107-4112.
Pastagia et al., A novel chimeric lysin shows superiority to mupirocin for skin decolonization of methicillin-resistant and-sensitive *Staphylococcus aureus* strains, 2011, Antimicrob. Agents Chemother., 55(2):738-744.
Pereira et al., Fluorescence ratio imaging microscopy shows decreased access of vancomycin to cell wall synthetic sites in vancomycin-resistant *Staphylococcus aureus*, 2007, Antimicrob. Agents Chemother., 51(10):3627-3633.
Rashel et al., Efficient elimination of multidrug-resistant *Staphylococcus aureus* by cloned lysin derived from bacteriophage phi MR11, 2007, J. Infect. Dis., 196(8):1237-1247.
Romero et al., Sequence of the *Streptococcus pneumoniae* bacteriophage HB-3 amidase reveals high homology with the major host autolysin, 1990, J. Bacteriol.,172(9):5064-5070.

Ronda et al., Biological role of the pneumococcal amidase: Cloning of the lytA gene in *Streptococcus pneumoniae*, 1987, Eur. J. Biochem., 164(3):621-624.
Sanchez-Puelles et al., 3-end modifications of the *Streptococcus pneumoniae* lytA gene: role of the carboxy terminus of the pneumococcal autolysin in the process of enzymatic activation (conversion), 1987, Gene, 61(1):13-19.
Sass et al., Lytic activity of recombinant bacteriophage phi11 and phi12 endolysins on whole cells and biofilms of *Staphylococcus aureus*, 2007, Appl. Environ. Microbiol., 73(1):347-352.
Schuch et al., A bacteriolytic agent that detects and kills Bacillus anthracis, 2002, Nature, 418(6900):884-889.
Schuch et al., A Genetic Screen to Identify Bacteriophage Lysins Methods, 2009, Mol. Biol., 502:307-319.
Schweizer et al., Comparative effectiveness of nafcillin or cefazolin versus vancomycin in methicillin-susceptible *Staphylococcus aureus* bacteremia, 2011, BMC Infect. Dis., 11:279.
Son et al., Antibacterial and biofilm removal activity of a podoviridae *Staphylococcus aureus* bacteriophage SAP-2 and a derived recombinant cell-wall-degrading enzyme, 2010, Appl. Microbiol. Biotechnol., 86(5):1439-1449.
Sopirala et al., Synergy testing by Etest, microdilution checkerboard, and time-kill methods for pan-drug-resistant Acinetobacter baumannii, 2010, Antimicrob. Agents Chemother., 54(11):4678-4683.
Tallarida, R.J., Revisiting the isobole and related quantitative methods for assessing drug synergism, 2012, J. Pharmacol. Exp. Ther., 342(1):2-8.
Wang et al., Holins: the protein clocks of bacteriophage infections, 2000, Annu. Rev. Microbiol., 54:799-825.
Weigel et al., High-level vancomycin-resistant *Staphylococcus aureus* isolates associated with a polymicrobial biofilm, 2007, Antimicrob. Agents Chemother., 51(1):231-238.
Whisstock et al., SH3 domains in prokaryotes, 1999, Trends Biochem. Sci., 24(4):132-133.
Willing et al., Shifting the balance: antibiotic effects on host-microbiota mutualis, 2011, Nat. Rev. Microbiol., 9(4):23.
Witzenrath et al., Systemic use of the endolysin Cpl-1 rescues mice with fatal pneumococcal pneumonia, 2009, Critical Care Medicine, 37(2):642-649.
Wu et al., Lysostaphin disrupts *Staphylococcus aureus* and *Staphylococcus epidermidis* biofilms on artificial surfaces, 2003, Antimicrob. Agents Chemother., 47(11):3407-3414.
Yang et al., Current understanding of multi-species biofilms, 2011, Int. J. Oral Sci., 3(2):74-81.
Zhu et al., *Staphylococcus aureus* biofilm metabolism and the influence of arginine on polysaccharide intercellular adhesin synthesis, biofilm formation, and pathogenesis, 2007, Infect. Immunol., 75(9):4219-4226.
Fischetti V.A., Bacteriophage endolysins: a novel anti-infective to control Gram-positive pathogens, 2010, Int. J. Med. Microbiol., 300(6):357-362.
Lucas et al., Uniprot:B9WWF8, 2009, XP055150805.
Low et al., Role of net charge on catalytic domain and influence of cell wall binding domain on bactericidal activity, specificity, and host range of phage lysins, 2011, Biol. Chem., 286(39): 34391-403.
Machine translation of CN 104805066 A, pp. 1-11, accessed Sep. 7, 2017.
Yampolsky et al., The Exchangeability of Amino Acids in Proteins, 2005, Genetics, 170:1459-1472.
International Search Report issued in PCT/US2013/40340 dated Sep. 30, 2013, pp. 1-3.
Office Action issued in Brazilian Patent Application No. 112014027818 dated Jun. 23, 2020 with English language translation (5 pages).
Donlan, R.M., Biofilms and device-associated infections, 2001, Emerg. Infect. Dis., 7(2):277-281.
Frankel et al., Characterization of diphtheria fusion proteins targeted to the human interleukin-3 receptor, 2000, Protein Eng., 13:575-581.
Office Action in co-pending Japanese Patent Application No. 2015-511701 dated Feb. 3, 2017, pp. 1-8 (including English language translation).

(56) References Cited

OTHER PUBLICATIONS

Galvez-Castillo, O. (Coordinator), Office Action in co-pending Mexican Application No. MX/a/2014/013587 dated May 28, 2015, pp. 1-3 (including English language translation).
Haiwei et al., Protein Tolerance to Random Amino Acid Change, 2004, PNAS, 101: 9205-9210.
Loessner et al., Modified Listeria Bacteriophage Lysin Genes (ply) allow efficient overexpression and one-step purification of biochemically active fusion proteins, 1996, Applied and Environmental Microbiology, 62:3057-3060.
Notice from Israel Patent Office in co-pending Israeli Patent Application No. 235526 dated Aug. 18, 2019, pp. 1-2 (including partial English language translation).
Notice of Allowance from Israel Patent Office in co-pending Israeli Patent Application No. 235526 dated May 29, 2019, 4 pages (including partial English language translation).
Office Action in co-pending Israel Patent Application No. 235526 dated Aug. 16, 2018, 4 Pages (including partial English language translation).
Office Action in co-pending Israel Patent Application No. 235526 dated Jan. 13, 2019, 4 pages (including partial English language translation).
Pakula et al., Genetic Analysis of Protein Stability and Function, 1989, Ann. Rev. Genet., 23:289-310.
Office Action in co-pending Korean Patent Application No. 10-2020-7005447 ddated Mar. 25, 2021, 9 pages (including English language translation).
Communication pursuant to Article 94(3) EPC in co-pending European Patent Application No. 19156777.5 dated Apr. 19, 2021, 4 pages.
Communication pursuant to Article 94(3) EPC in co-pending European Patent Application No. 19156777.5 dated Dec. 22, 2022, 3 pages.
Office Action in co-pending Israel Patent Application No. 235526 dated Feb. 21, 2022, 4 Pages (including partial English anguage translation), only the Sections in English.
Office Action issued in Canadian Patent Application No. 2,872,911 dated Aug. 10, 2021, 4 pages.
Notice of Final Rejection issued in Korean Patent Application No. 10-2020-7005447 dated Jul. 22, 2021, 9 pages.
Office Action issued in Japanese Patent Application No. 2020-134278 dated Aug. 17, 2021, 6 pages.

\* cited by examiner

MTTVNEALNN VRAQVGSGVS VGNGECYALA SWYERMISPD ATVGLGAGVG SAKNIGSSYN
WQANGWTVST SGPFKAGQIV TLGATPGNPY GHVVIVEAVD GDRLTILEQN YGGKRYPVRN YYSAASYRQQ
VVHYITPPGT VAQSAPNLAG SRSYRETGTM TVTVDALNVR RAPNTSGEIV AVYKRGESFD YDTVIIDVNG
YVWVSYIGGS GKRNYVATGA TKDGKRFGNA WGTFK

CHAP Domain in    LNNVR...VVHYIT
SH3-5 Domain in   RSYRE...GKRNYVAT

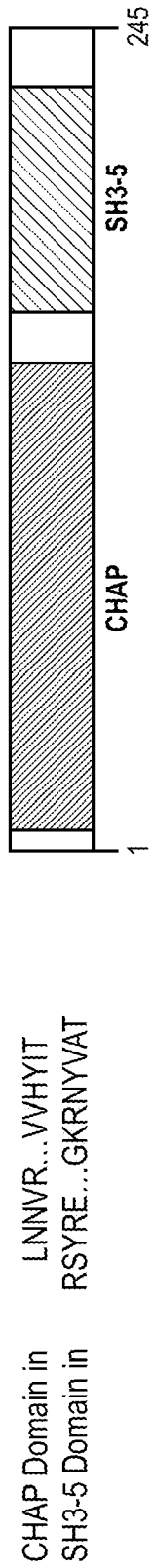

ATGACAACAG TAAATGAAGC ATTAAATAAT GTAAGAGCTC AGGTTGGGTC CGGTGTGTCT GTTGGCAACG
GCGAATGCTA CGCTTTGGCT AGTTGGTACG AGCGCATGAT TAGTCCGGAT GCAACTGTCG GACTTGGCGC
TGGTGTGGGG TGGGTCAGCG GTGCAATACG CGATACAATC TCTGCCAAAA ACATCGGCTC ATCATACAAC
TGGCAAGCTA ACGGCTGGAC AGTTTCCACA AGTTTCCGGT TTAAAGCAGG TCAGATTGTG ACGCTTGGGG
CAACACCAGG AAACCCTTAC GGACATGTGG TAATCGTCGA AGCAGTGGAC GGCGATAGAT TCGTCAACAG
GGAGCAAAAC TACGGCGGGA AACGTTATCC CGTCCGTAAT TATTACAGCG CTGCAAGCTA TCGTCAACAG
GTCGTGCATT ACATCACACC GCCTGGCACG GTCGCACAGT CCTTGCAGGC AGGGCGCCAA CCTCGTTCCT
ATCGCGAGAC GGGCACTATG ACTGTCGATG TCGCAATTGA TATGATACTG AGGGCGCCAA ATACTTCAGG
CGAGATTGTA GCAGTATACA AGCGTGGTGA ATCATTTGAC TATGATACTG TCATCATCGA TGTCAATGGC
TATGTCTGGG TGTCTTACAT AGGCGGCAGC AGGCGGCAGC TGCAAAGGTA ACTACGTTGC GACGGGCGCT ACCAAAGACG
GTAAGCGTTT CGGCAATGCT TGGGGTACAT TTAAATAA

FIG. 5

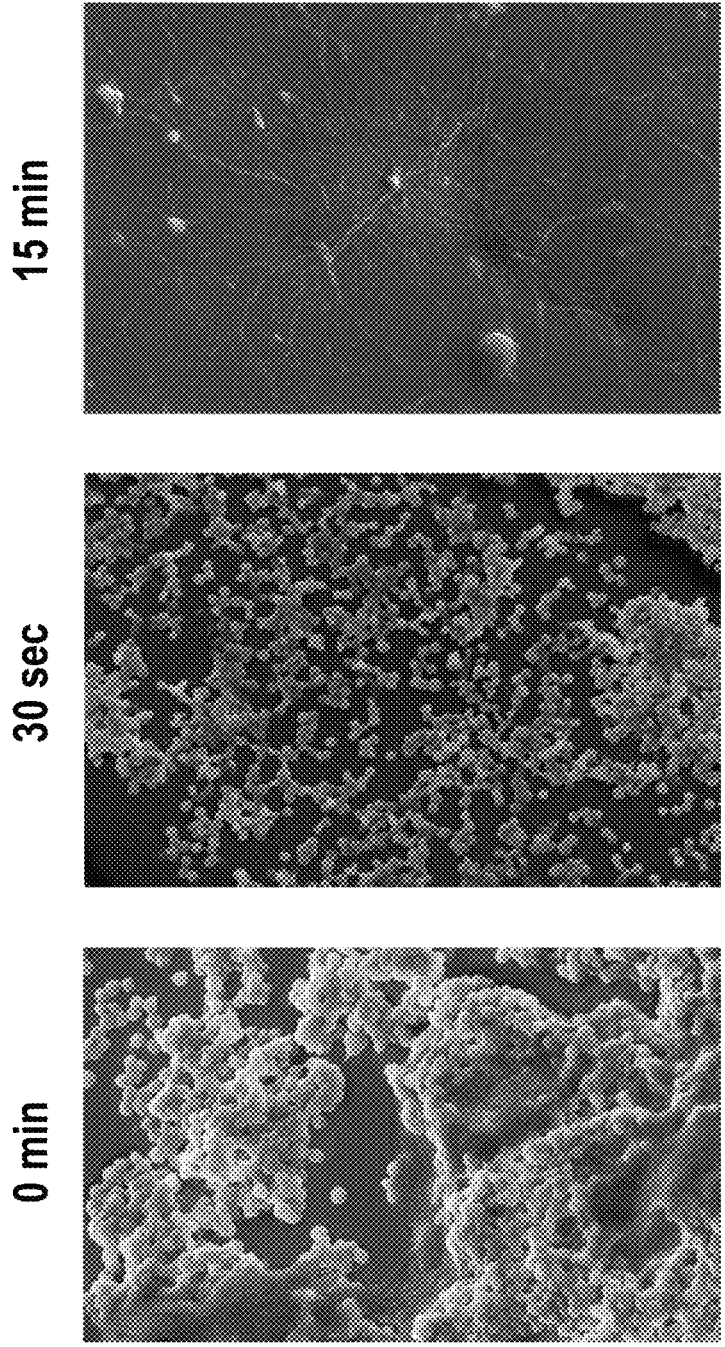

BIOFILM PREVENTION, DISRUPTION AND TREATMENT WITH BACTERIOPHAGE LYSIN

CROSS REFERENCE TO RELATED APPLICATIONS

This application is a Continuation of application Ser. No. 15/293,586, filed on Oct. 14, 2016, which is a Continuation of application Ser. No. 14/399,588, filed Nov. 7, 2014 (now U.S. Pat. No. 9,499,594), which was filed as PCT International Application No. PCT/US2013/040340 on May 9, 2013, which claims the benefit under 35 U.S.C. § 119(e) to U.S. Provisional Application No. 61/736,813, filed on Dec. 13, 2012, and U.S. Provisional Application No. 61/644,799, filed on May 9, 2012, all of which are hereby expressly incorporated by reference into the present application.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "Sequence_listing_as_filed.txt" created on Sep. 6, 2018, and is 7,979 bytes in size. The sequence listing contained in this .txt file is part of the specification and is hereby incorporated by reference herein in its entirety

FIELD OF THE INVENTION

The present invention relates generally to prevention, control, disruption and treatment of bacterial biofilms with lysin, particularly lysin having capability to kill Staphylococcal bacteria, including drug resistant *Staphylococcus aureus*, particularly the lysin PlySs2. The invention also relates to compositions and methods for modulation of bacterial biofilm(s) and biofilm formation.

BACKGROUND OF THE INVENTION

The development of drug resistant bacteria is a major problem in medicine as more antibiotics are used for a wide variety of illnesses and other conditions. The use of more antibiotics and the number of bacteria showing resistance has prompted longer treatment times. Furthermore, broad, non-specific antibiotics, some of which have detrimental effects on the patient, are now being used more frequently. A related problem with this increased use is that many antibiotics do not penetrate mucus linings easily.

Gram-positive bacteria are surrounded by a cell wall containing polypeptides and polysaccharide. Gram-positive bacteria include but are not limited to the genera *Actinomyces, Bacillus, Listeria, Lactococcus, Staphylococcus, Streptococcus, Enterococcus, Mycobacterium, Corynebacterium,* and *Clostridium*. Medically relevant species include *Streptococcus pyogenes, Streptococcus pneumoniae, Staphylococcus aureus,* and *Enterococcus faecalis*. *Bacillus* species, which are spore-forming, cause anthrax and gastroenteritis. Spore-forming *Clostridium* species are responsible for botulism, tetanus, gas gangrene and pseudomembranous colitis. *Corynebacterium* species cause diphtheria, and *Listeria* species cause meningitis.

Novel antimicrobial therapy approaches include enzyme-based antibiotics ("enzybiotics") such as bacteriophage lysins. Phages use these lysins to digest the cell wall of their bacterial hosts, releasing viral progeny through hypotonic lysis. A similar outcome results when purified, recombinant lysins are added externally to Gram-positive bacteria. The high lethal activity of lysins against gram-positive pathogens makes them attractive candidates for development as therapeutics (Fischetti, V. A. (2008) Curr Opinion Microbiol 11:393-400; Nelson, D. L. et al (2001) Proc Natl Acad Sci USA 98:4107-4112). Bacteriophage lysins were initially proposed for eradicating the nasopharyngeal carriage of pathogenic streptococci (Loeffler, J. M. et al (2001) Science 294: 2170-2172; Nelson, D. et al (2001) Proc Natl Acad Sci USA 98:4107-4112). Lysins are part of the lytic mechanism used by double stranded DNA (dsDNA) phage to coordinate host lysis with completion of viral assembly (Wang, I. N. et al (2000) Annu Rev Microbiol 54:799-825). Lysins are peptidoglycan hydrolases that break bonds in the bacterial wall, rapidly hydrolyzing covalent bonds essential for peptidoglycan integrity, causing bacterial lysis and concomitant progeny phage release.

Lysin family members exhibit a modular design in which a catalytic domain is fused to a specificity or binding domain (Lopez, R. et al (1997) Microb Drug Resist 3:199-211). Lysins can be cloned from viral prophage sequences within bacterial genomes and used for treatment (Beres, S. B. et al (2007) PLoS ONE 2(8):1-14). When added externally, lysins are able to access the bonds of a Gram-positive cell wall (Fischetti, V. A. (2008) Curr Opinion Microbiol 11:393-400). Bacteriophage lytic enzymes have been established as useful in the assessment and specific treatment of various types of infection in subjects through various routes of administration. For example, U.S. Pat. No. 5,604,109 (Fischetti et al.) relates to the rapid detection of Group A streptococci in clinical specimens, through the enzymatic digestion by a semi-purified Group C streptococcal phage associated lysin enzyme. This enzyme work became the basis of additional research, leading to methods of treating diseases. Fischetti and Loomis patents (U.S. Pat. Nos. 5,985, 271, 6,017,528 and 6,056,955) disclose the use of a lysin enzyme produced by group C streptococcal bacteria infected with a C1 bacteriophage. U.S. Pat. No. 6,248,324 (Fischetti and Loomis) discloses a composition for dermatological infections by the use of a lytic enzyme in a carrier suitable for topical application to dermal tissues. U.S. Pat. No. 6,254,866 (Fischetti and Loomis) discloses a method for treatment of bacterial infections of the digestive tract which comprises administering a lytic enzyme specific for the infecting bacteria. The carrier for delivering at least one lytic enzyme to the digestive tract is selected from the group consisting of suppository enemas, syrups, or enteric coated pills. U.S. Pat. No. 6,264,945 (Fischetti and Loomis) discloses a method and composition for the treatment of bacterial infections by the parenteral introduction (intramuscularly, subcutaneously, or intravenously) of at least one lytic enzyme produced by a bacteria infected with a bacteriophage specific for that bacteria and an appropriate carrier for delivering the lytic enzyme into a patient.

Phage associated lytic enzymes have been identified and cloned from various bacteriophages, each shown to be effective in killing specific bacterial strains. U.S. Pat. Nos. 7,402,309, 7,638,600 and published PCT Application WO2008/018854 provides distinct phage-associated lytic enzymes useful as antibacterial agents for treatment or reduction of *Bacillus anthracis* infections. U.S. Pat. No. 7,569,223 describes lytic enzymes for *Streptococcus pneumoniae*. Lysin useful for *Enterococcus* (*E. faecalis* and *E. faecium*, including vancomycin resistant strains) are described in U.S. Pat. No. 7,582,291. US 2008/0221035 describes mutant Ply GBS lysins highly effective in killing Group B streptococci. A chimeric lysin denoted ClyS, with activity against Staphylococci bacteria, including *Staphylococcus aureus*, is detailed in WO 2010/002959. ClyS is specific for Staphylococcal bacteria and is inactive against *Streptococcus* and other gram positive bacteria.

Based on their rapid, potent, and specific cell wall-degradation and bactericidal properties, lysins have been suggested as antimicrobial therapeutics to combat Gram-positive pathogens by attacking the exposed peptidoglycan cell walls from outside the cell (Fenton, M et al (2010) Bioengineered Bugs 1:9-16; Nelson, D et al (2001) Proc Natl Acad Sci USA 98:4107-4112). Efficacies of various lysins as a single agents have been demonstrated in rodent models of pharyngitis (Nelson, D et al (2001) Proc Natl Acad Sci USA 98:4107-4112), pneumonia (Witzenrath, M et al (2009) Crit Care Med 37:642-649), otitis media (McCullers, J. A. et al (2007) PLOS pathogens 3:0001-0003), abscesses (Pastagia, M et al Antimicrobial agents and chemotherapy 55:738-744) bacteremia (Loeffler, J. M. et al (2003) Infection and Immunity 71:6199-6204), endocarditis (Entenza, J. M. et al (2005) Antimicrobial agents and chemotherapy 49:4789-4792), and meningitis (Grandgirard, D et al (2008) J Infect Dis 197:1519-1522). In addition, lysins are generally specific for their bacterial host species and do not lyse non-target organisms, including human commensal bacteria which may be beneficial to gastrointestinal homeostasis (Blaser, M. (2011) Nature 476:393-394; Willing, B. P. et al (2011) Nature reviews. Microbiology 9:233-243)

Microorganisms tend to form surface-attached biofilm communities as an important survival strategy in different environments. Biofilms consist of microbial cells and a wide range of self-generated extracellular polymeric substances, including polysaccharides, nucleic acids, and proteins (Flemming H C et al (2007) J Bacteriol 189:7945-7947). Biofilms are found in natural and industrial aquatic environments, tissues, and medical materials and devices (Costerton J W et al (1994) J Bacteriol 176:2137-2142). Biofilms can be formed by a single bacterial strain, although most natural biofilms are formed by multiple bacterial species (Yang L et al (2011) Int J Oral Sci 3:74-81). Applications of antibiotics are often ineffective for biofilm populations due to their unique physiology and physical matrix barrier.

Staphylococci often form biofilms, sessile communities encased in an extracellular matrix that adhere to biomedical implants or damaged and healthy tissue. Infections associated with biofilms are difficult to treat, and it is estimated that sessile bacteria in biofilms are 1,000 to 1,500 times more resistant to antibiotics than their planktonic counterparts. This antibiotic resistance of biofilms often leads to the failure of conventional antibiotic therapy and necessitates the removal of infected devices. Lysostaphin has been shown to kill *S. aureus* in biofilms and also disrupted the extracellular matrix of *S. aureus* biofilms in vitro on plastic and glass surfaces (Wu, J A et al (2003) Antimicrob Agents and Chemoth 47(11):3407-3414). This disruption of *S. aureus* biofilms was specific for lysostaphin-sensitive *S. aureus*, and biofilms of lysostaphin-resistant *S. aureus* were not affected. High concentrations of oxacillin (400 ag/ml), vancomycin (800 tag/ml), and clindamycin (800 ag/ml) had no effect on the established *S. aureus* biofilms, even after 24 h. Lysostaphin also disrupted *S. epidermidis* biofilms, however, higher concentrations were required. Application of phage lysins for the removal of staphylococcal biofilms have been reported, with mixed results. Bacteriophage lysin SAL-2 was reported to remove *S. aureus* biofilms (Son J S et al (2010) Appl Microbiol Biotechnol 86(5):1439-1449), while in the case of two similar phage lysins, phi11 and phi12, while phi11 hydrolyzed staphylococcal biofilms, phi12 was inactive (Sass P and Bierbaum G (2007) Appl Environ Microbiol 73(1):347-352). Various combinations of enzymes have been studied for the removal and disinfection of bacterial biofilms in various systems (Johansen C et al (1997) Appl Environ Microbiol 63:3724-3728). This process, however, requires a minimum of two enzymes or agents, one enzyme or agent for removal of the adherent bacteria of the biofilms and a second enzyme or agent with bactericidal activity.

It is evident from the deficiencies and problems associated with current traditional antibacterial agents that there still exists a need in the art for additional specific bacterial agents and therapeutic modalities and also for broader spectrum agents, particularly without risks of acquired resistance, for the effective and efficient treatment, control and prevention of bacterial biofilms. It is notable that to date, no lysin demonstrating lytic activity against multiple distinct species of pathogenic and clinically relevant gram positive bacteria, which is readily manufacturable and stable, and has no or limited risk of resistance, has been shown to be effective on biofilms. Accordingly, there is a commercial need for new antibacterial approaches, especially those that operate via new modalities or provide new means to kill pathogenic bacteria in biofilms.

The citation of references herein shall not be construed as an admission that such is prior art to the present invention.

SUMMARY OF THE INVENTION

In accordance with the present invention, compositions and methods are provided for the prevention, disruption and treatment of bacterial biofilms. In its broadest aspect, the present invention provides use and application of a lysin having broad killing activity against multiple bacteria, particularly Gram-positive bacteria, including particularly *Staphylococcus, Streptococcus*, particularly *Streptococcus pyogenes* (Group A strep) and *Streptococcus agalactiae* (Group B strep) bacterial strains, in the prevention, disruption and treatment of biofilms. The lysin and compositions of the invention are useful and applicable in killing *Enterococcus* and *Listeria* bacterial strains, and in applicable biofilms thereof. The invention provides a method for decolonizing, dispersing and removal of bacterial biofilm utilizing bacteriophage lysin capable of killing bacteria effectively and efficiently in a biofilm. The invention thus contemplates treatment, decolonization, and/or decontamination of bacterial biofilms and the prevention of infections after dispersion of biofilm(s) wherein one or more gram positive bacteria, particularly one or more of *Staphylococcus, Streptococcus, Enterococcus* and *Listeria* bacteria, is suspected or present.

In accordance with the present invention, bacteriophage lysin derived from *Streptococcus suis* bacteria are utilized in the methods and applications of the invention. The lysin polypeptide(s) of use in the present invention, particularly PlySs2 lysin as provided herein and in FIG. 5 (SEQ ID NO: 1), are unique in demonstrating broad killing activity against multiple bacteria, particularly gram-positive bacteria, including *Staphylococcus, Streptococcus, Enterococcus* and *Listeria* bacterial strains. In one such aspect, the PlySs2 lysin is capable of killing *Staphylococcus aureus* strains and bacteria in biofilms, as demonstrated herein. PlySs2 is effective against antibiotic-resistant bacteria, including *Staphylococcus aureus* such as methicillin-resistant *Staphylococcus aureus* (MRSA), vancomycin resistant *Staphylo-*

*coccus aureus* (VRSA), daptomycin-resistant *Staphylococcus aureus* (DRSA) and linezolid-resistant *Staphylococcus aureus* (LRSA). PlySs2 is effective against bacteria with altered antibiotic sensitivity such as vancomycin intermediate-sensitivity *Staphylococcus aureus* (VISA).

In an aspect of the invention, a method is provided of killing gram-positive bacteria in a biofilm comprising the step of contacting the biofilm with a composition comprising an amount of an isolated lysin polypeptide effective to kill gram-positive bacteria in a biofilm, including *S. aureus*, the isolated lysin polypeptide comprising the PlySs2 lysin polypeptide or variants thereof effective to kill gram-positive bacteria. Thus, a method is provided of killing gram-positive bacteria in a biofilm comprising the step of contacting the biofilm with a composition comprising an amount of an isolated lysin polypeptide effective to kill the gram-positive bacteria in the biofilm, the isolated lysin polypeptide comprising the amino acid sequence provided in FIG. 5 or SEQ ID NO: 1 or variants thereof having at least 80% identity, 85% identity, 90% identity, 95% identity or 99% identity to the polypeptide of FIG. 5 or SEQ ID NO: 1 and effective to kill the gram-positive bacteria in the biofilm.

In an aspect of the invention, a method is provided of dispersing gram-positive bacteria in a biofilm so as to decontaminate and to release bacteria then susceptible to antibiotics, comprising the step of contacting the biofilm with a composition comprising an amount of an isolated lysin polypeptide effective to disperse gram-positive bacteria in a biofilm, including *S. aureus*, the isolated lysin polypeptide comprising the PlySs2 lysin polypeptide, including as set out in FIG. 5 or SEQ ID NO: 1 or variants thereof effective to kill gram-positive bacteria.

In an aspect of the above methods, the methods are performed in vitro or ex vivo so as to sterilize or decontaminate a solution, material or device, particularly intended for use by or in a human.

The invention provides a method for reducing a population of gram-positive bacteria in a biofilm comprising the step of contacting the biofilm with a composition comprising an amount of an isolated polypeptide effective to kill or release at least a portion of the gram-positive bacteria in the biofilm, the isolated polypeptide comprising the amino acid sequence of FIG. 5 (SEQ ID NO: 1) or variants thereof having at least 80% identity to the polypeptide of FIG. 5 (SEQ ID NO: 1) and effective to kill the gram-positive bacteria.

The present invention further provides a method for dispersing or treating an antibiotic-resistant *Staphylococcus aureus* infection which involves or includes a biofilm in a human comprising the step of administering to a human with an antibiotic-resistant *Staphylococcus aureus* biofilm infection, an effective amount of a composition comprising an isolated polypeptide comprising the amino acid sequence of FIG. 5 (SEQ ID NO: 1) or variants thereof having at least 80% identity, 85% identity, 90% identity or 95% identity to the polypeptide of FIG. 5 (SEQ ID NO: 1) and effective to disperse the biofilm and kill *Staphylococcus aureus* therein and//or released therefrom, whereby the number of *Staphylococcus aureus* in the human is reduced and the biofilm and attendant infection is controlled.

A method of the invention also includes a method for preventing, dispersing or treating a gram-positive bacterial biofilm comprising one or more of *Staphylococcus* or Streptococcusbacteria in a human comprising the step of administering to a subject having or suspected of having or at risk of a bacterial biofilm, an effective amount of a composition comprising an isolated polypeptide comprising the amino acid sequence of FIG. 5 (SEQ ID NO: 1) or variants thereof having at least 80% identity, 85% identity, 90% identity or 95% identity to the polypeptide of FIG. 5 (SEQ ID NO: 1) and effective to kill the gram-positive bacteria, whereby the number of gram-positive bacteria in the human is reduced and the biofilm contamination or infection is controlled. In an aspect of the method, biofilm comprising or including one or more of an *Enterococcus* or *Listeria* bacteria is effectively prevented, dispersed or treated. In a particular aspect of this method, wherein the subject is exposed to or at risk of one of or one or more of *Staphylococcus* (such as *Staphylococcus aureus*), *Streptococcus* (particularly Group A strep or Group B strep such as *Streptococcus pyogenes* or *Streptococcus agalactiae*, respectively)bacteria. An alternative bacteria such as *Listeria* (such as *L. monocytogenes*) or *Enterococcus* (such as *E. faecalis*) bacteria may also be involved and addressed, prevented, dispersed or treated in accordance with the methods and compositions of the invention. The subject may be a human. The subject may be a human adult, child, infant or fetus.

In any such above method or methods, the susceptible, killed, dispersed or treated biofilm bacteria may be selected from *Staphylococcus aureus, Listeria monocytogenes, Staphylococcus simulans, Streptococcus suis, Staphylococcus epidermidis, Streptococcus equi, Streptococcus equi zoo, Streptococcus agalactiae* (GBS), *Streptococcus pyogenes* (GAS), *Streptococcus sanguinis, Streptococcus gordonii, Streptococcus dysgalactiae*, Group G *Streptococcus*, Group E *Streptococcus, Enterococcus faecalis* and *Streptococcus pneumonia*.

In accordance with any of the methods of the invention, the susceptible bacteria or biofilm bacteria may be an antibiotic resistant bacteria. The bacteria may be antibiotic resistant, including methicillin-resistant *Staphylococcus aureus* (MRSA), vancomycin resistant *Staphylococcus aureus* (VRSA), daptomycin-resistant *Staphylococcus aureus* (DRSA), or linezolid-resistant *Staphylococcus aureus* (LRSA). The bacteria may have altered antibiotic sensitivity, such as for example, vancomycin intermediate-sensitivity *Staphylococcus aureus* (VISA), The susceptible bacteria may be a clinically relevant or pathogenic bacteria, particularly for humans. In an aspect of the method(s), the lysin polypeptide(s) is effective to kill *Staphylococcus, Streptococcus, Enterococcus* and *Listeria* bacterial strains.

It has been shown that coating medical implants with antimicrobials may effectively prevent the initial adherence of staphylococcal biofilms to the implants. Coating biomedical materials with lysin may also prove successful in preventing early adherence of bacteria, including staphylococci, to the implants, thus averting biofilm formation. The present invention thus also provides methods for reducing or preventing biofilm growth on the surface of devices, implants, separation membranes (for example, pervaporation, dialysis, reverse osmosis, ultrafiltration, and microfiltration membranes) by administering or coating with the lysin of the invention, including PlySs2 lysin.

Alternative active and suitable lysin(s) may be utilized in accordance with the methods and compositions of the present invention, including as the lysin(s) of use and/or as one or more additional effective and useful lysins. In an additional aspect or embodiment of the methods and uses provided herein, the staphylococcal specific lysin ClyS is used herein alone or in combination with the PlySs2 lysin as provided and described herein.

Other objects and advantages will become apparent to those skilled in the art from a review of the following description which proceeds with reference to the following illustrative drawings.

BRIEF DESCRIPTION OF THE DRAWINGS

FIG. 5 provides the amino acid sequence (SEQ ID NO: 1) and encoding nucleic acid sequence (SEQ ID NO: 2) of the lysin PlySs2. The N-terminal CHAP domain and the C-terminal SH-3 domain of the PlySs2 lysin are shaded, with the CHAP domain starting with LNN . . . and ending with . . . YIT (SEQ ID NO: 3) and the SH-3 domain starting with RSY . . . and ending with . . . VAT (SEQ ID NO: 4). The CHAP domain active-site residues ($Cys_{26}$, $His_{102}$, $Glu_{118}$, and $Asn_{120}$) identified by homology to PDB 2K3A (Rossi P et al (2009) Proteins 74:515-519) are underlined.

FIG. 9A: Catheter biofilms were treated with media alone, 1×MIC daptomycin, 1000×MIC daptomycin and 1×MIC PlySs2 for 24 hours before flushing, staining with methylene blue and photographing. FIG. 9B: After 24 hours of treatment, duplicate catheter samples were treated with lysis buffer to remove residual biofilms and bacterial CFUs estimated based on relative light units using a luciferase reagent calibrated against known concentrations of bacteria.

FIG. 12A: catheters were treated with 1×MIC PlySs2 (32 ug/ml) for 5 min, 15 min, 30 min, 60 min, 90 min, 2 hrs, 3 hrs, 4 hrs and 5 hrs before flushing, staining with methylene blue and photographing. FIG. 12B: After each timed treatment, duplicate catheter samples were treated with lysis buffer to remove residual biofilms and bacterial CFUs estimated based on relative light units using a luciferase reagent calibrated against known concentrations of bacteria.

FIGS. 21A-C depict scanning electron microscopy (SEM) of 3 day old catheter *S. aureus* biofilms treated with PlySs2, washed, fixed and scanned. FIG. 21A: 0 minutes, FIG. 21B: 30 seconds and FIG. 21C: 15 minutes of PlySs2 treatment are shown. 5000× magnification.

DETAILED DESCRIPTION

Figure 1:
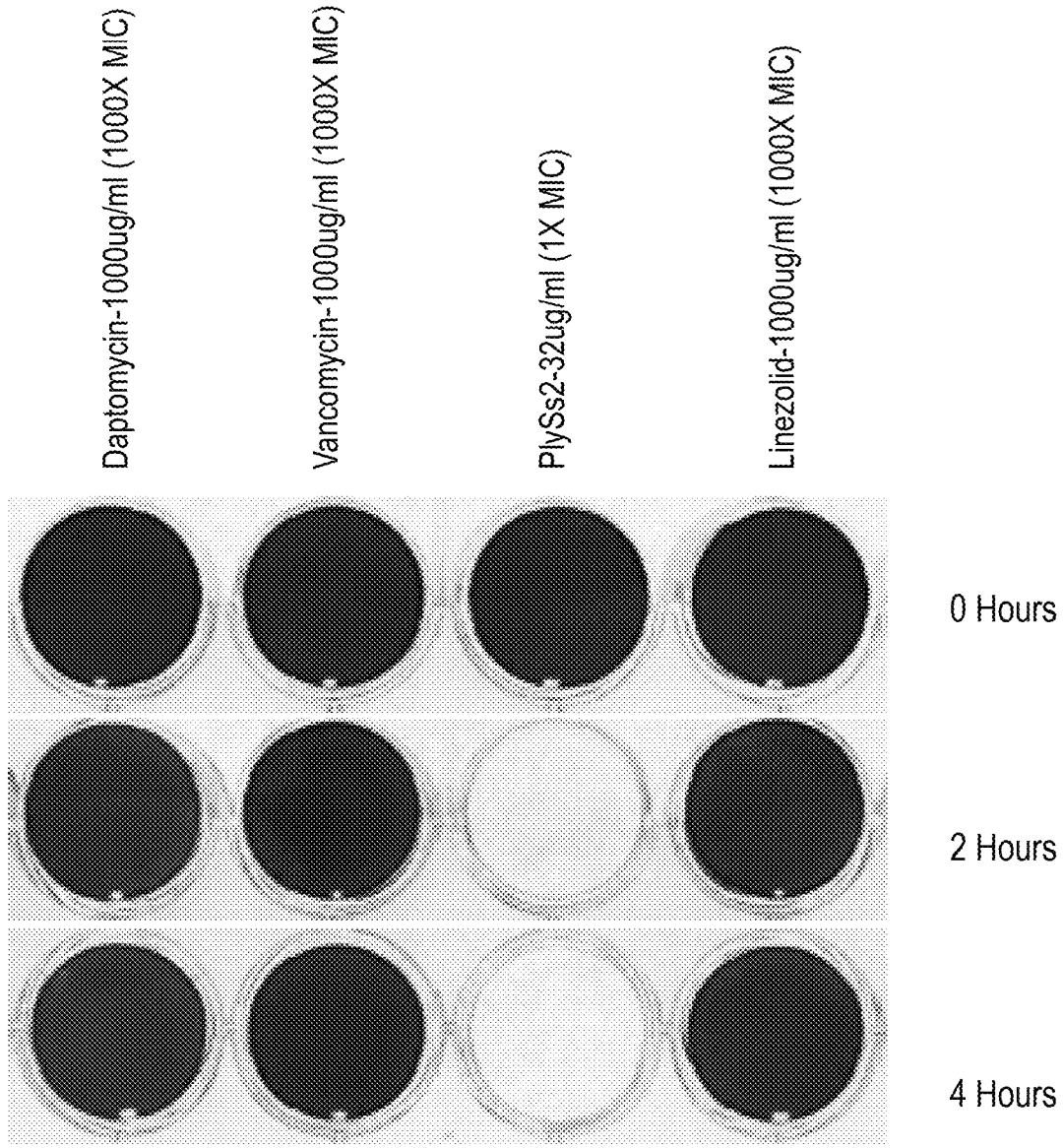
FIG. 1 depicts biofilms of BAA-42 MRSA treated with daptomycin, vancomycin, PlySs2 lysin or linezolid at the amounts and for the times indicated up to 4 hours. Antibiotics daptomycin, vancomycin, and linezolid were added at 1000×MIC for each antibiotic. PlySs2 was added at 1×MIC. After treatment, biofilms are visualized with crystal violet.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "PlySs lysin(s)", "PlySs2 lysin", "PlySs2" and any variants not specifically listed, may be used herein interchangeably, and as used throughout the present application and claims refer to proteinaceous material including single or multiple proteins, and extends to those proteins having the amino acid sequence data described herein and presented in FIG. 5 and SEQ ID NO: 1, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "PlySs lysin(s)", "PlySs2 lysin", "PlySs2" are intended to include within their scope proteins specifically recited herein as well as all substantially homologous analogs, fragments or truncations, and allelic variations. PlySs2 lysin is described in U.S. Patent Application 61/477,836 and PCT Application PCT/US2012/34456. A more recent paper Gilmer et al describes PlySs2 lysin (Gilmer D B et al (2013) Antimicrob Agents Chemother Epub 2013 Apr. 9 [PMID 23571534]).

The term "ClyS", "ClyS lysin" refers to a chimeric lysin ClyS, with activity against Staphylococci bacteria, including *Staphylococcus aureus*, is detailed in WO 2010/002959 and also described in Daniel et al (Daniel, A et al (2010) Antimicrobial Agents and Chemother 54(4):1603-1612). Such exemplary amino acid sequence of ClyS is provided in SEQ ID NO: 5.

A "lytic enzyme" includes any bacterial cell wall lytic enzyme that kills one or more bacteria under suitable conditions and during a relevant time period. Examples of lytic enzymes include, without limitation, various amidase cell wall lytic enzymes.

A "bacteriophage lytic enzyme" refers to a lytic enzyme extracted or isolated from a bacteriophage or a synthesized lytic enzyme with a similar protein structure that maintains a lytic enzyme functionality.

A lytic enzyme is capable of specifically cleaving bonds that are present in the peptidoglycan of bacterial cells to disrupt the bacterial cell wall. It is also currently postulated that the bacterial cell wall peptidoglycan is highly conserved among most bacteria, and cleavage of only a few bonds to may disrupt the bacterial cell wall. The bacteriophage lytic enzyme may be an amidase, although other types of enzymes are possible. Examples of lytic enzymes that cleave these bonds are muramidases, glucosaminidases, endopeptidases, or N-acetyl-muramoyl-L-alanine amidases. Fischetti et al (1974) reported that the C1 streptococcal phage lysin enzyme was an amidase. Garcia et al (1987, 1990) reported that the Cpl lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by *melo*-diaminopemilic acid and D-alanine. The *E. coli* Ti and T6 phage lytic enzymes are amidases as is the lytic enzyme from *Listeria* phage (ply) (Loessner et al, 1996). There are also other lytic enzymes known in the art that are capable of cleaving a bacterial cell wall.

A "lytic enzyme genetically coded for by a bacteriophage" includes a polypeptide capable of killing a host bacteria, for instance by having at least some cell wall lytic activity against the host bacteria. The polypeptide may have a sequence that encompasses native sequence lytic enzyme and variants thereof. The polypeptide may be isolated from a variety of sources, such as from a bacteriophage ("phage"), or prepared by recombinant or synthetic methods. The polypeptide may comprise a choline-binding portion at the carboxyl terminal side and may be characterized by an enzyme activity capable of cleaving cell wall peptidoglycan (such as amidase activity to act on amide bonds in the peptidoglycan) at the amino terminal side. Lytic enzymes have been described which include multiple enzyme activities, for example two enzymatic domains, such as PlyGBS lysin.

"A native sequence phage associated lytic enzyme" includes a polypeptide having the same amino acid sequence as an enzyme derived from a bacteria. Such native sequence enzyme can be isolated or can be produced by recombinant or synthetic means.

The term "native sequence enzyme" encompasses naturally occurring forms (e.g., alternatively spliced or altered forms) and naturally-occurring variants of the enzyme. In one embodiment of the invention, the native sequence enzyme is a mature or full-length polypeptide that is genetically coded for by a gene from a bacteriophage specific for *Streptococcus suis*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987);

Lopez et al., FEMS Microbiol. Lett. 100: 439-448 (1992); Romero et al., J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence lytic enzyme" includes a lytic enzyme characterized by a polypeptide sequence that is different from that of a lytic enzyme, but retains functional activity. The lytic enzyme can, in some embodiments, be genetically coded for by a bacteriophage specific for *Streptococcus suis* as in the case of PlySs2 having a particular amino acid sequence identity with the lytic enzyme sequence(s) hereof, as provided in FIG. 5 and SEQ ID NO:1. For example, in some embodiments, a functionally active lytic enzyme can kill *Streptococcus suis* bacteria, and other susceptible bacteria as provided herein, including as shown in TABLE 1, 2 and 3, by disrupting the cellular wall of the bacteria. An active lytic enzyme may have a 60, 65, 70, 75, 80, 85, 90, 95, 97, 98, 99 or 99.5% amino acid sequence identity with the lytic enzyme sequence(s) hereof, as provided in FIG. 5 and in SEQ ID NO: 1. Such phage associated lytic enzyme variants include, for instance, lytic enzyme polypeptides wherein one or more amino acid residues are added, or deleted at the N or C terminus of the sequence of the lytic enzyme sequence(s) hereof, as provided in FIG. 5 and in SEQ ID NO: 1.

In a particular aspect, a phage associated lytic enzyme will have at least about 80% or 85% amino acid sequence identity with native phage associated lytic enzyme sequences, particularly at least about 90% (e.g. 90%) amino acid sequence identity. Most particularly a phage associated lytic enzyme variant will have at least about 95% (e.g. 95%) amino acid sequence identity with the native phage associated the lytic enzyme sequence(s) hereof, as provided in FIG. 5 and in SEQ ID NO: 1 for PlySs2 lysin, or as preciously described for ClyS including in WO 2010/002959 and also described in Daniel et al (Daniel, A et al (2010) Antimicrobial Agents and Chemother 54(4):1603-1612).

"Percent amino acid sequence identity" with respect to the phage associated lytic enzyme sequences identified is defined herein as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity.

To determine the percent identity of two nucleotide or amino acid sequences, the sequences are aligned for optimal comparison purposes (e.g., gaps may be introduced in the sequence of a first nucleotide sequence). The nucleotides or amino acids at corresponding nucleotide or amino acid positions are then compared. When a position in the first sequence is occupied by the same nucleotide or amino acid as the corresponding position in the second sequence, then the molecules are identical at that position. The percent identity between the two sequences is a function of the number of identical positions shared by the sequences (i.e., % identity=(# of identical positions/total # of positions)× 100).

The determination of percent identity between two sequences may be accomplished using a mathematical algorithm. A non-limiting example of a mathematical algorithm utilized for the comparison of two sequences is the algorithm of Karlin et al., Proc. Natl. Acad. Sci. USA, 90:5873-5877 (1993), which is incorporated into the NBLAST program which may be used to identify sequences having the desired identity to nucleotide sequences of the invention. To obtain gapped alignments for comparison purposes, Gapped BLAST may be utilized as described in Altschul et al., Nucleic Acids Res, 25:3389-3402 (1997). When utilizing BLAST and Gapped BLAST programs, the default parameters of the respective programs (e.g., NBLAST) may be used. See the programs provided by National Center for Biotechnology Information, National Library of Medicine, National Institutes of Health.

"Polypeptide" includes a polymer molecule comprised of multiple amino acids joined in a linear manner. A polypeptide can, in some embodiments, correspond to molecules encoded by a polynucleotide sequence which is naturally occurring. The polypeptide may include conservative substitutions where the naturally occurring amino acid is replaced by one having similar properties, where such conservative substitutions do not alter the function of the polypeptide.

The term "altered lytic enzymes" includes shuffled and/or chimeric lytic enzymes.

Phage lytic enzymes specific for bacteria infected with a specific phage have been found to effectively and efficiently break down the cell wall of the bacterium in question. The lytic enzyme is believed to lack proteolytic enzymatic activity and is therefore non-destructive to mammalian proteins and tissues when present during the digestion of the bacterial cell wall. Furthermore, because it has been found that the action of phage lytic enzymes, unlike antibiotics, was rather specific for the target pathogen(s), it is likely that the normal flora will remain essentially intact (M. J. Loessner, G. Wendlinger, S. Scherer, Mol Microbiol 16, 1231-41. (1995) incorporated herein by reference). In fact, the PlySs2 lysin, while demonstrating uniquely broad bacterial species and strain killing, is comparatively and particularly inactive against bacteria comprising the normal flora, including *E. coli*, as described herein.

A lytic enzyme or polypeptide of use in the invention may be produced by the bacterial organism after being infected with a particular bacteriophage or may be produced or prepared recombinantly or synthetically as either a prophylactic treatment for preventing those who have been exposed to others who have the symptoms of an infection from getting sick, or as a therapeutic treatment for those who have already become ill from the infection. In as much the lysin polypeptide sequences and nucleic acids encoding the lysin polypeptides are described and referenced to herein, the lytic enzyme(s)/polypeptide(s) may be preferably produced via the isolated gene for the lytic enzyme from the phage genome, putting the gene into a transfer vector, and cloning said transfer vector into an expression system, using standard methods of the art, including as exemplified herein. The lytic enzyme(s) or polypeptide(s) may be truncated, chimeric, shuffled or "natural," and may be in combination. Relevant U.S. Pat. No. 5,604,109 is incorporated herein in its entirety by reference. An "altered" lytic enzyme can be produced in a number of ways. In a preferred embodiment, a gene for the altered lytic enzyme from the phage genome is put into a transfer or movable vector, preferably a plasmid, and the plasmid is cloned into an expression vector or expression system. The expression vector for producing a lysin polypeptide or enzyme of the invention may be suitable for *E. coli*, *Bacillus*, or a number of other suitable bacteria. The vector system may also be a cell free expression system. All of these methods of expressing a gene or set of genes are known in the art. The lytic enzyme may also be created by infecting *Streptococcus suis* with a bacteriophage specific for *Streptococcus suis*, wherein said at least one lytic enzyme exclusively lyses the cell wall of said *Streptococcus suis* having at most minimal effects on other, for example natural or commensal, bacterial flora present (see TABLE 5, which provides the results of lytic activity studies against various commensal human gut bacteria).

A "chimeric protein" or "fusion protein" comprises all or (preferably a biologically active) part of a polypeptide of use in the invention operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also may be used to treat a bacterial infection by cleaving the cell wall in more than one location, thus potentially providing more rapid or effective (or synergistic) killing from a single lysin molecule or chimeric peptide.

A "heterologous" region of a DNA construct or peptide construct is an identifiable segment of DNA within a larger DNA molecule or peptide within a larger peptide molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA or peptide as defined herein.

The term "operably linked" means that the polypeptide of the disclosure and the heterologous polypeptide are fused in-frame. The heterologous polypeptide can be fused to the N-terminus or C-terminus of the polypeptide of the disclosure. Chimeric proteins are produced enzymatically by chemical synthesis, or by recombinant DNA technology. A number of chimeric lytic enzymes have been produced and studied. One example of a useful fusion protein is a GST fusion protein in which the polypeptide of the disclosure is fused to the C-terminus of a GST sequence. Such a chimeric protein can facilitate the purification of a recombinant polypeptide of the disclosure.

In another embodiment, the chimeric protein or peptide contains a heterologous signal sequence at its N-terminus. For example, the native signal sequence of a polypeptide of the disclosure can be removed and replaced with a signal sequence from another known protein.

The fusion protein may combine a lysin polypeptide with a protein or polypeptide of having a different capability, or providing an additional capability or added character to the lysin polypeptide. The fusion protein may be an immunoglobulin fusion protein in which all or part of a polypeptide of the disclosure is fused to sequences derived from a member of the immunoglobulin protein family. The immunoglobulin may be an antibody, for example an antibody directed to a surface protein or epitope of a susceptible or target bacteria. The immunoglobulin fusion protein can alter bioavailability of a cognate ligand of a polypeptide of the disclosure. Inhibition of ligand/receptor interaction may be useful therapeutically, both for treating bacterial-associated diseases and disorders for modulating (i.e. promoting or inhibiting) cell survival. The fusion protein may include a means to direct or target the lysin, including to particular tissues or organs or to surfaces such as devices, plastic, membranes. Chimeric and fusion proteins and peptides of the disclosure can be produced by standard recombinant DNA techniques.

A modified or altered form of the protein or peptides and peptide fragments, as disclosed herein, includes protein or peptides and peptide fragments that are chemically synthesized or prepared by recombinant DNA techniques, or both. These techniques include, for example, chimerization and shuffling. As used herein, shuffled proteins or peptides, gene products, or peptides for more than one related phage protein or protein peptide fragments have been randomly cleaved and reassembled into a more active or specific protein. Shuffled oligonucleotides, peptides or peptide fragment molecules are selected or screened to identify a molecule having a desired functional property. Shuffling can be used to create a protein that is more active, for instance up to 10 to 100 fold more active than the template protein. The template protein is selected among different varieties of lysin proteins. The shuffled protein or peptides constitute, for example, one or more binding domains and one or more catalytic domains. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

The present invention also pertains to other variants of the polypeptides useful in the invention. Such variants may have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of use in the disclosure which function as either agonists (mimetics) or as antagonists can be identified by screening combinatorial libraries of mutants, such as truncation mutants, of the protein of the disclosure. In one embodiment, a variegated library of variants is generated by combinatorial mutagenesis at the nucleic acid level and is encoded by a variegated gene library. There are a variety of methods which can be used to produce libraries of potential variants of the polypeptides of the disclosure from a degenerate oligonucleotide sequence. Libraries of fragments of the coding sequence of a polypeptide of the disclosure can be used to generate a variegated population of polypeptides for screening and subsequent selection of variants, active fragments or truncations. Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind a target or receptor, such as an antibody, and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as targets or epitopes, shorter sequences of 5, 6, or 7 amino acids long can exhibit target or epitopic structure in some conditions and have value in an embodiment. Thus, the smallest portion of the protein(s) or lysin polypeptides provided herein, including as set out in FIG. 5 and SEQ ID NO:1 and the domain sequences of SEQ ID NO: 3 and 4 includes polypeptides as small as 5, 6, 7, 8, 9, 10, 12, 14 or 16 amino acids long.

Biologically active portions of a protein or peptide fragment of the embodiments, as described herein, include polypeptides comprising amino acid sequences sufficiently identical to or derived from the amino acid sequence of the lysin protein of the disclosure, which include fewer amino acids than the full length protein of the lysin protein and exhibit at least one activity of the corresponding full-length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules that may be homologous specifically are intended as embodiments. Preferably the homology of such valuable regions is at least 50%, 65%, 75%, 80%, 85%, and preferably at least 90%, 95%, 97%, 98%, or at least 99% compared to the lysin polypeptides provided herein, including as set out in FIG. 5 and SEQ ID NO: 1 and the domain sequences of SEQ ID NO: 3 and 4. These percent homology values do not include alterations due to conservative amino acid substitutions.

Two amino acid sequences are "substantially homologous" when at least about 70% of the amino acid residues (preferably at least about 80%, at least about 85%, and preferably at least about 90 or 95%) are identical, or represent conservative substitutions. The sequences of comparable lysins, such as comparable PlySs2 lysins, or comparable ClyS lysins, are substantially homologous when one or more, or several, or up to 10%, or up to 15%, or up to 20% of the amino acids of the lysin polypeptide are substituted with a similar or conservative amino acid substitution, and wherein the comparable lysins have the profile of activities, anti-bacterial effects, and/or bacterial specificities of a lysin, such as the PlySs2 lysin and/or ClyS lysin, disclosed herein.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

Mutations can be made in the amino acid sequences, or in the nucleic acid sequences encoding the polypeptides and lysins herein, including in the lysin sequences set out in FIG. 5 and in SEQ ID NO: 1 or in the domain sequences of SEQ ID NO: 3 or 4, or in active fragments or truncations thereof, such that a particular codon is changed to a codon which codes for a different amino acid, an amino acid is substituted for another amino acid, or one or more amino acids are deleted. Such a mutation is generally made by making the fewest amino acid or nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic amino acids (positively charged at pH 6.0)
Lysine, Arginine, Histidine (at pH 6.0)
Another grouping may be those amino acids with phenyl groups: Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of:
glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Thus, one of skill in the art, based on a review of the sequence of the PlySs2 lysin polypeptide provided herein and on their knowledge and the public information available for other lysin polypeptides, can make amino acid changes or substitutions in the lysin polypeptide sequence. Amino acid changes can be made to replace or substitute one or more, one or a few, one or several, one to five, one to ten, or such other number of amino acids in the sequence of the lysin(s) provided herein to generate mutants or variants thereof. Such mutants or variants thereof may be predicted for function or tested for function or capability for killing bacteria, including Staphylococcal, Streptococcal, *Listeria*, or Enterococcal bacteria, and/or for having comparable activity to the lysin(s) as described and particularly provided herein. Thus, changes can be made to the sequence of lysin, and mutants or variants having a change in sequence can be tested using the assays and methods described and exemplified herein, including in the examples. One of skill in the art, on the basis of the domain structure of the lysin(s) hereof can predict one or more, one or several amino acids suitable for substitution or replacement and/or one or more amino acids which are not suitable for substitution or replacement, including reasonable conservative or non-conservative substitutions.

In this regard, and with exemplary reference to PlySs2 lysin it is pointed out that, although the PlySs2 polypeptide lysin represents a divergent class of prophage lytic enzyme, the lysin comprises an N-terminal CHAP domain (cysteine-histidine amidohydrolase/peptidase) (SEQ ID NO: 3) and a C-terminal SH3-type 5 domain (SEQ ID NO: 4) as depicted in FIG. 5. The domains are depicted in the amino acid sequence in distinct shaded color regions, with the CHAP domain corresponding to the first shaded amino acid sequence region starting with LNN . . . and the SH3-type 5 domain corresponding to the second shaded region starting with RSY . . . CHAP domains are included in several previously characterized streptococcal and staphylococcal phage lysins. Thus, one of skill in the art can reasonably make and test substitutions or replacements to the CHAP domain and/or the SH-3 domain of PlySs2. Sequence comparisons to the Genbank database can be made with either or both of the CHAP and/or SH-3 domain sequences or with the PlySs2 lysin full amino acid sequence, for instance, to identify amino acids for substitution.

The PlySs2 lysin displays activity and capability to kill numerous distinct strains and species of gram positive bacteria, including Staphylococcal, Streptococcal, *Listeria*, or Enterococcal bacteria. In particular and with significance, PlySs2 is active in killing *Staphylococcus* strains, including *Staphylococcus aureus*, particularly both antibiotic-sensitive and distinct antibiotic-resistant strains. PlySs2 is also active in killing *Streptococcus* strains, and shows particularly effective killing against Group A and Group B *streptococcus* strains. PlySs2 lysin capability against bacteria is depicted below in TABLE 1, based on log kill assessments using isolated strains in vitro. Activity of PlySs2 against various Gram-positive and Gram-negative organisms and against antibiotic resistant *Staphylococcus aureus* strains is tabulated below in TABLES 2 and 3. MIC ranges for PlySs2 against the bacteria is noted to provide relative killing activity.

TABLE 1

PlySs2 Reduction in Growth of Different Bacteria (partial listing)

| Bacteria | Relative Kill with PlvSs2 |
|---|---|
| Staphylococcus aureus (VRSA, VISA, MRSA, MSSA) | +++ |
| Streptococcus suis | +++ |
| Staphylococcus epidermidis | ++ |
| Staphylococcus simulans | +++ |
| Lysteria monocytogenes | ++ |
| Enterococcus faecalis | ++ |
| Streptococcus dysgalactiae—GBS | ++ |
| Streptococcus agalactiae—GBS | +++ |
| Streptococcus pyogenes—GAS | +++ |
| Streptococcus equi | ++ |
| Streptococcus sanguinis | ++ |
| Streptococcus gordonii | ++ |
| Streptococcus sobrinus | + |
| Streptococcus rattus | + |
| Streptococcus oralis | + |
| Streptococcus pneumonine | + |
| Bacillus thuringiensis | − |
| Bacillus cereus | − |
| Bacillus subtilis | − |
| Bacillus anthracis | − |
| Escherichia coli | − |
| Enterococcus faecium | − |
| Pseudomanas aeruginosa | − |

TABLE 2

Susceptible and Non-susceptible Bacterial Strains

| Organism and susceptibility subset (no. tested) | MIC (μg/mL) | | |
|---|---|---|---|
| | 50% | 90% | Range |
| *Staphylcoccus aureus* | | | |
| Methicillin susceptible (103) | 4 | 8 | 1-16 |
| Methicillin resistant (120) | 4 | 8 | 1-16 |
| Streptococcus pyogenes, Group A (54) | 2 | 8 | 0.5-8 |
| Streptococcus agalactiae, Group B (51) | 8 | 16 | 1-64 |
| Other Gram-positive organisms | | | |
| Staphylococcus lugdiensis (10) | 8 | 8 | 8 |
| Staphylococcus epidermidis (11) | 128 | 512 | 4-512 |
| Streptococcus pneumoniae (26) | 16 | 64 | 1-64 |
| Streptococcus mutans (12) | 64 | 256 | 2-256 |
| Listeria monocytogenes (12) | 128 | 512 | 1-512 |
| Enterococcus faecalis (17) | >512 | >512 | 32->512 |
| Enterococcus faecium (5) | >512 | >512 | 32->512 |
| Bacillus cereus (10) | >512 | >512 | >512 |
| Gram-negative organisms | | | |
| Acinetobacter baumannii (8) | >512 | >512 | >512 |
| Escherichia coli (6) | >512 | >512 | >512 |
| Pseudomonas aeruginosa (5) | >512 | >512 | >512 |

TABLE 3

Activity of PlySs2 Against Antibiotic-Resistant *Staphylococcus aureus*

| Susceptibility subset (no. tested) | MIC (mg/mL) | | |
|---|---|---|---|
| | 50% | 90% | Range |
| Vancomycin-resistant (14) | 2 | 4 | 1-4 |
| Vancomycin-intermediate (31) | 8 | 32 | 1-64 |
| Linezolid-resistant (5) | 2 | 2 | 2-4 |
| Daptomycin-resistant (8) | 2 | 4 | 2-4 |

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "specific" may be used to refer to the situation in which one member of a specific binding pair will not show significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention hereof, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which the lysin polypeptide(s) of the invention, or nucleic acid encoding such polypeptides will be, in accordance with the present invention. Polypeptides and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Polypeptides and nucleic acid may be formulated with diluents or adjuvants and still for practical purposes be isolated—for example the polypeptides will normally be mixed with polymers or mucoadhesives or other carriers, or will be mixed with pharmaceutically acceptable carriers or diluents, when used in diagnosis or therapy.

Nucleic acids capable of encoding the S. suis PlySs2 lysin polypeptide(s) useful and applicable in the invention are provided herein. Representative nucleic acid sequences in this context are polynucleotide sequences coding for the polypeptide of FIG. 5 or SEQ ID NO: 1, particularly polynucleotide sequences of SEQ ID NO: 2 capable of encoding the polypeptide of SEQ ID NO: 1, and sequences that hybridize, under stringent conditions, with complementary sequences of the DNA of SEQ ID NO: 2 and/or the FIG. 5 sequence(s). Further variants of these sequences and sequences of nucleic acids that hybridize with those shown in the figures also are contemplated for use in production of lysing enzymes according to the disclosure, including natural variants that may be obtained. A large variety of isolated nucleic acid sequences or cDNA sequences that encode phage associated lysing enzymes and partial sequences that hybridize with such gene sequences are useful for recombinant production of the lysin enzyme(s) or polypeptide(s) of the invention.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

DNA molecules and nucleotide sequences which are derivatives of those specifically disclosed herein and which differ from those disclosed by the deletion, addition or substitution of nucleotides while still encoding a protein which possesses the functional characteristic of the lysin polypeptide(s) are contemplated by the disclosure. Also included are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage of *Staphylococcus* suis and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

In preferred embodiments of the present disclosure, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. Preferably, stringent conditions are those under which DNA sequences with more than 6% mismatch will not hybridize.

The degeneracy of the genetic code further widens the scope of the embodiments as it enables major variations in the nucleotide sequence of a DNA molecule while maintaining the amino acid sequence of the encoded protein. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

Thus, it should be appreciated that also within the scope of the present invention are DNA sequences encoding a lysin of the present invention, including PlySs2 and PlySs1, which sequences code for a polypeptide having the same amino acid sequence as provided in FIG. 5 or SEQ ID NO: 1, but which are degenerate thereto or are degenerate to the exemplary nucleic acids sequences provided in FIG. 5 and in SEQ ID NO: 2. By "degenerate to" is meant that a different three-letter codon is used to specify a particular amino acid. It is well known in the art the codons which can be used interchangeably to code for each specific amino acid.

One skilled in the art will recognize that the DNA mutagenesis techniques described here and known in the art can produce a wide variety of DNA molecules that code for a bacteriophage lysin of *Streptococcus suis* yet that maintain the essential characteristics of the lytic polypeptides described and provided herein. Newly derived proteins may also be selected in order to obtain variations on the characteristic of the lytic polypeptide(s), as will be more fully described below. Such derivatives include those with variations in amino acid sequence including minor deletions, additions and substitutions.

While the site for introducing an amino acid sequence variation may be predetermined, the mutation per se does not need to be predetermined. Amino acid substitutions are typically of single residues, or can be of one or more, one or a few, one, two, three, four, five, six or seven residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Substitution variants are those in which at least one residue in the amino acid sequence has been removed and a different residue inserted in its place. Such substitutions may be made so as to generate no significant effect on the protein characteristics or when it is desired to finely modulate the characteristics of the protein. Amino acids which may be substituted for an original amino acid in a protein and which are regarded as conservative substitutions are described above and will be recognized by one of skill in the art.

As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and synthetic DNA sequences. Any of a wide variety of expression control sequences—sequences that control the expression of a DNA sequence operatively linked to it—may be used in these vectors to express the DNA sequences of this invention. A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, human cells and plant cells in tissue culture. One skilled in the art will be able to select the proper vectors, expression control sequences, and hosts without undue experimentation to accomplish the desired expression without departing from the scope of this invention.

As used herein and referred to in the art, a biofilm is an aggregate of microbes with a distinct architecture. Biofilm formation involves attachment of free floating microorganisms to a surface. A biofilm is essentially a collective in which microbial cells, each only a micrometer or two long, form convoluted structures, including towers that can be hundreds of micrometers high. The channels within biofilms act as fluid-filled conduits that circulate nutrients, oxygen, waste products, etc., as required to maintain a viable biofilm community. The biofilm or microbial (bacterial, fungal, or algal) community is typically enveloped by extracellular biopolymers produced by the microbial cells and adheres to the interface between a liquid and surface. The encapsulated property of biofilms is one of several features that renders the microbial organisms therein highly resistant to standard anti-microbial therapeutics. Bacteria growing in a biofilm, for example, are highly resistant to antibiotics, and in some cases are up to 1,000 times more resistant than the same bacteria growing without a biofilm superstructure.

Standard antibiotic therapy can be useless wherein a biofilm contaminated implant is detected and the only recourse under such circumstances may be to remove the contaminated implant. Biofilms are, furthermore, involved in numerous chronic diseases. Cystic fibrosis patients, for example, suffer from *Pseudomonas* infections that often result in antibiotic resistant biofilms. Biofilm formation occurs when free floating microorganisms attach themselves to a surface. Because biofilms protect the bacteria, they are often more resistant to traditional antimicrobial treatments, making them a serious health risk, which is evidenced by more than one million cases of catheter-associated urinary tract infections (CAUTI) reported each year, many of which can be attributed to biofilm-associated bacteria (Donlan, R M (2001) Emerg Infect Dis7(2):277-281; Maki D and Tambyah P (2001) Emerg Infect Dis 7(2):342-347)

Various approaches have been attempted to prevent biofilm formation and include inhibiting protein adsorption or biofilm adhesion using chemical and mechanical means. Chemical approaches include antimicrobial coatings on indwelling devices and polymer modifications. Antibiotics, biocides, and ion coatings are examples of chemical methods of biofilm prevention and may interfere with the attachment and expansion of immature biofilms. However, these coatings are effective only for a short time period (about 1 week), after which leaching of the antimicrobial agent reduces the effectiveness of the coating (Dror N et al (2009) Sensors 9(4):2538-2554). Several in vitro studies have confirmed the effectiveness of silver at preventing infection, both in coating form and as nanoparticles dispersed in a polymer matrix. However, concerns remain over the use of silver in vivo with potential toxic effects on human tissue and there has been limited use of silver coatings. Despite this, silver coatings are used on devices such as catheters (Vasilev K et al (2009) Expert Rev Med Devices 6(5):553-567). Via polymer modification, antimicrobial agents can be immobilized on device surfaces using long, flexible polymeric chains. These chains are anchored to the device surface by covalent bonds, producing non-leaching, contact-killing surfaces. An in vitro study found that when N-alkylpyridinium bromide, an antimicrobial agent, was attached to a poly(4-vinyl-N-hexylpyridine), the polymer was capable of inactivating more than 99% of *S. epidermidis, E. coli*, and *P. aeruginosa* bacteria (Jansen B and Kohnen W (1995) J Ind Microbiol 15(4):391-396).

Mechanical approaches to preventing biofilms include altering the surface of devices such as catheters, including modifying the hydrophobicity of the device surface, altering its physical nature using smooth-surfaced materials, and altering surface charge. The hydrophobicity and the charge of polymeric chains can be controlled by using several backbone compounds and antimicrobial agents, including positively charged polycations. In another approach, low-energy surface acoustic waves are produced from a battery powered device that delivers periodic rectangular pulses and waves spread to the surface, in this case a catheter, creating horizontal waves that prevent the adhesion of bacteria to surfaces. This technique has been tested on white rabbits and guinea pigs and lowered biofilm growth (Hazan, Z et al (2006) Antimicrob Agents and Chemother 50(12):4144-152).

In accordance with the present invention, methods and compositions are provided for prevention, dispersion and treatment of bacterial biofilms. Methods and compositions are particularly provided for prevention, dispersion and treatment of biofilms comprising Staphylococcal bacteria. In particular, methods and compositions for prevention, dispersion and treatment of biofilms comprising *Staphylococcus aureus*, including or comprising antibiotic-resistant and/or antibiotic-sensitive *S. aureus* are an aspect of the invention. In an aspect of the invention, the methods and compositions of the invention comprise a lysin, particularly PlySs2 lysin, which is capable of killing Staphylococcal and Streptococcal bacteria, including antibiotic-resistant bacteria.

The methods and compositions of the invention, particularly comprising PlySs2 lysin, may be combined or incorporated with chemical or mechanical means, compositions or approaches for prevention or dispersion of biofilms. Thus, the compositions herein may be combined or incorporated with antibiotics, biocides, and ion coatings in minimizing the growth or establishment of biofilms, particularly in or on in-dwelling devices or catheters. By way of example and not limitation, a composition comprising PlySs2 may be administered or otherwise provided in presterilizing or maintaining an indwelling device or catheter biofilm free or with reduced bacterial adhesion or reduced risk of biofilm formation. Thus, a composition comprising PlySs2 may be utilized in solution to flush or regularly clean and maintain an indwelling device, catheter, etc biofilm free or with reduced bacterial adhesion or reduced risk of biofilm formation. In an instance where a biofilm is suspected, evident, or demonstrated, a composition comprising PlySs2 may be administered or otherwise contacted with the biofilm or the device, region, location, site so as to facilitate, initiate, or result in dispersion, alleviation, removal, or treatment of the biofilm. Thus, for example, in instances wherein a patient presents with elevated temperature, or with discomfort, redness, swelling associated with around a device or catheter, a composition comprising PlySs2 may be administered to the patient or contacted with the device or catheter to alleviate, dispel or treat the relevant temperature, discomfort, redness, swelling by dispersing, preventing or treating any biofilm being formed or having formed.

In accordance with the invention, a composition comprising lysin, particularly PlySs2 lysin or active variants thereof, may be administered or otherwise contacted with an established or suspected biofilm or the device, region, location, site with biofilm, in a single or in multiple doses or administrations. The lysin may be administered along with, before, or after one or more antibiotic. The lysin may be administered in an initial dose, for example, followied by or along with antibiotic, and the initial dose of lysin may be followed by a subsequent dose of lysin. In one such situation, the initial dose of lysin, particularly PlySs2, may serve to disperse the biofilm, followed by a subsequent dose of lysin (of lower, same or higher amount, which may depend in part on the initial response and dispersion of the biofilm) which may serve to further disperse or additionally kill or decolonize the bacteria in or of or from the biofilm. A dose of antibiotic may be administered also subsequently or in addition to further serve to disperse or additionally kill or decolonize the bacteria in or of or from the biofilm.

Therapeutic or pharmaceutical compositions comprising the lytic enzyme(s)/polypeptide(s) of use in the methods and applications provided in the invention are provided herein, as well as related methods of use. Therapeutic or pharmaceutical compositions may comprise one or more lytic polypeptide(s), and optionally include natural, truncated, chimeric or shuffled lytic enzymes, optionally combined with other components such as a carrier, vehicle, polypeptide, polynucleotide, holin protein(s), one or more antibiotics or suitable excipients, carriers or vehicles. The invention provides therapeutic compositions or pharmaceutical compositions of the lysins of the invention, including PlySs2 for use in the killing, alleviation, decolonization, prophylaxis or treatment of gram-positive bacteria in biofilms and particularly for dispersing, preventing or treating biofilms.

The enzyme(s) or polypeptide(s) included in the therapeutic compositions of use in the method of the invention may be one or more or any combination of unaltered phage associated lytic enzyme(s), truncated lytic polypeptides, variant lytic polypeptide(s), and chimeric and/or shuffled lytic enzymes. Additionally, different lytic polypeptide(s) genetically coded for by different phage for treatment of the same bacteria may be used. These lytic enzymes may also be any combination of "unaltered" lytic enzymes or polypeptides, truncated lytic polypeptide(s), variant lytic polypeptide(s), and chimeric and shuffled lytic enzymes. The lytic enzyme(s)/polypeptide(s) in a therapeutic or pharmaceutical composition for gram-positive bacteria, including *Streptococcus, Staphylococcus, Enterococcus* and *Listeria*, may be used alone or in combination with antibiotics or, if there are other invasive bacterial organisms to be treated, in combination with other phage associated lytic enzymes specific for other bacteria being targeted. The lytic enzyme, truncated enzyme, variant enzyme, chimeric enzyme, and/or shuffled lytic enzyme may be used in conjunction with a holin protein. The amount of the holin protein may also be varied. Various antibiotics may be optionally included in the therapeutic composition with the enzyme(s) or polypeptide(s) and with or without the presence of lysostaphin. More than one lytic enzyme or polypeptide may be included in the therapeutic composition.

The pharmaceutical composition of use in the method of the invention can also include one or more altered lytic enzymes, including isozymes, analogs, or variants thereof, produced by chemical synthesis or DNA recombinant techniques. In particular, altered lytic protein can be produced by amino acid substitution, deletion, truncation, chimerization, shuffling, or combinations thereof. The pharmaceutical composition may contain a combination of one or more natural lytic protein and one or more truncated, variant, chimeric or shuffled lytic protein. The pharmaceutical composition may also contain a peptide or a peptide fragment of at least one lytic protein derived from the same or different bacteria species, with an optional addition of one or more complementary agent, and a pharmaceutically acceptable carrier or diluent.

The pharmaceutical composition of use in the present methods can contain a complementary agent, including one or more antimicrobial agent and/or one or more conventional antibiotics, particularly as provided herein. In order to accelerate treatment of the infection or dispersion of the bacterial biofilm, the therapeutic agent may further include at least one complementary agent which can also potentiate the bactericidal activity of the lytic enzyme. Antimicrobials act largely by interfering with the structure or function of a bacterial cell by inhibition of cell wall synthesis, inhibition of cell-membrane function and/or inhibition of metabolic functions, including protein and DNA synthesis. Antibiotics can be subgrouped broadly into those affecting cell wall peptidoglycan biosynthesis and those affecting DNA or protein synthesis in gram positive bacteria. Cell wall synthesis inhibitors, including penicillin and antibiotics like it, disrupt the rigid outer cell wall so that the relatively unsupported cell swells and eventually ruptures. The complementary agent may be an antibiotic, such as erythromycin, clarithromycin, azithromycin, roxithromycin, other members of the macrolide family, penicillins, cephalosporins, and any combinations thereof in amounts which are effective to synergistically enhance the therapeutic effect of the lytic enzyme. Virtually any other antibiotic may be used with the altered and/or unaltered lytic enzyme. Antibiotics affecting cell wall peptidoglycan biosynthesis include: Glycopeptides, which inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin; Penicillins, which act by inhibiting the formation of peptidoglycan cross-links. The functional group of penicillins, the β-lactam moiety, binds and inhibits DD-transpeptidase that links the peptidoglycan molecules in bacteria. Hydrolytic enzymes continue to break down the cell wall, causing cytolysis or death due to osmotic pressure. Common penicillins include oxacillin, ampicillin and cloxacillin; and Polypeptides, which interfere with the dephosphorylation of the $C_{55}$-isoprenyl pyrophosphate, a molecule that carries peptidoglycan building-blocks outside of the plasma membrane. A cell wall-impacting polypeptide is bacitracin. Other useful and relevant antibiotics include vancomycin, linezolid, and daptomycin.

Similarly, other lytic enzymes may be included in the carrier to treat or disperse other bacteria or bacterial infections. The pharmaceutical composition can also contain a peptide or a peptide fragment of at least one lytic protein, one holin protein, or at least one holin and one lytic protein, which lytic and holin proteins are each derived from the same or different bacteria species, with an optional addition of one or more complementary agent(s), and a suitable carrier or diluent.

Also of use in the methods are compositions containing nucleic acid molecules that, either alone or in combination with other nucleic acid molecules, are capable of expressing an effective amount of a lytic polypeptide(s) or a peptide fragment of a lytic polypeptide(s) in vivo. Cell cultures containing these nucleic acid molecules, polynucleotides, and vectors carrying and expressing these molecules in vitro or in vivo, are also provided.

The present methods may utilize therapeutic or pharmaceutical compositions that comprise lytic polypeptide(s) combined with a variety of carriers to disperse or decolonize the bacteria or treat the illnesses caused by the susceptible gram-positive bacteria. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts. Glycerin or glycerol (1,2,3-propanetriol) is commercially available for pharmaceutical use. DMSO is an aprotic solvent with a remarkable ability to enhance penetration of many locally applied drugs. The carrier vehicle may also include Ringer's solution, a buffered solution, and dextrose solution, particularly when an intravenous solution is prepared.

A lytic polypeptide(s) may be added to these substances in a liquid form or in a lyophilized state, whereupon it will be solubilized when it meets body fluids such as saliva. The polypeptide(s)/enzyme may also be in a micelle or liposome.

The effective dosage rates or amounts of an altered or unaltered lytic enzyme/polypeptide(s) of and for use in the present invention will depend in part on whether the lytic enzyme/polypeptide(s) will be used therapeutically or prophylactically, the duration of exposure of the recipient to the infectious bacteria, the size and weight of the individual, etc. The duration for use of the composition containing the enzyme/polypeptide(s) also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. Carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. There are situations where it may be necessary to have a much higher unit/ml dosage or a lower unit/ml dosage.

The lytic enzyme/polypeptide(s) for use should be in an environment having a pH which allows for activity of the lytic enzyme/polypeptide(s). A stabilizing buffer may allow for the optimum activity of the lysin enzyme/polypeptide(s). The buffer may contain a reducing reagent, such as dithiothreitol or beta mercaptoethanol (BME). The stabilizing buffer may also be or include a metal chelating reagent, such as ethylenediaminetetracetic acid disodium salt, or it may also contain a phosphate or citrate-phosphate buffer, or any other buffer.

A mild surfactant can be included in a therapeutic or pharmaceutical composition for use in the methods in an amount effective to potentiate the therapeutic effect of the lytic enzyme/polypeptide(s) may be used in a composition. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

The therapeutic composition of use in the present methods and applications may further comprise other enzymes, such as the enzyme lysostaphin for the treatment of any *Staphylococcus aureus* bacteria present along with the susceptible gram-positive bacteria. Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393-400 (1965)). The gene for lysostaphin has subsequently been cloned and sequenced (Recsei et al., Proc. Natl. Acad. Sci. USA, 84: 1127-1131 (1987). A therapeutic composition may also include mutanolysin, and lysozyme.

Means of application of the therapeutic composition comprising a lytic enzyme/polypeptide(s) in accordance with the present methods include, but are not limited to direct, indirect, carrier and special means or any combination of means. Direct application of the lytic enzyme/polypeptide(s) may be by any suitable means to directly bring the polypeptide in contact with the site of biofilm, infection or bacterial colonization, such as to the nasal area (for example nasal sprays), dermal or skin applications (for example topical ointments or formulations), suppositories, tampon applications, etc. Nasal applications include for instance nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application. The forms in which the lytic enzyme may be administered include but are not limited to lozenges, troches, candies, injectants, chewing gums, tablets, powders, sprays, liquids, ointments, and aerosols.

The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of infected skin. The carriers of topical compositions may comprise semi-solid and gel-like vehicles that include a polymer thickener, water, preservatives, active surfactants or emulsifiers, antioxidants, sun screens, and a solvent or mixed solvent system Polymer thickeners that may be used include those known to one skilled in the art, such as hydrophilic and hydroalcoholic gelling agents frequently used in the cosmetic and pharmaceutical industries. Other preferred gelling polymers include hydroxyethylcellulose, cellulose gum, MVE/MA decadiene crosspolymer, PVM/MA copolymer, or a combination thereof.

It may be advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention. Other approaches involving mucoadhesives which are the combination of hydrophilic and hydrophobic materials, are known. Micelles and multilamillar micelles may also be used to control the release of enzyme. Materials having capacity to target or adhere to surfaces, such as plastic, membranes, devices utilized in clinical practice, including particularly any material or component which is placed in the body and susceptible to bacterial adhesion or biofilm development, such as catheters, valves, prosthetic devices, drug or compound pumps, stents, orthopedic materials, etc, may be combined, mixed, or fused to the lysin(s) of use in the present invention.

Therapeutic or pharmaceutical compositions of use in the method can also contain polymeric mucoadhesives including a graft copolymer comprising a hydrophilic main chain and hydrophobic graft chains for controlled release of biologically active agents. The compositions of this application may optionally contain other polymeric materials, such as poly(acrylic acid), poly,-(vinyl pyrrolidone), and sodium carboxymethyl cellulose plasticizers, and other pharmaceutically acceptable excipients in amounts that do not cause deleterious effect upon mucoadhesivity of the composition.

A lytic enzyme/polypeptide(s) of the invention may be administered for use in accordance with the invention by any pharmaceutically applicable or acceptable means including topically, orally or parenterally. For example, the lytic enzyme/polypeptide(s) can be administered intramuscularly, intrathecally, subdermally, subcutaneously, or intravenously to treat infections by gram-positive bacteria. In cases where parenteral injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The effective dosage rates or amounts of the lytic enzyme/polypeptide(s) to be administered, and the duration of treatment will depend in part on the seriousness of the infection, the weight of the patient, particularly human, the duration of exposure of the recipient to the infectious bacteria, the number of square centimeters of skin or tissue or surface which are infected, the depth of the infection, the seriousness of the infection, and a variety of a number of other variables. The composition may be applied anywhere from once to several times a day, week, month, and may be applied for a short, such as days or up to several weeks, or long term period, such as many weeks or up to months. The usage may last for days or weeks or longer. Any dosage form employed should provide for a minimum number of units for a minimum amount of time. The concentration of the active units of enzymes believed to provide for an effective amount or dosage of enzymes may be selected as appropriate.

The lysin may be administered in a single dose or multiple doses, singly or in combination with another agent, such as one or more antibiotic. The lysin, optionally with another agent, such as antibiotic, may be administered by the same mode of administration or by different modes of administration. The lysin may be administered once, twice or multiple times, one or more in combination or individually. Thus, lysin may be administered in an initial dose followed by a subsequent dose or doses, particularly depending on the response and bacterial killing or decolonization or the dispersion of the biofilm or killing of bacteria in the biofilm, and may be combined or alternated with antibiotic dose(s). In a particular aspect of the invention a lysin, particularly PlySs2, or combinations of antibiotic and lysin may be administered for longer periods and dosing can be extended without risk of resistance.

The term 'agent' means any molecule, including polypeptides, antibodies, polynucleotides, chemical compounds and small molecules. In particular the term agent includes compounds such as test compounds, added additional compound(s), or lysin enzyme compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, polypeptide, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

It is noted that in the context of treatment methods which are carried out in vivo or medical and clinical treatment methods in accordance with the present application and claims, the term subject, patient or individual is intended to refer to a human.

The terms "gram-positive bacteria", "Gram-positive bacteria", "gram-positive" and any variants not specifically listed, may be used herein interchangeably, and as used throughout the present application and claims refer to Gram-positive bacteria which are known and/or can be identified by the presence of certain cell wall and/or cell membrane characteristics and/or by staining with Gram stain. Gram positive bacteria are known and can readily be identified and may be selected from but are not limited to the genera *Listeria, Staphylococcus, Streptococcus, Enterococcus, Mycobacterium, Corynebacterium,* and *Clostridium,* and include any and all recognized or unrecognized species or strains thereof. In an aspect of the invention, the PlyS lysin sensitive gram-positive bacteria include bacteria selected from one or more of *Listeria, Staphylococcus, Streptococcus,* and *Enterococcus.*

The term "bacteriocidal" refers to capable of killing bacterial cells.

The term "bacteriostatic" refers to capable of inhibiting bacterial growth, including inhibiting growing bacterial cells.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

The invention provides methods for the prevention, dispersion, treatment and/or decolonization of bacterial biofilms and the prevention of infections after dispersion of biofilm(s) wherein one or more gram positive bacteria, particularly one or more of *Staphylococcus, Streptococcus, Enterococcus* and *Listeria* bacteria, is suspected or present, comprising administering lysin, particularly PlySs2 lysin, having capability to kill *S. aureus* bacteria including MRSA. The invention provides methods for reducing or preventing biofilm growth on the surface of devices, implants, separation membranes (for example, pervaporation, dialysis, reverse osmosis, ultrafiltration, and microfiltration membranes) comprising administering or utilizing lysin, particularly PlySs2 lysin, having capability to kill *S. aureus* bacteria including MRSA.

The invention provides a method for treating a catheter-associated urinary tract infection (CAUTI), wherein the infection is attributed to biofilm-associated bacteria, by administering a composition comprising PlySs2 lysin. The invention provides compositions comprising PlySs2 lysin for use in treating a catheter-associated urinary tract infection (CAUTI), wherein the infection is attributed to biofilm-associated bacteria. The methods or compositions comprise PlySs2 lysin, including the polypeptide as provided in FIG. 5 or SEQ ID NO: 1 or variants thereof capable of killing Staphylococcal and Streptococcal bacteria, including *S. aureus*. The methods or compositions may additionally comprise one or more antibiotic.

Endocarditis, including Staphylococcal endocarditis in the heart, such as in an aortic valve or other valve or stent or device implanted in the heart or vessels thereof, is a significant clinical concern, risk and reality for many heart patients. The invention provides a method for reducing, preventing, dispersing or treating endocarditis, including Staphylococcal endocarditis, and for prevention or treatment of biofilm(s) on heart valves or vascular stents. In these methods lysin, particularly PlySs2 lysin or active variants thereof as provided herein, is administered to prevent or treat Staphylococcal endocarditis or biofilm(s) on heart valves or vascular stents.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

PlySs2 lysin demonstrates the ability to kill various strains of clinically significant gram positive bacteria, including methicillin and vancomycin resistant and sensitive strains of *Staphylococcus aureus* (MRSA, MSSA, VRSA and VISA). PlySs2 is a unique lysin in having broad species killing activity and can kill multiple species of bacteria, particularly gram-positive bacteria, significantly various antibiotic-sensitive and antibiotic-resistant *Staphylococcus*, and also *Streptococcus*, including Group A and Group B streptococcus. Other PlySs2 sensitive bacteria include *Enterococcus* and *Listeria* bacterial strains. A tabulation of sensitivity of various bacteria, including staphylococci and streptococci, to PlySs2 lysin is provided above including in TABLES 2 and 3.

A tabulation of additional MIC studies is shown below in TABLE 4.

TABLE 4

PlySs2 and antibiotic activity against *S. aureus* strains*

| Organisms (#of strains) | PlySs2 MIC$_{90}$ | [uM] | Daptomycin MIC$_{90}$ | [uM] | Vancomycin MIC$_{90}$ | [uM] | Oxacillin MIC$_{50/90}$ | [uM] | Linezolid MIC$_{50/90}$ | [uM] |
|---|---|---|---|---|---|---|---|---|---|---|
| MRSA (n = 45) | 4 | 0.15 | 1 | 0.6 | 1 | 0.7 | >4* | >10.0 | 2 | 5.7 |
| MSSA (n-28) | 4 | 0.15 | 1 | 0.6 | 1 | 0.7 | n/a | n/a | 2 | 5.7 |
| VISA (n = 10) | 32 | 1.2 | 8 | 4.9 | 4 | 2.7 | n/a | n/a | 2 | 5.7 |
| VRSA (n = 14) | 2 | 0.08 | 1 | 0.6 | >16 | >10.6 | n/a | n/a | 2 | 5.7 |
| LRSA (n = 5) | 2 | 0.08 | 1 | 0.6 | 1 | 0.7 | n/a | n/a | >64 | >183 |
| DRSA (n = 8) | 4 | 0.15 | 16 | 9.9 | 1 | 0.7 | n/a | n/a | 2 | 5.7 |

*MICs were determined using the broth microdilution method and evaluating 80% growth inhibition according to CLSI methods (M07-A9).
*Red/Bold = drug failure (MIC value is above EUCAST breakpoint for the indicated drug on *S. aureus*)

Notably and uniquely, despite activity against numerous clinically significant bacteria, including numerous *Staphylococcus* and *Streptococcus* strains and others tested as indicated in the above Tables, PlySs2 displays at most only minimal effects on other bacteria, particularly natural or commensal bacterial flora. TABLE 5 below demonstrates little lytic activity of PlySs2 against various commensal human gut bacteria.

TABLE 5

Sensitivity of Gut Bacteria to PlySs2

| Organism | N (# tested) | CF-301 MIC (ug/ml) |
| --- | --- | --- |
| Salmonella enteriditis | 1 | >512 |
| Pseudomonas aeruginosa | 11 | >512 |
| Escherichia coli | 10 | >512 |
| Klebsiella spp. | 8 | >512 |
| Proteus mirabilis | 2 | >512 |
| Lactobacillus spp. | 6 | >512 |
| Lactococcus spp. | 3 | >512 |

Biofilm formation is a key feature in the pathogenesis of many bacterial infections (31). Within infected tissues (i.e. heart valves in endocarditis or bone in osteomyelitis) or on implants (i.e. replacement joints and catheters), bacterial pathogens such as S. aureus exist in biofilms providing a favorable environment for growth and persistence, protected from the action of antibiotics and the immune system (32). The studies provided herein now demonstrate the potent anti-biofilm activity of PlySs2 lysin at only a 1×MIC concentration, in comparison to the complete inactivity of antibiotics used at 1000×MIC concentrations. This potent lysin anti-biofilm activity provides a means and compositions which are effective against biofilms and will uniquely complement the action of antibiotics by enabling access to lysin disrupted biofilms.

In view of PlySs2's rapid bacterial killing and effects on numerous clinically significant bacterial strains and species, the efficacy of PlySs2 lysin against Staphylococcus aureus biofilms was tested in vitro using biofilm assays.

Minimally inhibitory concentration of PlySs2 lysin against methicillin resistant S. aureus MRSA strain ATCC BAA-42 was determined as 16 μg/ml. This value is the MIC determined in the presence of reducing agent (such as DTT or BMS) in the MIC assay. Reducing agent is added for the purpose of improving reproducibility between and among assays in determining MIC values. Biofilm studies are conducted without added reducing agent. The MIC value for BAA-42 in the absence of reducing agent is 32 μg/ml. The MIC value is consistent with other MRSA strains on average as noted in the tables provided above (see Tables 2 and 4). MICs were determined using the broth microdilution method in accordance with standards and as described in the Clinical and Laboratory Standards Institute (CLSI) document M07-A9 (Methods for dilutional antimicrobial sensitivity tests for bacteria that grow aerobically. Volume 32 (Wayne [PA]: Clinical and Laboratory Standards Institute [US], 2012).

Biofilms were generated using a variation of the method described by Wu et al (Wu J A et al (2003) Antimicrob Agents and Chemother 47(11):3407-3414). Briefly, 1×10$^6$ stationary phase cells of methicillin-resistant S. aureus (MRSA) strain ATCC BAA-42 were inoculated into 2 ml of tryptic-soy broth supplemented with 1% glucose and grown for 18 hours in 24-well tissue culture dishes at 37° C. without aeration. Planktonic cells (non-adherent bacteria) were removed by washing with 1×PBS and remaining bacteria (sessile, or biofilm bacteria) were then treated with the with PlySs2 lysin or with antibiotic (daptomycin, linezolid or vancomycin obtained from Sigma-Aldrich) at various concentrations for up to 24 hours. At the various time points (0 hours, 2 hours, 4 hours, up to 24 hours), the wells were washed with 1× PBS, fixed by air-drying at 37° C. for 15 minutes, and stained with 1 ml of 1% crystal violet solution (Sigma-Aldrich) To visualize remaining biofilm. The optical density of biofilms stained with crystal violet was also determined to provide a more quantitative comparison. An exemplary density study is provided in FIG. 7.

Figure 2:
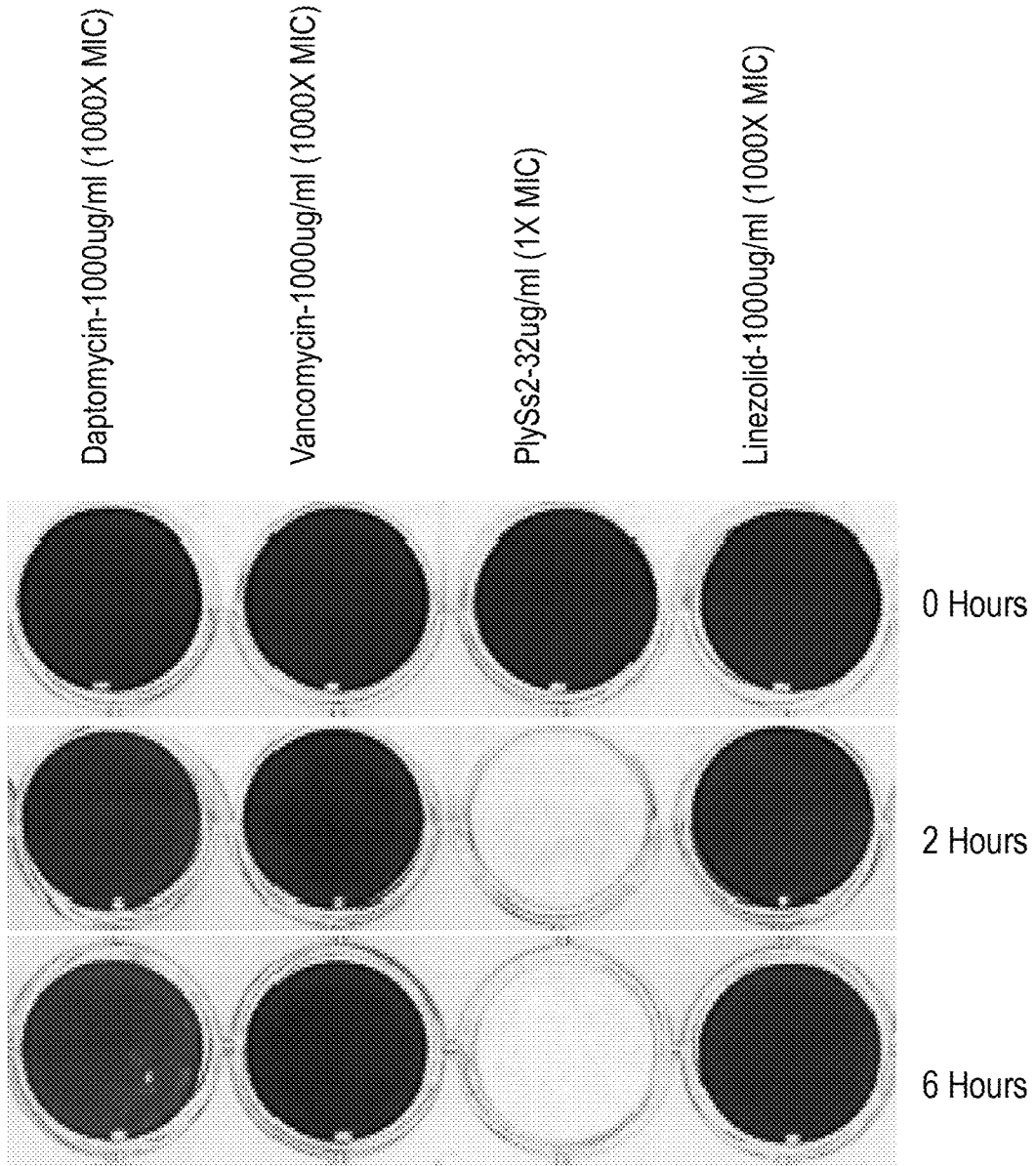
FIG. 2 depicts biofilms of BAA-42 MRSA treated with daptomycin, vancomycin, PlySs2 lysin or linezolid at the amounts and for the times indicated up to 6 hours. After treatment, biofilms are visualized with crystal violet.
Figure 3:
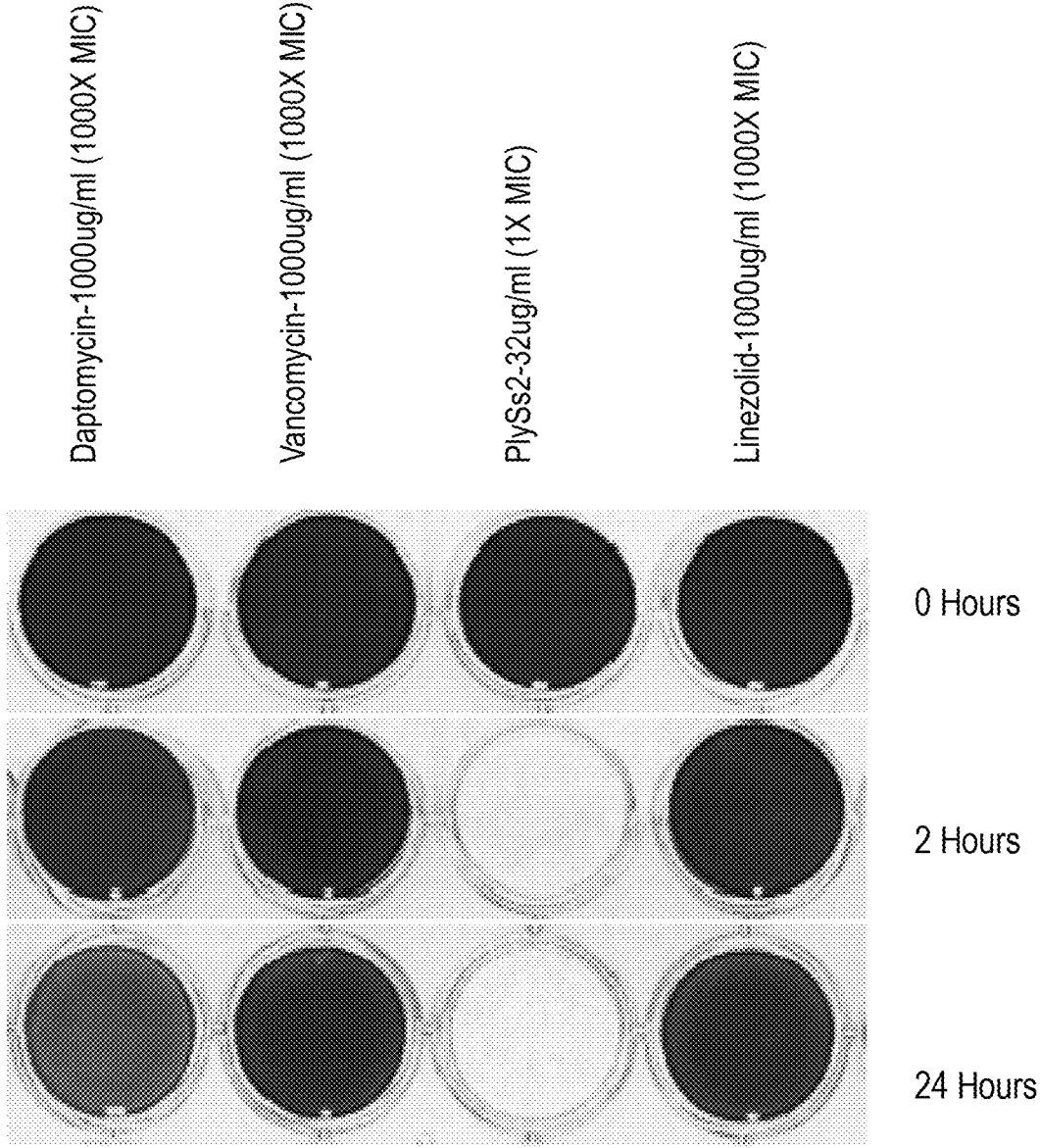
FIG. 3 depicts biofilms of BAA-42 MRSA treated with daptomycin, vancomycin, PlySs2 lysin or linezolid at the amounts and for the times indicated up to 24 hours. After treatment, biofilms are visualized with crystal violet.

In initial studies, biofilms of BAA-42 MRSA were treated with 1000×MIC concentrations (1000 μg/ml) for each of daptomycin, linezolid, and vancomycin and 1×MIC (32 μg/ml) for PlySs2 lysin (without added reducing agent). All MIC values were determined using the broth microdilution method described in the Clinical and Laboratory Standards Institute (CLSI) document M07-A9 (Methods for dilutional antimicrobial sensitivity tests for bacteria that grow aerobically. Volume 32. Wayne [PA]: Clinical and Laboratory Standards Institute [US], 2012). MRSA biofilms treated for up to 4 hours are shown in FIG. 1, up to 6 hours are shown in FIG. 2, and up to 24 hours shown in FIG. 3. The biofilm is cleared within 2 hours on treatment with PlySs2 lysin alone at 1×MIC 32 μg/ml (FIGS. 1, 2 and 3). No change in biofilm is evident visually in 4 hours or 6 hours on treatment with 1000 ug/ml (1000×MIC) of daptomycin, vancomycin, or linezolid (FIGS. 1 and 2). This is consistent with previous reports which have shown minimal sensitivity of biofilms to vancomycin at very high doses (10000 μg/ml) (Weigel L M et al (2007) Antimicrob Agents and Chemother 51(1):231-238).

Figure 4:
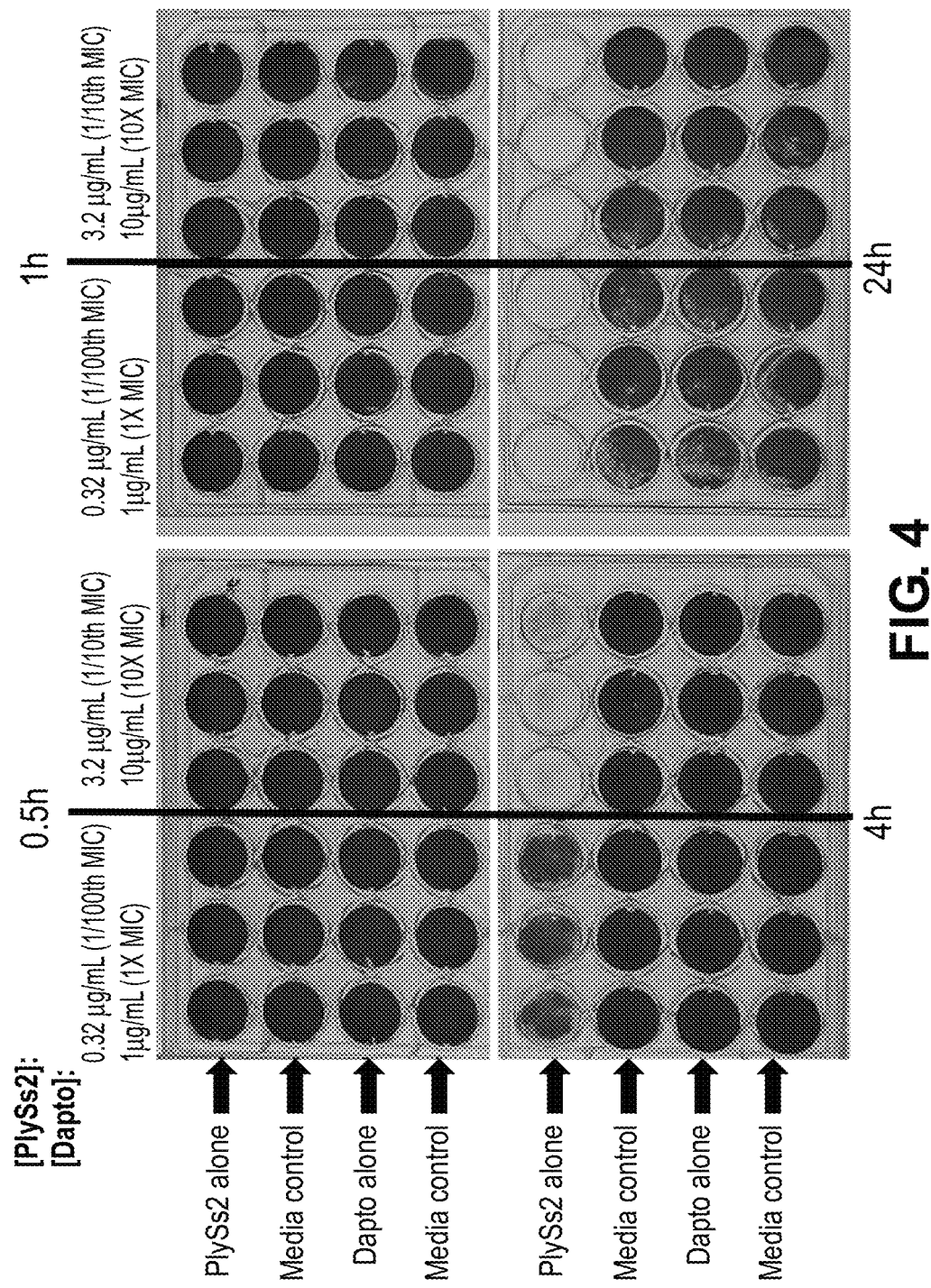
FIG. 4 depicts biofilms of BAA-42 MRSA in 24 well dishes treated with PlySs2 lysin or daptomycin for 0.5 hr, 1 hr, 4 hrs and 24 hrs at the indicated dosing amounts. After treatment, biofilms are visualized with crystal violet.

Lower concentrations of PlySs2 lysin and daptomycin treatment were evaluated against biofilms of MRSA strain BAA-42. Biofilms were treated with lower sub-MIC doses of PlySs2 for 0.5 hours, 1 hour, 4 hours and 24 hours. As described above, BAA-42 biofilms were generated in 24 well dishes and the wells were treated with either PlySs2 lysin or daptomycin antibiotic (with proper media controls). For PlySs2, sub-MIC doses of either 3.2 ug/mL (a 1/10×MIC value) or 0.32 ug/mL (a 1/100×MIC value) were used. For daptomycin, either 1 ug/mL (a 1×MIC value) or 10 ug/mL (a 10×MIC value) were used. The wells were incubated for up to 24 hours, washed, fixed and stained. The results are shown in FIG. 4. Even at 1/100$^{th}$ the MIC of PlySs2 lysin, biofilm dissolution is observed. Significant dissolution is demonstrated with PlySs2 lysin 3.2 μg/ml (1/10×MIC) at 4 hours, and even some dissolution is observed with 0.32 tag/ml (1/100×MIC) at 4 hours. With daptomycin concentrations up to 10×MIC, no dissolution is seen.

Figure 14:
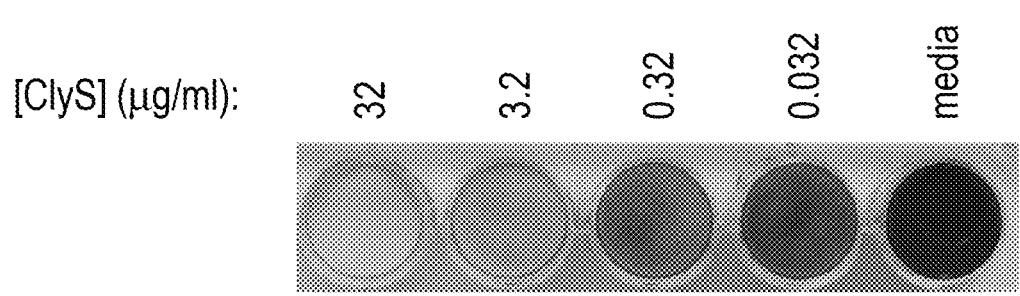
FIG. 14 depicts lysin ClyS activity against *S. aureus* biofilm. Biofilms of BAA-42 MRSA were treated with the indicated concentrations of ClyS lysin (1×MIC 32 ag/ml, 0.1×MIC 3.2 ag/ml, 0.01×MIC 0.32 ag/ml and 0.001×MIC 0.032 ag/ml) or media alone for 24 hours. Each well was washed and stained with 2% crystal violet.

Comparable MIC studies were completed using an alternative staphylococcal lysin, particularly ClyS lysin, against ATCC BAA-42 MRSA biofilms. The MIC of the ClyS lysin for this S. aureus strain is 32 μg/ml. Polystyrene tissue culture plates were inoculated with 5×10$^5$ CFUs of S. aureus strain ATCC BAA-42 per well (in Tryptic soy broth with 0.2% glucose) and incubated for 24 hours at 35° C. to allow biofilm formation. Resulting biofilms were washed 3 times to remove planktonic cells and treated with concentrations of ClyS lysin of 32 μg/ml, 3.2 μg/ml, 0.32 μg/ml and 0.032 μg/ml (or media alone) for 24 hours at 35° C. Each well was washed and stained with 2% crystal violet. Crystal violet stains the adherent biofilm material. The results using the various concentrations of ClyS are depicted in FIG. 14. ClyS effectively disperses the biofilm at 32 μg/ml (1×MIC) and 3.2 μg/ml (0.1× MIC). Reduction in stained biofilm is also observed at 0.32 μg/ml and somewhat at 0.032 μg/ml. The Staphylococcal lysin ClyS is capable of dispersing and reducing S. aureus biofilm.

Example 2

Combinations of daptomycin plus lysin at sub MIC doses are evaluated on biofilms. It has been found that PlySs2 lysin and daptomycin exert a synergistic lethal effect on planktonic S. aureus cells (U.S. Provisional Application Ser. Nos. 61/644,944 and 61/737,239). A series of experiments are undertaken to investigate whether this synergistic effect can also target bacteria in a biofilm. The broth microdilution checkerboard method (Sopirala M M et al. (2010) Antimicob Agents and Chemother 54(11):4678-4683) is applied to mature S. aureus biofilms grown in 96-well microtiter dishes. The activity of sub-MIC combinations of lysin and daptomycin is examined against 18 hour biofilms of MRSA strain ATCC BAA-42 grown in the manner described above with the exception that cells are grown in 0.2 ml suspensions. After biofilm formation, the wells are washed with 1×PBS and treated with PlySs2 and daptomycin alone or in a series of combinations for 24 hours without aeration. The biofilms are then washed, fixed and stained as above to evaluate biofilm formation. The effect of sub-MIC drug combinations is thus evaluated by comparison to the effects of either drug alone at those same sub-MIC concentrations.

Example 3

Mixed Biofilm Studies In Vitro

PlySs2 lysin is also used in combination with daptomycin to target multi-species biofilms. Biofilms often contain more than one bacterial species (Yang L et al (2011) FEMS Immunol and Med 62(3):339-347). PlySs2 lysin and daptomycin are utilized to target biofilms comprised of the PlySs2- and daptomycin-sensitive S. aureus strain ATCC BAA-42 and the PlySs2-resistant, daptomycin-sensitive Enterococcus faecalis strain. While E. faecalis strains are sensitive to daptomycin in planktonic form, they are nonetheless resistant to daptomycin as a sessile member of a biofilm. Only when the enterococci are released from a biofilm may they become resistant to daptomycin. To test the ability of PlySs2 to mediate this release (and thus sensitize E. faecalis to daptomycin), the following experiment is conducted.

Biofilms are generated as described above in 24 well dishes using an initial inoculums of $1\times10^6$ staphylococci and $1\times10^6$ enterococci (each alone and together). Biofilms are washed with PBS and treated with PlySs2 and daptomycin alone and in combination (using a series of sub-MIC combinations) for 24 hours. After treatment, the biofilm wells are separated into two fractions, including the non-adherent (including both living and dead bacteria) and the adherent (biofilm forms). The non-adherent fraction is plated for viability to determine relative CFU counts for staphylococci and enterococci. The CFU counts generated are compared to CFU counts for those biofilms treated with buffer controls. At the same time, the remaining biofilms are disrupted by sonication and plated for viability. In this manner, it can be determine if PlySs2 mediates the release of E. faecalis from biofilms where it may be killed by the daptomycin.

Biofilms with lysin$^S$antibiotic$^S$, lysin$^S$antibiotic$^R$, lysin-$^R$antibiotic$^S$ combinations are also evaluated as noted below.
I. Staphylococcus/Enterococcus mixed biofilm—treatment with lysin plus antibiotic as described above.
II. S. aureus/S. epidermidis mixed biofilm, or just S. epidermidis biofilms are generated and evaluated. Experiments are also performed as above using biofilms formed from S. aureus and S. epidermidis bacteria.
III. Combination Staph+Strep bacteria biofilms, treatment with PlySs2 and dapto or other antibiotics.
Experiments are performed as above using biofilms formed from both S. aureus and S. pyogenes (or S. dysgalactiae). Since both S. pyogenes (Group A streptococcus) and S. dysgalactiae (Group B streptococcus) are sensitive to PlySs2, these experiments will not utilize daptomycin. Rather, PlySs2 lysin is evaluated alone to disrupt and kill organisms in a mixed biofilm consisting of staphylococci and streptococci.

Example 4

In Vivo Catheter-Based Biofilm Models

Staphylococcus aureus infections associated with indwelling devices can be very difficult to treat due to the recalcitrant nature of bacterial biofilms to conventional antibiotics, and generally require removal of infected devices such as catheters. Courses of antibiotics can be administered and may even appear to eliminate most of the device-associated bacteria, only to have a recurrence of infection within a few days. This is believed to result from residual persister staphylococci in the biofilm outgrowing, repopulating the biofilm and reseeding the infection at the device site or elsewhere (Darouiche R O (2004) N Engl J Med 350:1422-1429). Therefore, a treatment that would rapidly kill staphylococci in biofilms and also be effective on planktonic bacteria would be of great benefit. PlySs2 lysin is demonstrated in the prior examples to rapidly and effectively clear S. aureus biofilms in vitro. This study assesses the ability of PlySs2 lysin to eradicate established S. aureus biofilms on implanted catheters in vivo in mice.

A catheter-based model was evaluated using catheters situated subcutaneous in flank, intraperitoneal or intramuscular into the thigh (modified from Zhu Y et al (2007) Infect Immunol 75(9):4219-4226). This catheter-based murine model is used to assess the impact of PlySs2 on biofilm viability in vivo. Prior to implantation, biofilms are grown in vitro on segments of catheter tubing (PVC [polyvinyl chloride] containing DEHP [Di(2-ethylhexyl)phthalate] as a plasticizer; CareFusion SmartSite infusion set, #72023). The lumen of each 2 inch catheter is inoculated with 200 µl of Tryptic Soy Broth (TSB) supplemented with 0.25% glucose containing $2\times10^7$ CFU of S. aureus, and biofilms are grown for 72 hours at 37° C. Alternatively, catheters are cut into 2 mm segments and placed in 1.0 ml of inoculated TSB supplemented with 0.25% glucose, and catheter segments are passaged daily into fresh medium for three days prior to implantation. Anesthesia is induced in 6-8 week old Balb/c mice by intraperitoneal injection of 0.15 ml of 100 mg/kg ketamine and 10 mg/kg xylazine (Butler-Schein). Catheter segments are implanted subcutaneously in each flank of the mice, or alternatively into the intraperitoneal space or thigh muscle. Groups of 5-10 mice were implanted with biofilm. Mice are treated with an appropriate amount of PlySs2, antibiotic or vehicle, or combination of PlySs2+antibiotic 1-24 hours post implantation. All mice from each group were humanely sacrificed at 1-4 days post-infection. To quantify biofilm formation, infected catheters were removed immediately after sacrifice, gently washed three times in sterile PBS to remove non-adherent bacteria, and subsequently placed in 5 ml of sterile PBS. Adherent bacteria are removed from the catheters by sonication. The number of recovered bacteria is then quantified by serial dilution and plate counting on the appropriate selective media. Alternatively, washed catheters were stained by 15 minute incubation in Methylene Blue, washed two times in 5 ml of sterile PBS and visualized. Methylene Blue stain can then be quantified by destaining in 0.2 ml of 30% acetic acid at room temperature and the absorbance read at 600 nm. The extent of residual biofilm mass is expressed as the absorbance reading at 600 nm divided by the weight of the catheter segment ($OD_{600}$/gm).

Figure 15:
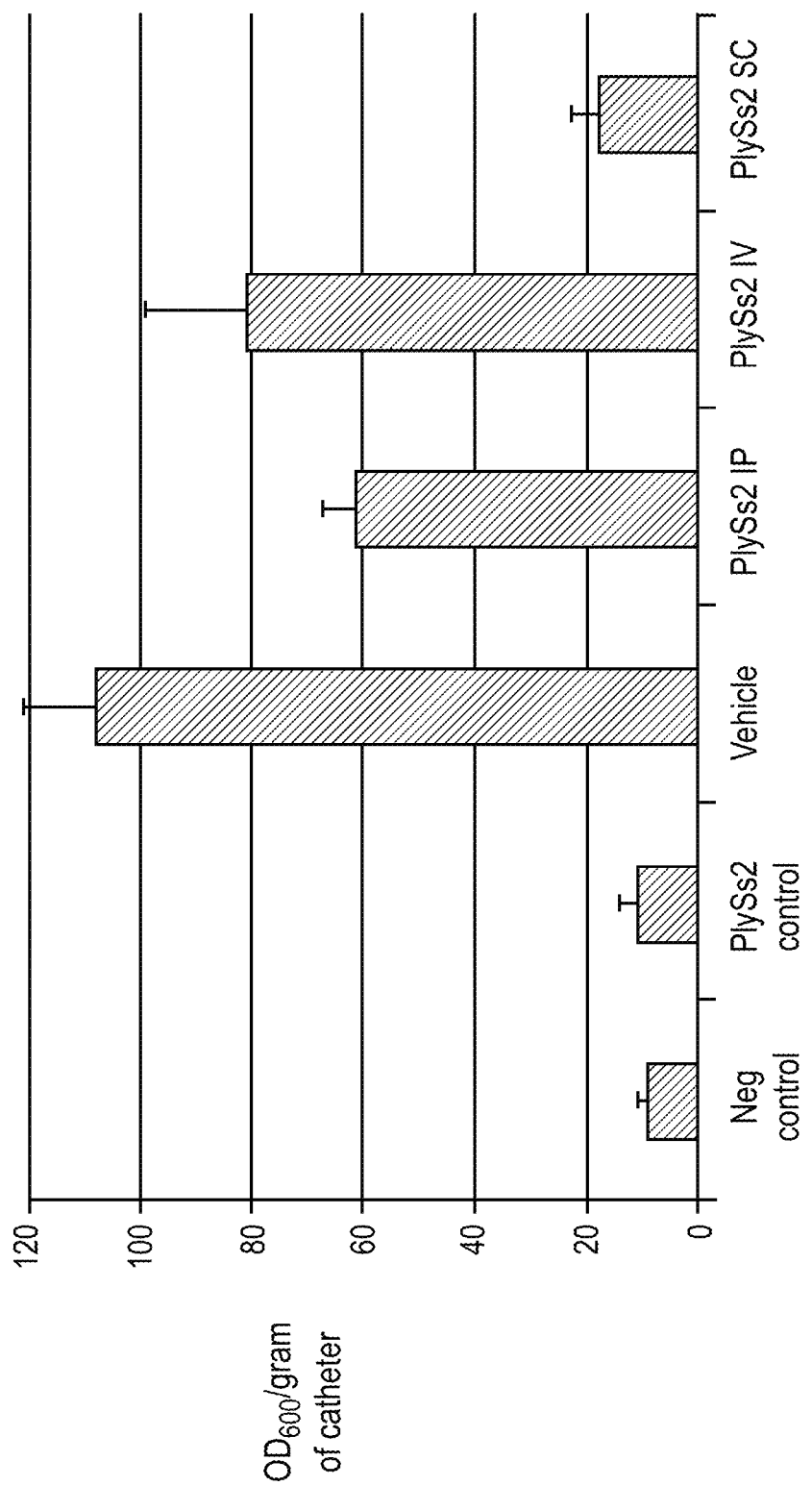
FIG. 15 provides the results of biofilm studies in vivo in mice with subcutaneous catheter implants treated with PlySs2 lysin by various modes of administration. Biofilms are grown on catheters, the catheter is implanted in mice, and the mice are treated. Catheters are removed, stained with methylene blue and staining quantified by absorbance at 600 nm. The OD at 600 nm/g of catheter is graphed for each of negative control (no bacteria), PlySs2 control (no bacteria mock treated), vehicle treated, PlySs2 administered intraperitoneally (IP), PlySs2 administered intravenously (IV), and PlySs2 administered subcutaneously (SC).

FIG. 15 provides the results of such a catheter study wherein catheters with *S. aureus* (MRSA strain ATCC BAA-42) biofilm grown for 3 days were implanted into subcutaneous space in mice and then treated at 24 hours post implant. Mice were each implanted with 2 catheters and 2 mice evaluated for each of the following conditions: negative control (no biofilm, no agent), PlySs2 control (no biofilm mock treated with PlySs2 agent), vehicle only, PlySs2 administered intraperitoneally (IP), PlySs2 administered intravenously (IV), and PlySs2 administered subcutaneously (SC). PlySs2 was administered as a single bolus of 100 μg (corresponding to 5 mg/kg in the mouse and ~50 μg/ml dose). Catheters were removed 6 hrs post treatment and stained with methylene blue. The relative amount of staining (visualized at 600 nm) under each condition is presented in FIG. 15. Each of the IP, IV and SC doses reduced staining, with the subcutaneous bolus resulting in elimination of staining in the catheter to near control levels.

Example 5

In another set of experiments, implanted jugular vein catheters in mice are pre-instilled with PlySs2 lysin to assess protection of mice from biofilm infection with this pre-treatment. Using the jugular catheter animal model described above, the catheters of jugular vein catheterized mice are pre-treated with instillation of PlySs2 lysin in PBS 24 h prior to the *S. aureus* challenge. Control animals receive catheters pre-treated with PBS alone. On the day of the challenge, 2 h prior to the challenge, all catheters are flushed with PBS to remove excess unbound lysin, and then the mice are challenged with *S. aureus* via the tail vein as described above. The challenged animals were sacrificed at various days after the bacterial challenge and the catheters and organs recovered and bacteria quantified as described above.

Example 6

Staphylococcal endocarditis is a biofilm based infection that can be experimentally induced in the aortic valve of rats (Entenza J M et al (2005) IAI 73:990-998). Briefly, sterile aortic vegetations are produced in rats and infusion pumps to deliver lysin are installed as described (Entenza et al). Endocarditis is induced 24 h later by i.v. challenge with $10^5$-$10^7$ staphylococci. At either 24 or 48 hours after infection, lysin and/or antibiotics such as daptomycin, vancomycin, or linezolid are administered intravenously. Control rats receive buffer alone. At various time points after infection up to 72 hours, animals are sacrificed and quantitative blood and vegetation cultures were performed. Bacterial densities are expressed as log; CFU per mL or gram of tissue, respectively.

Example 7

Figure 6:
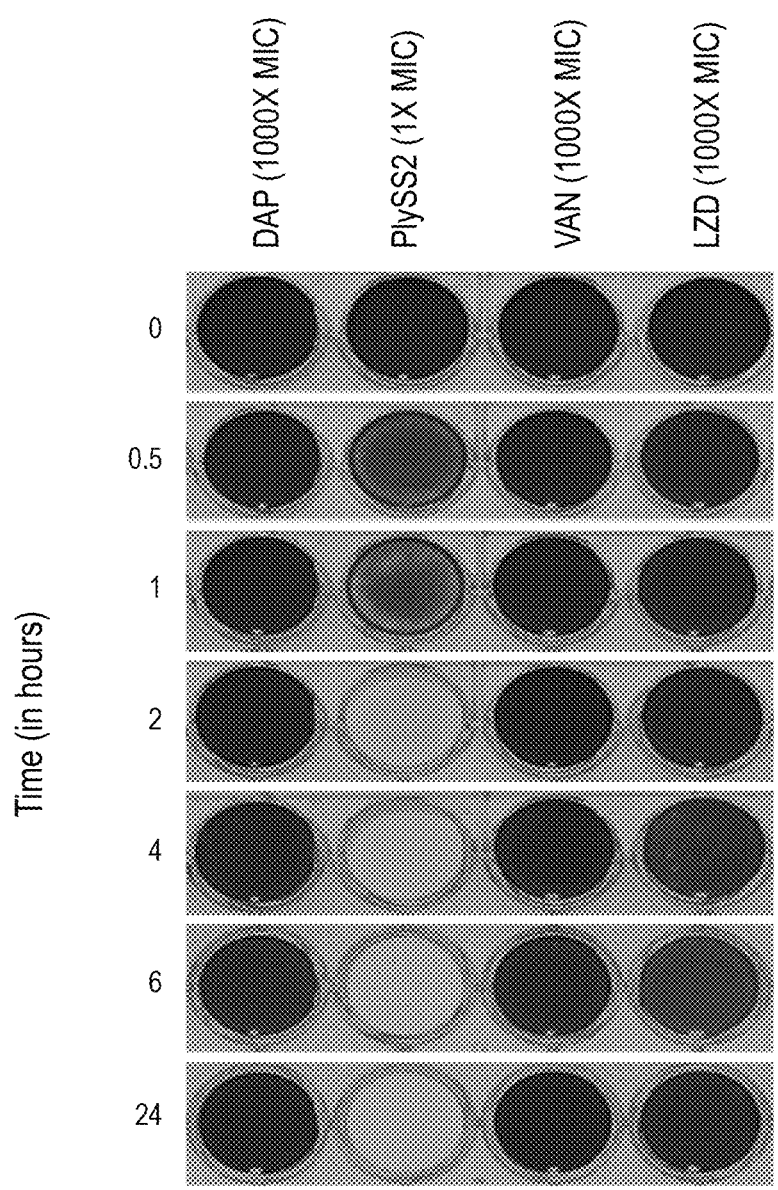
FIG. 6 provides a twenty-four hour time course analysis of PlySs2 and antibiotic activity on MRSA biofilms as assessed by crystal violet staining. Antibiotics daptomycin (DAP), vancomycin (VAN) and linezolid (LZD) were added at 1000×MIC for each antibiotic. PlySs2 was added at 1×MIC.
Figure 7:
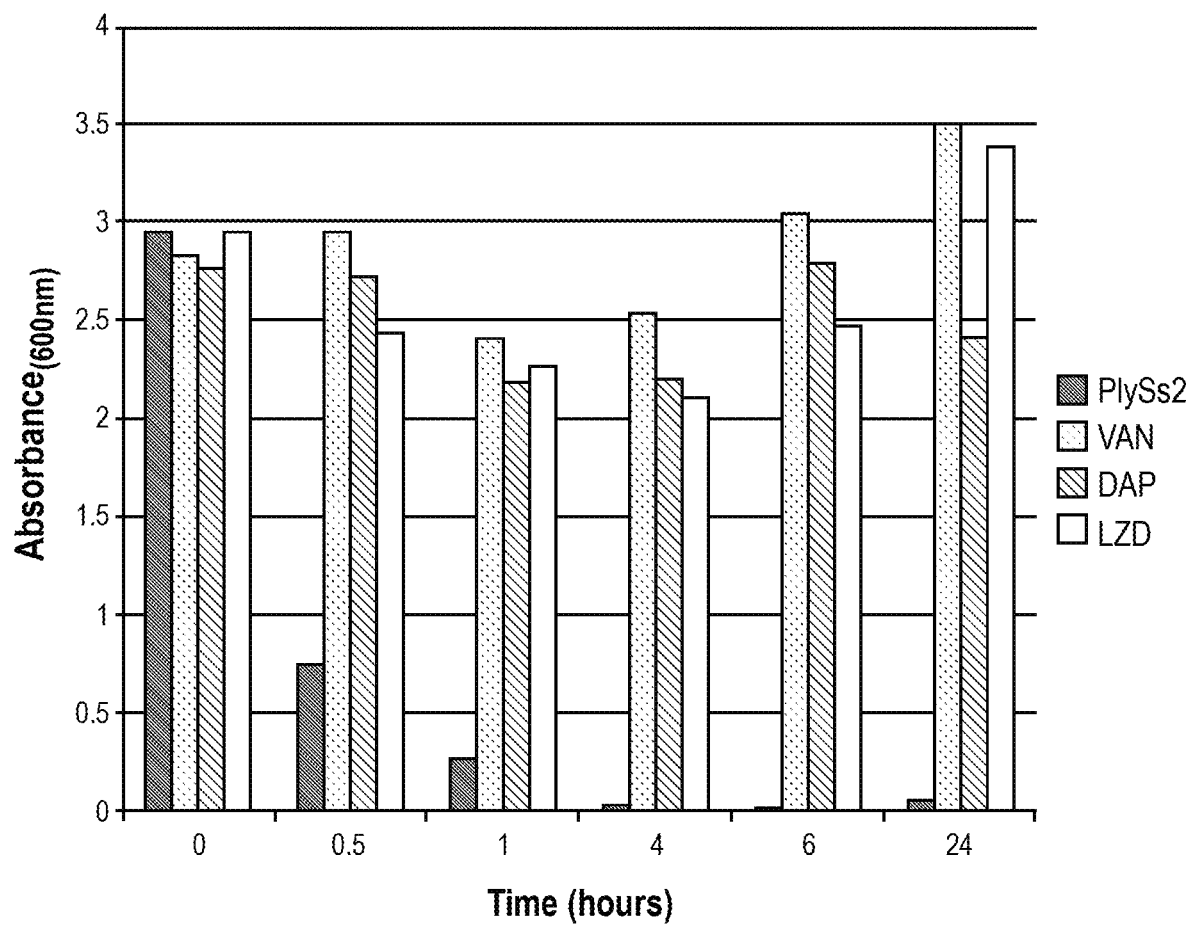
FIG. 7 depicts quantitation of dye retained as an indicator of biofilm retained in a twenty-four hour time course analysis of PlySs2 and antibiotic activity on MRSA biofilms. Antibiotics daptomycin (DAP), vancomycin (VAN) and linezolid (LZD) were added at 1000×MIC for each antibiotic. PlySs2 lysin was added at 1×MIC.

In order to compare relative biofilm eradication activities of PlySs2 and standard-of-care antibiotics, a twenty-four hour time course analysis of PlySs2 and antibiotic activity was performed on MRSA biofilms. Biofilms were generated in 24-well polystyrene plates by inoculating $10^5$ bacteria (MRSA strain ATCC BAA-42) into 0.5 ml Tryptic-soy broth with 0.2% glucose (TSB+) per well and incubated for 24 hours at 37° C. One plate was generated for each treatment time point to be assessed (0, 0.5, 1, 2, 4, 6 and 24 hours). After 24 hours, media was aspirated, wells were washed twice with 1×PBS, and the drug treatment was added and treatment time initiated. Indicated drug concentrations (1000×MIC for daptomycin, vancomycin or linezolid; 1×MIC for PlySs2 lysin) in 1 ml MHB2 (or MHB2 supplemented to 50 ug $CaCl_2$ per ml) were added to each well and incubated for the indicated time periods before aspiration, 2 washes with 1×PBS, and air drying for 15 minutes. Wells were stained with a 3% crystal violet solution in 1 ml for 5 min, then aspirated, washed 3 times with 1×PBS, air dried for 15 minutes, and photographed. All experiments were performed in duplicate. The results are shown in FIGS. 6 and 7. Crystal violet staining of the wells is shown in FIG. 6 and quantitation of the dye retained in the wells of the plate is shown in FIG. 7. PlySs2 at 1×MIC completely cleared the biofilm by 2 hours while daptomycin, vancomycin, and linezolid at 1000×MIC concentrations showed no biofilm clearance at 24 hours.

Figure 8:
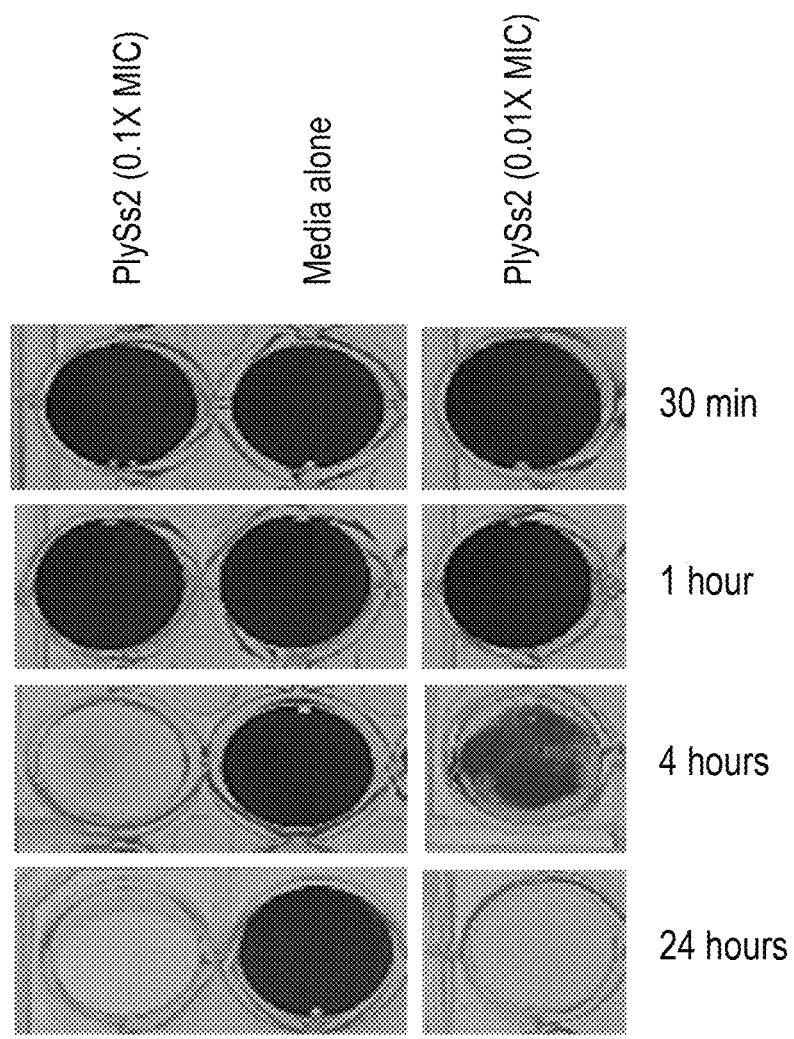
FIG. 8 shows a 24 hour time course of sub-MIC concentrations of PlySs2 versus media alone on MRSA biofilms as assessed by crystal violet staining. PlySs2 was added to MRSA strain BAA-42 biofilm at 0.1×MIC and 0.01×MIC levels.

In order to determine the ability of sub-MIC concentrations of PlySs2 to treat biofilms, a twenty-four hour time course analysis was performed. Biofilms were generated in 24-well polystyrene plates by inoculating $10^5$ bacteria (MRSA strain ATCC BAA-42) into 0.5 ml Tryptic-soy broth with 0.2% glucose (TSB+) per well and incubated for 24 hours at 37° C. One plate was generated for each treatment time point to be assessed (30 min, 1 hr, 4 hrs, 24 hrs). After 24 hours, media was aspirated, wells were washed twice with 1×PBS, and PlySs2 was added and treatment time initiated. Indicated PlySs2 concentrations (0.1×MIC and 0.01×MIC) in 1 ml MHB2, or media alone were added to each well and incubated for the indicated time periods before aspiration, 2 washes with 1×PBS, and air drying for 15 minutes. Wells were stained with a 3% crystal violet solution in 1 ml for 5 min and then aspirated, washed 3 times with 1×PBS, air dried for 15 minutes, and photographed. All experiments were performed in duplicate. The results are shown in FIG. 8. PlySs2 at 0.1×MIC cleared the biofilm by 4 hours. PlySs2 at 0.01×MIC yielded partial clearance at 4 hours while full clearance was observed by the 24 hour time point.

Example 8

The biofilm eradication activities were assessed for both PlySs2 and daptomycin against MRSA biofilms grown on catheters. Biofilms were generated in 2 inch segments of catheter tubing (PVC [polyvinyl chloride] containing DEHP [Di(2-ethylhexyl)phthalate] as a plasticizer; (CareFusion SmartSite infusion set, #72023) by inoculating $10^5$ bacteria (MRSA strain ATCC BAA-42) into 0.2 ml Tryptic-soy broth with 0.2% glucose (TSB+) per segment and incubated for 72 hours at 37° C. All samples were set up in duplicate for either staining with methylene blue or quantitation of CFUs. After 72 hours, media was flushed out, segments were washed with 1 ml of 1×PBS, and treatment was added. Indicated drug concentrations (1×MIC and 1000×MIC for daptomycin, 1×MIC for PlySs2) in 0.2 ml Lactated Ringer's solution were added to each segment and incubated for 24 hours before flushing, and washing with 1 ml 1×PBS. Duplicate samples were then examined as follows: To assess biofilm eradication, segments were stained with a 0.02% methylene blue solution (in water) in 0.22 ml for 15 min.

Segments were then flushed, washed 3 times with dH$_2$O, air dried for 15 minutes, and photographed. To quantitate the amount of live cells retained within the residual biofilms, duplicate segments were treated with 0.22 ml lysis buffer (100 ug/ml lysostaphin in Lactated Ringer's Solution) for 8 minutes. Next, 0.1 ml samples were removed, added to 96-well solid white polystyrene plate, and mixed with 0.1 ml of Promega BacTiter-Glo Luciferin/Luciferase reagent and relative light units (RLUs) were immediately measured (as specified by the kit manufacturer's instructions) and compared to a previously generated standard curve correlating RLU values to known concentrations of bacteria. In this manner, an estimation of bacterial CFUs in each biofilm was determined.

Figure 9A:
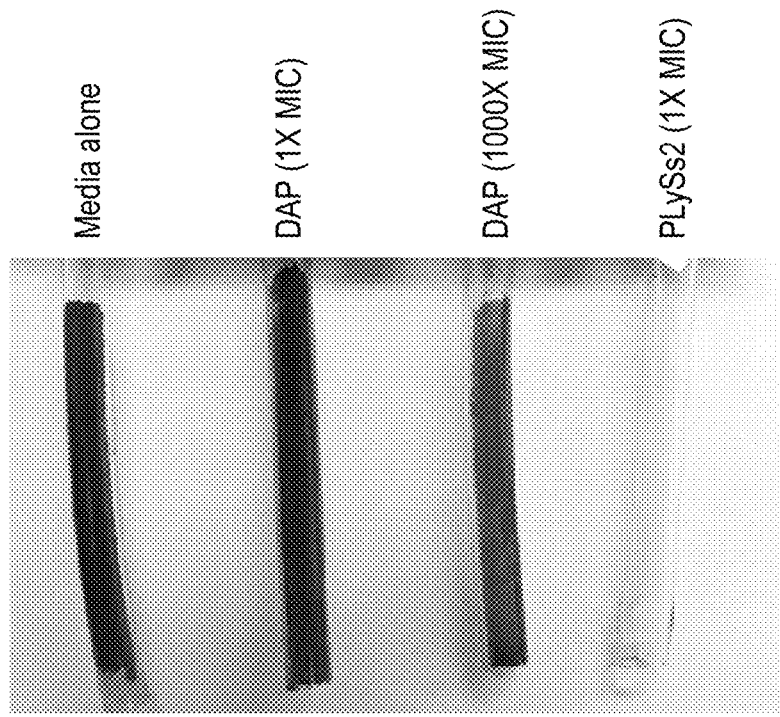
FIGS. 9A and 9B depict biofilm eradication studies against MRSA grown on DEPC catheters.
Figure 9B:
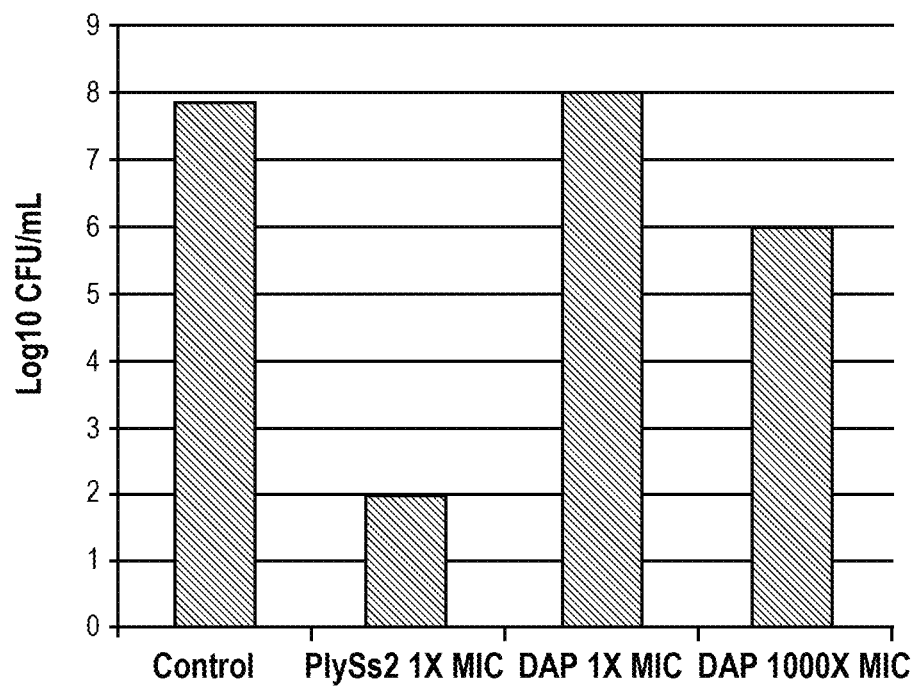

The results are shown in FIGS. 9A and 9B. Relative biofilm staining is shown in FIG. 9A. PlySs2 completely cleared the biofilm from the catheter at 1× MIC, while daptomycin did not remove significant biofilm even at 1000×MIC. As seen in FIG. 9B, PlySs2 at 1×MIC took the CFUs down to the 100 CFU/ml, which is the limit of detection, while no CFU reduction was seen with daptomycin at 1×MIC and a two log reduction from 100 million to 1 million CFU/ml was observed at 1000× MIC daptomycin.

Figure 10:
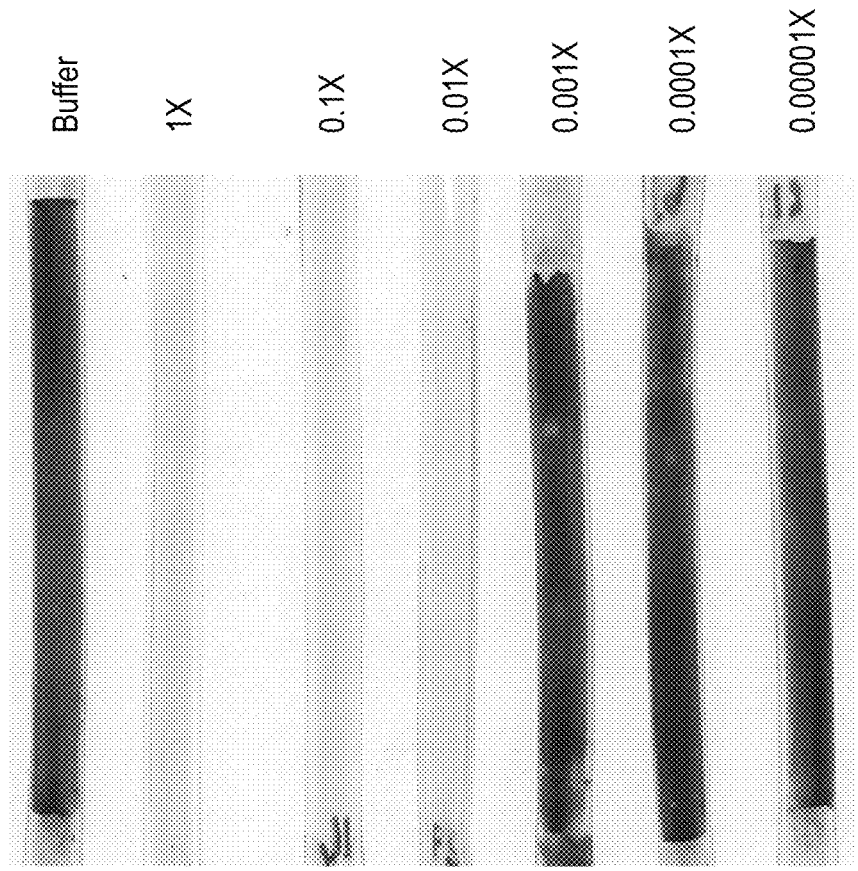
FIG. 10 depicts titration analysis of DEPC catheter MRSA biofilm staining with methylene blue after 4 hour treatment with buffer or titrated MICs of PlySs2 of 1×MIC, 0.1×MIC, 0.01×MIC, 0.001×MIC, 0.0001×MIC and 0.00001×MIC PlySs2.

To determine lowest amount of PlySs2 needed to eradicate biofilm from catheters, a titration experiment was performed (FIG. 10). Biofilms were generated in 2 cm segments of DEHP catheter tubing by inoculating 10$^5$ bacteria (MRSA strain ATCC BAA-42) into 0.2 ml Tryptic-soy broth with 0.2% glucose (TSB+) per segment and incubated for 72 hours at 37° C. After 72 hours, media was flushed out, segments were washed with 1 ml of 1×PBS, and drug treatment was added. Indicated drug concentration (1×, 0.1×, 0.01×, 0.001×, 0.0001× and 0.00001×MIC amounts of PlySs2) in 0.2 ml Lactated Ringer's solution were added to each segment and incubated for 24 hours before flushing, and washing with 1 ml 1×PBS. Segments were stained with a 0.02% methylene blue solution (in water) in 0.22 ml for 15 min, before being flushed, washed 3 times with dH20, air dried for 15 minutes, and photographed. The amount of PlySs2 need to fully eradicate the biofilm as determined by staining was 0.01×MIC (0.32 ug/ml) (FIG. 10). A similar titration analysis performed with daptomycin (1×, O1×, 100×, 1000×, 5000×MIC daptomycin) showed that concentrations of daptomycin as high as 5000×MIC (5 mg/ml) did not remove the biofilm (FIG. 11).

Figure 11:
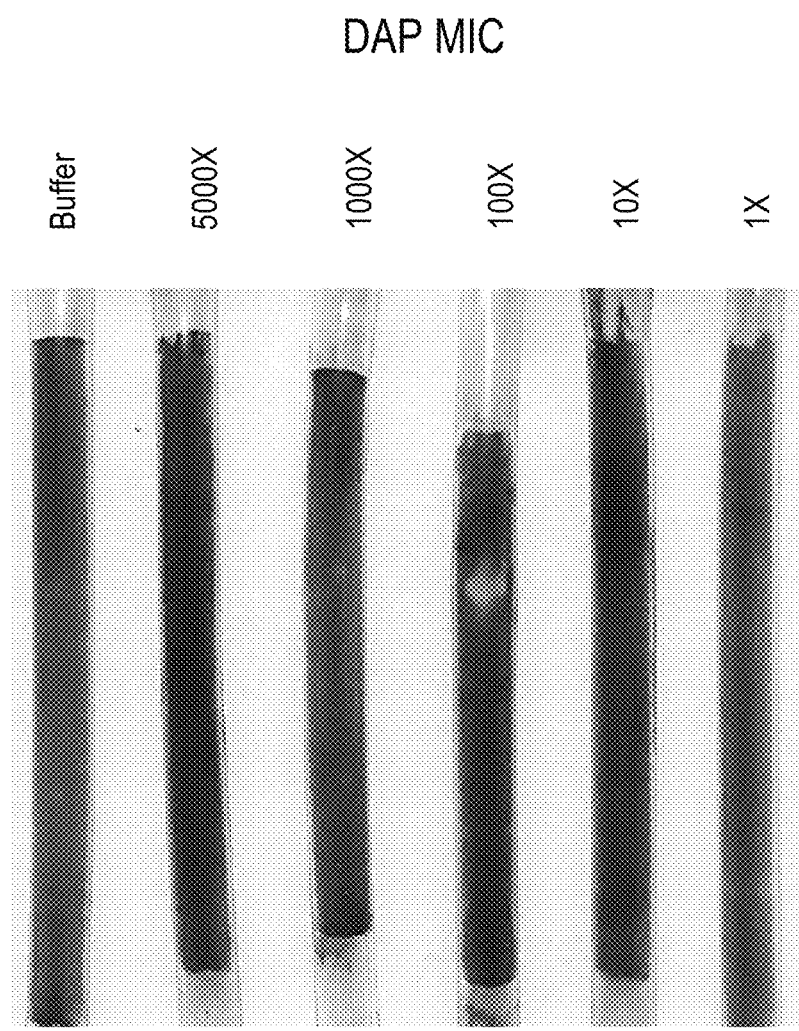
FIG. 11 depicts titration analysis of DEPC catheter MRSA biofilm staining with methylene blue after 4 hour treatment with buffer or titrated daptomycin (DAP) at 5000× MIC, 1000×MIC, 100×MIC, 10×MIC and 1×MIC.
Figure 13:
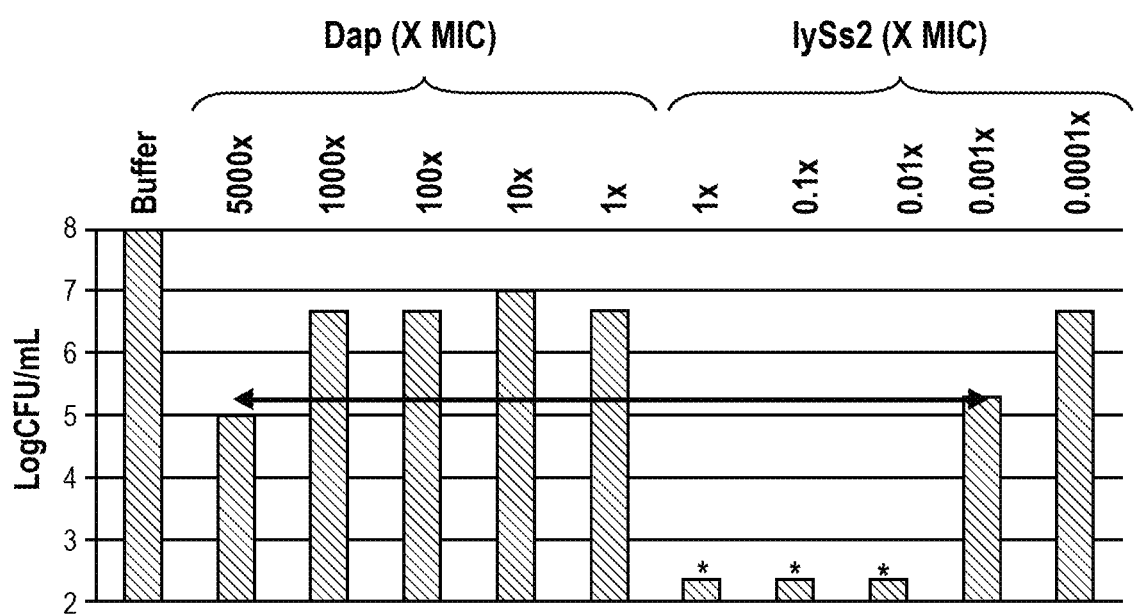
FIG. 13 depicts a titration analysis of DEPC catheter MRSA biofilm CFU counts after 4 hour treatments of cathether biofilms with the indicated drug concentrations in accordance with the studies shown in FIGS. 11 and 12. Bacterial CFUs remaining after drug treatments were estimated based on relative light units using a luciferase reagent calibrated against known concentrations of bacteria. Biofilms formed by *Staphylococcus aureus* strain ATCC BAA-42 on the lumens of di(2-ethylhexyl)phthalate (DEHP) catheters were treated for 4 hours with the indicated concentrations of PlySs2 or daptomycin (DAP). Lactated Ringer's solution alone was included as a control. After treatment, the catheters were drained and washed, and colony-forming units (CFU) were measured using an adenosine triphosphate (ATP) release-based method (BacTiter-Glo™ Microbial Cell Viability Assay kit). The red line indicates the concentrations of DAP at 5000× the minimum inhibitory concentration (MIC) and PlySs2 at 0.01×MIC that resulted In roughly equivalent decreases in biofilms in the treated catheter tubes. Key: *=Below the threshold of detection.

For quantitation of CFUs remaining after biofiolm treatment with lysin or antibiotic, duplicate segments as assessed in FIGS. 10 and 11 were treated with 0.22 ml lysis buffer (100 ug/ml lysostaphin in Lactated Ringer's Solution) for 8 minutes. Next, 0.1 ml samples were removed, added to 96-well solid white polystyrene plate, and mixed with 0.1 ml of Promega BacTiter-Glo Luciferin/Luciferase reagent and relative light units (RLUs) were immediately measured (as specified by the kit manufacturer's instructions) and compared to a previously generated standard curve correlating RLU value to known concentrations of bacteria. In this manner, an estimation of bacterial CFUs in each biofilm was determined. The titration analysis confirmed the results of methylene blue staining and is provided in FIG. 13. PlySs2 is active at removing biofilm bacteria down to a 0.01×MIC concentration while daptomycin is completely ineffective up to concentrations of 5000×MIC.

Figure 12A:
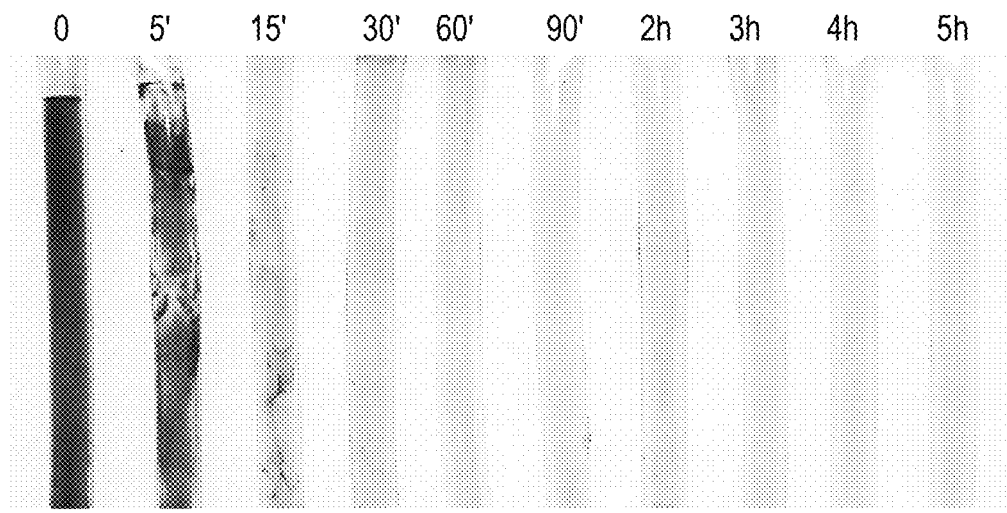
FIGS. 12A and 12B show a time course analysis of PlySs2 activity against MRSA biofilms in DEPC catheters.
Figure 12B:
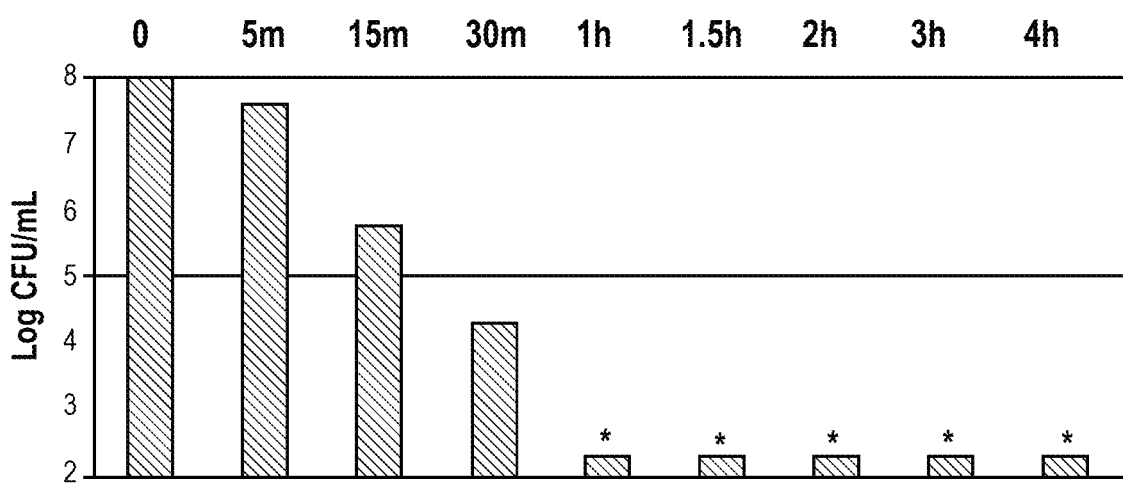

A time course analysis of PlySs2 activity against MRSA catheter biofilms was then performed (FIGS. 12A and 12B). Biofilms were generated in 2 inch segments of DEHP catheter tubing by inoculating 10$^5$ bacteria (MRSA strain ATCC BAA-42) into 0.2 ml Tryptic-soy broth with 0.2% glucose (TSB+) per segment and incubated for 72 hours at 37° C. Two samples were set up for each indicated time point (0 min, 5 min, 15 min, 30 min, 60 min, 90 min, 2 hrs, 3 hrs, 4 hrs, 5 hrs) to accommodate methylene blue staining and CFU quantitation. After 72 hours, media was flushed out, segments were washed with 1 ml of 1×PBS, and treatment was added. PlySs2 (1×MIC concentration, or 32 ug/mL) in 0.2 ml Lactated Ringer's solution were added to each segment and incubated for indicated time points before flushing, and washing with 1 ml 1×PBS. Duplicate samples were then examined at each time point as follows: segments were stained with a 0.02% methylene blue solution (in water) in 0.22 ml for 15 min. Segments were then flushed, washed 3 times with dH20, air dried for 15 minutes, and photographed. Duplicate segments were treated with 0.22 ml lysis buffer (100 ug/ml lysostaphin in Lactated Ringer's Solution) for 8 minutes. Next, 0.1 ml samples were removed, added to 96-well solid white polystyrene plate, and mixed with 0.1 ml of Promega BacTiter-Glo Luciferin/Luciferase reagent and relative light units (RLUs) were immediately measured (as specified by the kit manufacturer's instructions) and compared to a previously generated standard curve correlating RLU value to known concentrations of bacteria. In this manner, an estimation of bacterial CFUs in each biofilm was determined. The time course analysis revealed a progressive removal of stainable biofilm from the catheters at 1×MIC PlySs2 over time, with full removal by 60 minutes (S 12A). The CFU analysis revealed a similar progressive time course, with CFU values at the limit of detection (100 CFU/ml) by 60 minutes (FIG. 12B).

Example 9

To determine the stability of PlySs2 in a simulated catheter setting, PlySs2 was incubated at various concentrations in Lactated Ringer's solution at 37° C. After 7 days, the lytic activity of PlySs2 was assessed by adding 1×10$^5$ staphylococci, incubating for 4 hours, then treating with proteinase K to remove residual PlySs2, and serial dilution and plating for viability. The resulting CFU value for each condition was divided by 1×10$^5$ to determine the % Loss of Activity.

The results are tabulated below in TABLE 6. After a 7 day incubation in Lactated Ringer's solution at 37° C., undetectable activity losses were observed for the 10× and 100×MIC concentrations of PlySs2, while a 58.3% loss was determined for the 1×MIC sample.

TABLE 6

| PlySs2 Stability at 37° C. in Lactated Ringer's Solution | |
|---|---|
| TREATMENT | % LOSS OF ACTIVITY (7 days) |
| 1X MIC | 58.3 |
| 10X MIC | <0.002 |
| 100X MIC | <0.002 |

The above indicates that PlySs2 is active and stable at least up to 7 days in a simulated catheter setting and can effectively kill Staphylococci and thereby prevent bacterial colonization even after an extended period of time incubating in Lactated Ringer's, an exemplary standard care IV and flush solution.

Example 10

Figure 16:
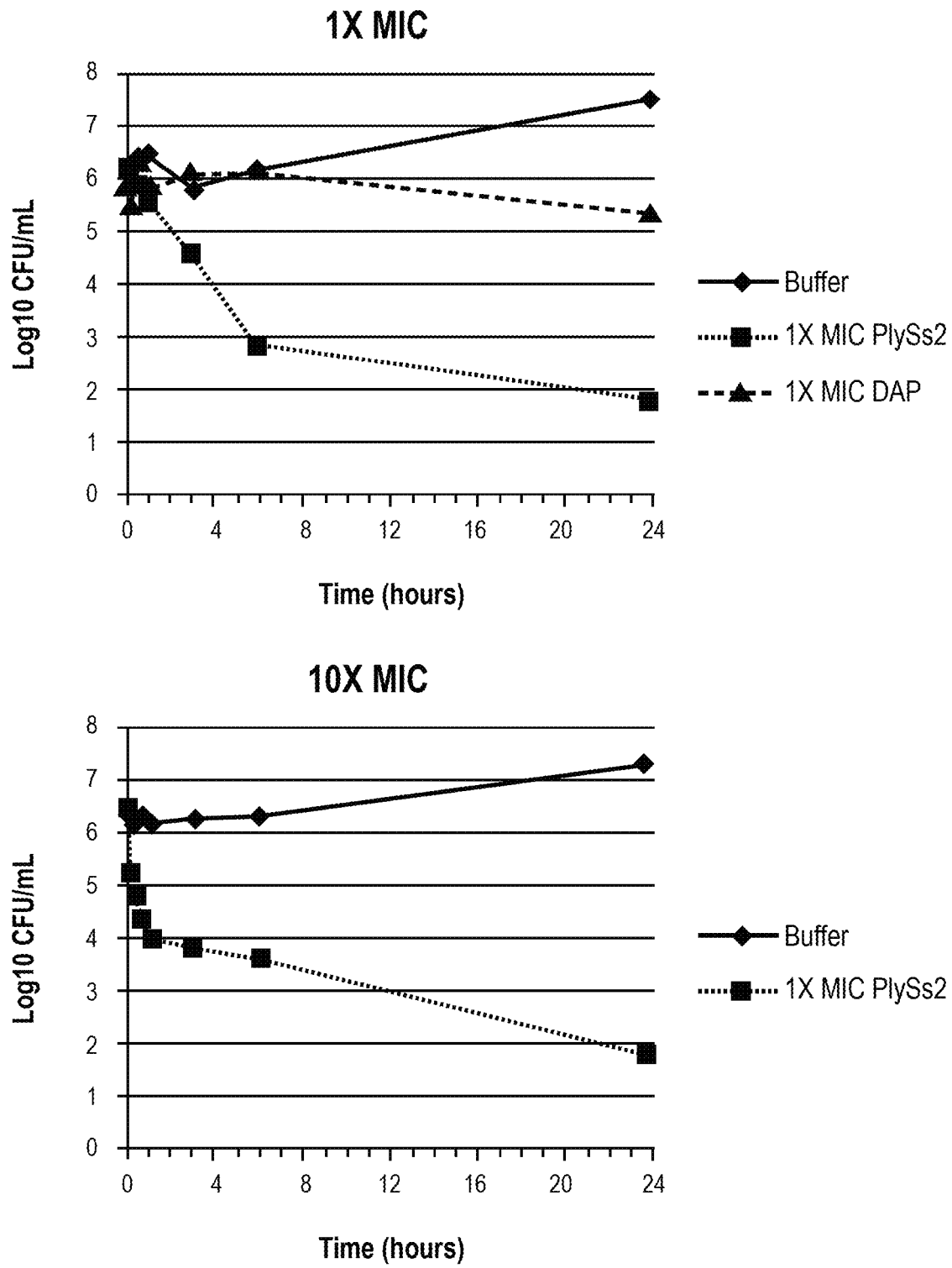
FIG. 16 depicts time course studies evaluating the luminal contents of MRSA catheter biofilms treated with PlySS2 lysin or daptomycin and assessing for bacterial viability and luminal sterilization over time with treatment of PlySs2 or antibiotic daptomycin.

A time course study was conducted to evaluate luminal sterilization in a catheter to assess the viability of bacteria that are dislodged from the biofilm and are suspended in the liquid phase of the lumen after or upon lysin treatment. In FIGS. 12A and 12B described above, it was demonstrated that the biofilm (adherent to the walls) is lost and fully dispersed by 1 hour. In the present study, sterilization (complete kill) of bacteria in the lumen, as evaluated by CFU analysis which detects live cells, occurs approximately between 6 and 24 hours. Biofilms were formed with strain ATCC BAA-42 for 3 days at 37° C. Biofilms were washed with 1×PBS (to remove planktonic cells) and treated with either lactated ringer's solution (buffer control) or lactated ringer's solution containing PlySs2 lysin (at a 1×MIC concentration) or daptomycin (at a 1×MIC concentration) and also with PlySs2 lysin (at a 10×MIC concentration). Biofilms were treated for up to 24 hours and CFUs evaluated at 2 minutes, 15 minutes, 30 minutes, 1 hour, 2 hrs, 6 hrs and 24 hours. At each time point, the lumenal contents of the catheters were removed and plated for viability. FIG. 16 provides the results for 1×MIC (32 µg/ml), 1×MIC daptomycin, and 10×MIC (320 µg/ml) level treatments versus buffer alone.

Example 11

Lysin was evaluated for effectiveness against *Staphylococcus epidermidis* biofilms. Biofilms of various *S. epidermidis* strains were generated in polystyrene 24-well microtiter plates and treated with PlySS2 lysin to determine the minimal inhibitory concentration (MIC) and biofilm eradicating concentration (BEC) of PlySs2 against each strain. The results are tabulated below in TABLE 7 against over twenty distinct *S. epidermidis* strains. The MIC (in micrograms/ml) was determined and calculated using standard CLSI method for broth microdilution as described and referenced in the Examples above. The biofilm eradicating concentration (BEC) of PlySs2 (in micrograms/ml) is the lowest concentration of a dilution range that completely destroys a 24 hour biofilm of the indicated strains.

To determine BEC, 24 h biofilms were grown in 24 well plates, washed 2× with PBS, and treated with or without PlySs2 (dilution range) prepared in Lactated Ringers Solution. The treated plates were incubated at 37° C. (ambient air) for 24 hours, washed with PBS and stained with Crystal Violet (CV) for 15 minutes. The CV stain was next solubilzed with 1 mL of 33%

TABLE 7

| CFS | Type | Designation | MIC | BEC |
| --- | --- | --- | --- | --- |
| 166 | Staphylococcus epidermidis | Environmental lab contaiminant; NY, NY, 16S rRNA sequencing | na | 5.12 |
| 224 | Staphylococcus epidermidis | HER 1292 | 512 | 5.12 |
| 225 | Staphylococcus epidermidis | HPH-6 | 128 | 0.512 |
| 226 | Staphylococcus epidermidis | HPH-5 | 512 | 5.12 |
| 227 | Staphylococcus epidermidis | HCN-4 | >512 | 5.12 |
| 272 | Staphylococcus epidermidis | NRS53 (VISE) | 128 | 0.215 |
| 280 | Staphylococcus epidermidis | NRS101 (MRSE) | 128 | 0.512 |
| 300 | Staphylococcus epidermidis | NRS8, (VISE) | 32 | 0.512 |
| 313 | Staphylococcus epidermidis | NRS34 (VISE) | 8 | 0.512 |
| 533 | Staphylococcus epidermidis | NRS6; (VISE); bloodstream USA | >512 | 0.512 |
| 552 | Staphylococcus epidermidis | ATCC #12228 (MSSE) | na | 51.2 |
| 769 | Staphylococcus epidermidis | NRS101 | 64 | 0.512 |
| 1152 | Staphylococcus epidermidis | ATCC-14990 | na | 5.12 |
| 1154 | Staphylococcus epidermidis | ATCC-49461 | na | 5.12 |
| 1161 | Staphylococcus epidermidis | NRS850-VCU028 | na | 5.12 |

TABLE 7-continued

| CFS | Type | Designation | MIC | BEC |
| --- | --- | --- | --- | --- |
| 1164 | Staphylococcus epidermidis | NRS853-VCU041 | na | 5.12 |
| 1165 | Staphylococcus epidermidis | NRS854-VCU045 | na | 5.12 |
| 1168 | Staphylococcus epidermidis | NRS857-VCU065 | na | 0.512 |
| 1174 | Staphylococcus epidermidis | NRS864-VCU112 | na | 51.2 |
| 1184 | Staphylococcus epidermidis | NRS874-VCU126 | na | 5.12 |
| 1185 | Staphylococcus epidermidis | NRS875-VCU127 | na | 5.12 |
| 1186 | Staphylococcus epidermidis | NRS876-VCU128 | na | 0.512 |

MIC = minimum inhibitory concentration of PlySs2 (in µg/ml) calculated using standard CLSI method for broth microdilution.
na, indicates the data is not available
BEC = Biofilm eradicating concentration of PlySs2 (in µg/ml) is the lowest concentration of a dilution range that completely destroys a 24 hour biofilm of the indicated strains acetic acid in each well, and absorbance ($OD_{600\ nm}$) was read using 200 uL of the solubilized CV. Percent biofilm was determined by dividing the absorbance of the well with the absorbance of the no lysin well (biofilm control). The BEC was determined as the value that showed >75% clearing of the biofilm.

These results demonstrate the potent activity of PlySs2 lysin against *S. epidermidis* biofilms; notably, the potent activity extends to strains with high PlySs2 MIC epidermidis biofilms; notably, the potent activity extends to strains with high PlySs2 MIC levels. These data indicate PlySs2 will be active against a wide range of *S. epidermidis* biofilms.

*S. epidermidis* biofilms in catheters were treated with PlySs2 and evaluated using methods similarly as described above for the *S. aureus* studies. *S. epidermidis* does not produce biofilms on catheters as robustly as the *S. aureus* strains previously described, however biofilm growth did occur and could be evaluated.

Figure 17:
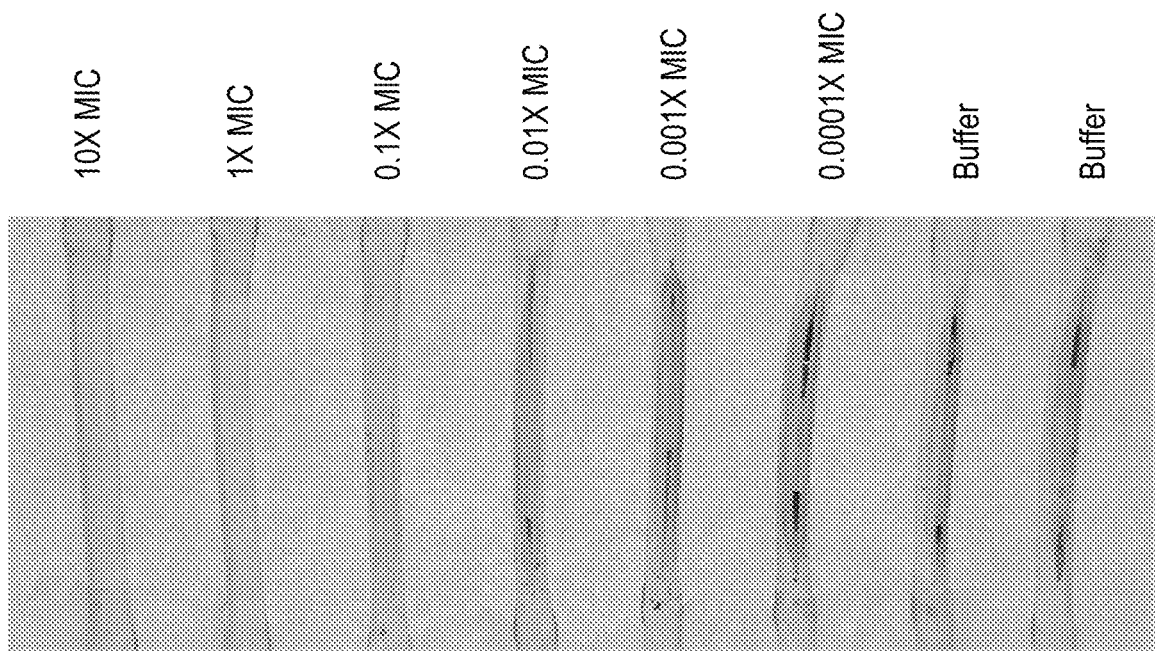
FIG. 17 depicts titration analysis of a catheter study with Staphylococcal *epidermidis* strain CFS 313 (NRS34, a VISE strain) bacterial biofilm. Biofilm staining with methylene blue is shown after 4 hour treatment with buffer or titrated MICs of PlySs2 of 10×MIC, 1×MIC (8 ag/ml), 0.1×MIC, 0.01×MIC, 0.001×MIC and 0.0001×MIC PlySs2.

The results of *S. epidermidis* (strain CFS 313 NRS34, which is a vancomycin intermediate sensitive *S. epidermidis* (VISE) strain) biofilm studies on catheters treated with PlySs2 at 10×MIC and below are shown in FIG. 17. *S. epidermidis* biofilm is destroyed at PlySs2 concentrations down to 0.1×MIC. The MIC here is 8 ug/ml. A similar result and comparable level of activity was observed with *S. aureus* strain CFS 218 (MRSA strain ATCC BAA-42).

Example 12

Figure 18:
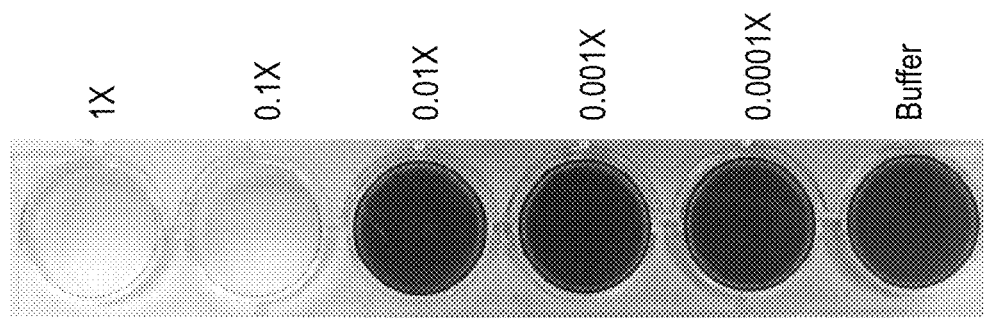
FIG. 18 depicts a biofilm prevention assay of BAA-42 MRSA bacteria inoculated in 24 well plates and combined immediately with buffer or PlySs2 at 1×MIC (32 tag/ml), or dilutions noted to 0.0001×MIC. The plates were incubated for 6 hours, washed with PBS, stained with crystal violet to evaluate biofilm generation and photographed.

The results of a biofilm prevention assay are presented in FIG. 18. *S. aureus* MRSA strain BAA-42 ($5×10^5$ bacteria/ml) was inoculated in 2 ml of TSB+0.2% glucose into each well of a row of a 24 well plate. Lysin PlySs2 was added immediately (at concentrations 1×MIC (32 ug/ml), 0.1× MIC, 0.01×MIC, 0.001× MIC and 0.0001×MIC and then incubated for 6 hours at 37° C. in ambient air. Wells were washed with PBS, stained with Crystal Violet, and photographed to evaluate biofilm development under each of the conditions. Buffer control was also evaluated simultaneously. In this study, the bacteria and lysin PlySs2 (different concentrations) are added at the same time and biofilm formation is allowed to proceed for 6 hours. As demonstrated in FIG. 18, preincubation with 1× and 0.1×MIC PlySs2 can effectively and completely prevent the subsequent formation of biofilm. Thus not only can PlySs2 eradicate mature biofilms, it can prevent de novo biofilm formation as well.

Example 13

Figure 19:
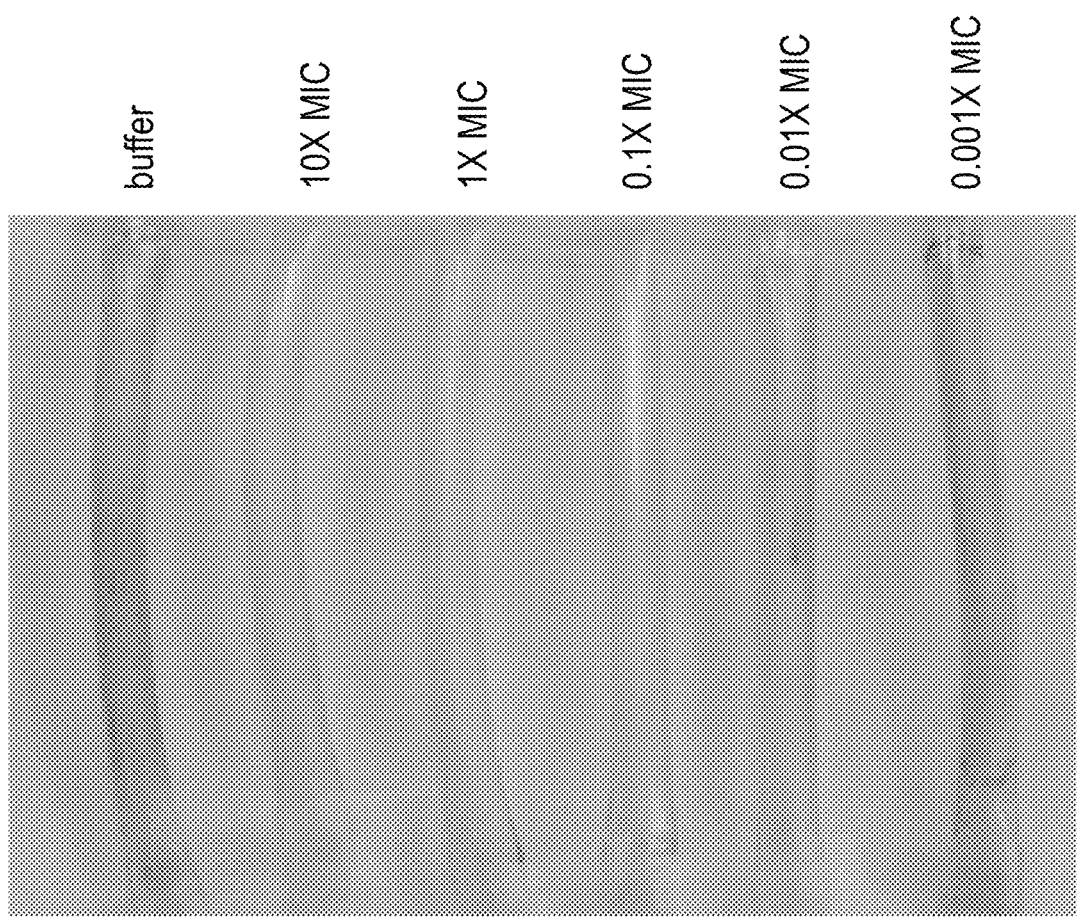
FIG. 19 depicts titration analysis of catheter MRSA strain CFS 553 (ATCC 43300) biofilm staining with methylene blue after 4 hour treatment with buffer or titrated MICs of PlySs2 of 10×MIC, 1×MIC (16 tag/ml), 0.1×MIC, 0.01× MIC and 0.001×MIC PlySs2.
Figure 20:
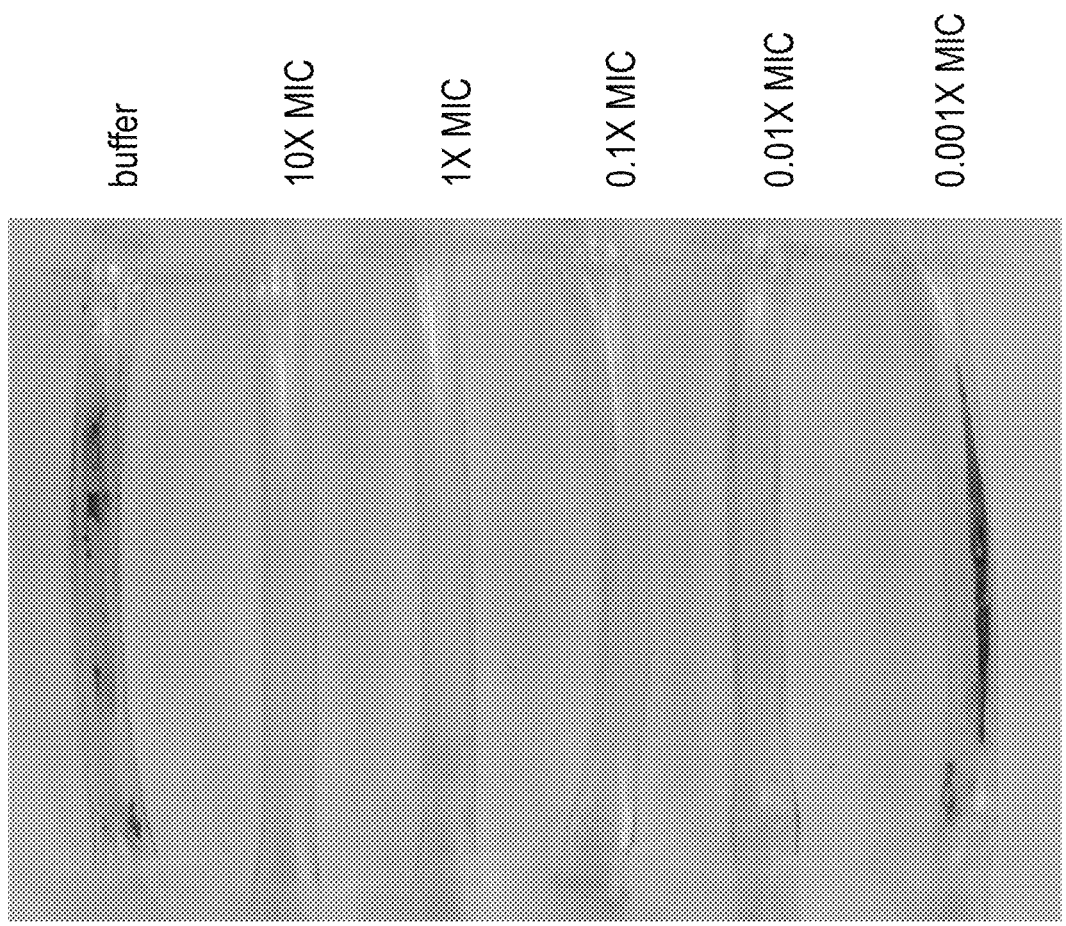
FIG. 20 depicts titration analysis of catheter MRSA strain CFS 992 (JMI 5381) biofilm staining with methylene blue after 4 hour treatment with buffer or titrated MICs of PlySs2 of 10×MIC, 1×MIC (32 tag/ml), 0.1×MIC, 0.01×MIC and 0.001×MIC PlySs2.

In addition to biofilms generated by BAA-42 MRSA as described above, additional *S. aureus* strain biofilms were evaluated for susceptibility to PlySs2 lysin. Each of MRSA strains CFS 553 (ATCC 43300) (FIG. 19) and CFS 992 (JMI 5381) were evaluated in catheter studies using methods as described above. In each instance, 3 day-old biofilms were washed and treated with indicated PlySS2 concentrations for 4 hours. The 1×MIC for strain ATCC 4330 is 16 µg/ml and the 1×MIC for strain JMI 5381 is 32 µg/ml. As shown in FIGS. 19 and 20, these alternative MRSA strain biofilms were susceptible to PlySs2 and Plyss2 eradicated and fully dispersed the catheter biofilm at levels of 10×MIC, 1×MIC, and 0.1×MIC. The biofilms were significantly reduced in each strain using 0.01×MIC PlySs2.

Example 14

Biofilms were generated on catheter tubing (PVC with DEHP as plasticizer) as above and evaluated for PlySs2 sensitivity by scanning electron microscopy (SEM). The three-day-old biofilms of MRSA strain CFS 218 (MRSA strain ATCC BAA-42) on the catheter surface were treated with a 1×MIC concentration (ie, 32 ug/ml) of PlySs2 in Lactated Ringer's Solution for either 30 seconds or 15 minutes before the treatment was washed away and the remaining biofilm was fixed with gluteraldehyde. After fixation on the catheter surface, samples were further processed and analyzed by scanning electron microscopy at 5000× magnification (FIGS. 21A-21C). Treatment with buffer alone (ie, Lactated Ringer's Solution alone) is included as a control. As shown in FIGS. 21A-21C, the PlySs2 treatment rapidly diminishes the MRSA biofilm (within 30 seconds, FIG. 21B) and by 15 minutes FIG. 21C almost completely removes the biofilm.

REFERENCES

1. Klevens, R. M., et al. Invasive Methicillin-Resistant *Staphylococcus aureus* Infections in the United States. *JAMA* 298, 1763-1771 (2007).
2. Brink, A. J. Does resistance in severe infections caused by methicillin-resistant *Staphylococcus aureus* give you the 'creeps'? *Current opinion in critical care* 18, 451-459 (2012).
3. Ben-David, D., Novikov, I. & Mermel, L. A. Are there differences in hospital cost between patients with nosocomial methicillin-resistant *Staphylococcus aureus* bloodstream infection and those with methicillin-susceptible *S. aureus* bloodstream infection? *Infection control and hospital epidemiology: the official journal of the Society of Hospital Epidemiologists of America* 30, 453-460 (2009).
4. Fischetti, V. A. Bacteriophage lysins as effective antibacterials. *Current opinion in microbiology* 11, 393-400 (2008).
5. Fenton, M., Ross, P., McAuliffe, O., O'Mahony, J. & Coffey, A. Recombinant bacteriophage lysins as antibacterials. *Bioengineered Bugs* 1, 9-16 (2010).
6. Nelson, D., Loomis, L. & Fischetti, V. A. Prevention and elimination of upper respiratory colonization of mice by group A streptococci by using a bacteriophage lytic enzyme. *Proceedings of the National Academy of Sciences of the United States of America* 98, 4107-4112 (2001).
7. Witzenrath, M., et al. Systemic use of the endolysin Cpl-1 rescues mice with fatal pneumococcal pneumonia. *Critical care medicine* 37, 642-649 (2009).
8. McCullers, J. A., Karlstrom, A., Iverson, A. R., Loeffler, J. M. & Fischetti, V. A. Novel Strategy to Prevent Otitis Media Cauesed by Colonizing *Streptococcus pneumoniae*. *PLOS pathogens* 3, 0001-0003 (2007).
9. Pastagia, M., et al. A novel chimeric lysin shows superiority to mupirocin for skin decolonization of methicillin-resistant and -sensitive *Staphylococcus aureus* strains. *Antimicrobial agents and chemotherapy* 55, 738-744 (2011).
10. Loeffler, J. M., Djurkovic, S. & Fischetti, V. A. Phage Lytic Enzyme Cpl-1 as a Novel Antimicrobial for Pneumococcal Bacteremia. *Infection and Immunity* 71, 6199-6204 (2003).
11. Entenza, J. M., Loeffler, J. M., Grandgirard, D., Fischetti, V. A. & Moreillon, P. Therapeutic effects of bacteriophage Cpl-1 lysin against *Streptococcus pneumoniae* endocarditis in rats. *Antimicrobial agents and chemotherapy* 49, 4789-4792 (2005).
12. Grandgirard, D., Loeffler, J. M., Fischetti, V. A. & Leib, S. L. Phage lytic enzyme Cpl-1 for antibacterial therapy in experimental pneumococcal meningitis. *The Journal of infectious diseases* 197, 1519-1522 (2008).
13. Blaser, M. Stop killing beneficial bacteria. *Nature* 476, 393-394 (2011).
14. Willing, B. P., Russell, S. L. & Finlay, B. B. Shifting the balance: antibiotic effects on host-microbiota mutualism. *Nature reviews. Microbiology* 9, 233-243 (2011).
15. Gilmer, D. B., Schmitz, J. E., Euler, C. & Fischetti, V. A. Novel Bacteriophage Lysin with Broad Lytic Activity Protects against Mixed Infection by Methicillin-Resistant *Staphylococcus aureus* and *Streptococcus pyogenes* TBD (2012).
16. Schuch, R., Fischetti, V. A. & Nelson, D. C. A Genetic Screen to Identify Bacteriophage Lysins. in *Bacteriophages: Methods and Protocols, Volume 2: Molecular and Applied Aspects, Vol.* 502 307-319 (2009).
17. Bateman, A. & Rawlings, N. D. The CHAP domain: a large family of amidases including GSP amidase and peptidoglycan hydrolases. *Trends Biochem Sci* 28, 234-237 (2003).
18. Whisstock, J. C. & Lesk, A. M. SH3 domains in prokaryotes. *Trends in Biochemical Sciences* 24, 132-133 (1999).
19. Rossi, P., et al. Structural elucidation of the Cys-His-Glu-Asn proteolytic relay in the secreted CHAP domain enzyme from the human pathogen *Staphylococcus saprophyticus*. *Proteins* 74, 515-519 (2009).
20. Mueller, M., de la Pena, A. & Derendorf, H. Issues in Pharmacokinetics and Pharmacodynamics of Anti-Infective Agents: Kill Curves versus MIC. *Antimicrobial agents and chemotherapy* 48, 369-377 (2004).
21. Methods for dilution antimicrobial susceptibility tests for bacteria that grow aerobically. Vol. 32 (Wayne (Pa.): Clinical and Laboratory Standards Institute (US), 2012).
22. Friedman, L., Alder, J. D. & Silverman, J. A. Genetic changes that correlate with reduced susceptibility to daptomycin in *Staphylococcus aureus*. *Antimicrobial agents and chemotherapy* 50, 2137-2145 (2006).
23. Donlan, R. M. & Costerton, J. W. Biofilms: Survival Mechanisms of Clinically Relevant Microorganisms. *Clinical Microbiology Reviews* 15, 167-193 (2002).
24. Cottarel, G. & Wierzbowski, J. Combination drugs, an emerging option for antibacterial therapy. *Trends in biotechnology* 25, 547-555 (2007).
25. Tallarida, R. J. Revisiting the isobole and related quantitative methods for assessing drug synergism. *The Journal of pharmacology and experimental therapeutics* 342, 2-8 (2012).

26. LaPlante, K. L., Leonard, S. N., Andes, D. R., Craig, W. A. & Rybak, M. J. Activities of clindamycin, daptomycin, doxycycline, linezolid, trimethoprim-sulfamethoxazole, and vancomycin against community-associated methicillin-resistant *Staphylococcus aureus* with inducible clindamycin resistance in murine thigh infection and in vitro pharmacodynamic models. *Antimicrobial agents and chemotherapy* 52, 2156-2162 (2008).
27. Crandon, J. L., Kuti, J. L. & Nicolau, D. P. Comparative efficacies of human simulated exposures of telavancin and vancomycin against methicillin-resistant *Staphylococcus aureus* with a range of vancomycin MICs in a murine pneumonia model. *Antimicrobial agents and chemotherapy* 54, 5115-5119 (2010).
28. Abad, C. L., Kumar, A. & Safdar, N. Antimicrobial therapy of sepsis and septic shock—when are two drugs better than one? *Critical care clinics* 27, e1-27 (2011).
29. Fischbach, M. A. Combination therapies for combating antimicrobial resistance. *Current opinion in microbiology* 14, 519-523 (2011).
30. Loeffler, J. M., Nelson, D. & Fischetti, V. A. Rapid killing of *Streptococcus pneumoniae* with a bacteriophage cell wall hydrolase. *Science* 294, 2170-2172 (2001).
31. Costerton, J. W. Bacterial Biofilms: A Common Cause of Persistent Infections. *Science* 284, 1318-1322 (1999).
32. Kiedrowski, M. R. & Horswill, A. R. New approaches for treating staphylococcal biofilm infections. *Annals of the New York Academy of Sciences* 1241, 104-121 (2011).
33. Domenech, M., Garcia, E. & Moscoso, M. In vitro destruction of *Streptococcus pneumoniae* biofilms with bacterial and phage peptidoglycan hydrolases. *Antimicrobial agents and chemotherapy* 55, 4144-4148 (2011).
34. Meng, X., et al. Application of a bacteriophage lysin to disrupt biofilms formed by the animal pathogen *Streptococcus suis*. *Applied and environmental microbiology* 77, 8272-8279 (2011).
35. Schuch, R., Nelson, D. & Fischetti, V. A bacteriolytic agent that detects and kills *Bacillus anthracis*. *Nature* 418, 884-889 (2002).
36. Fischetti, V. A., Nelson, D. & Schuch, R. Reinventing phage therapy: are the parts greater than the sum? *Nature Biotechnology* 24, 1508-1511 (2006).
37. Manoharadas, S., Witte, A. & Blasi, U. Antimicrobial activity of a chimeric enzybiotic towards *Staphylococcus aureus*. *Journal of biotechnology* 139, 118-123 (2009).
38. Rashel, M., et al. Efficient elimination of multidrug-resistant *Staphylococcus aureus* by cloned lysin derived from bacteriophage phi MR11. *The Journal of infectious diseases* 196, 1237-1247 (2007).
39. Daniel, A., et al. Synergism between a novel chimeric lysin and oxacillin protects against infection by methicillin-resistant *Staphylococcus aureus*. *Antimicrobial agents and chemotherapy* 54, 1603-1612 (2010).
40. Kokai-Kun, J. F., Chanturiya, T. & Mond, J. J. Lysostaphin as a treatment for systemic *Staphylococcus aureus* infection in a mouse model. *The Journal of antimicrobial chemotherapy* 60, 1051-1059 (2007).
41. Dhand, A., et al. Use of antistaphylococcal beta-lactams to increase daptomycin activity in eradicating persistent bacteremia due to methicillin-resistant *Staphylococcus aureus*: role of enhanced daptomycin binding. *Clinical infectious diseases: an official publication of the Infectious Diseases Society of America* 53, 158-163 (2011).
42. Matias, V. R. & Beveridge, T. J. Cryo-electron microscopy of cell division in *Staphylococcus aureus* reveals a mid-zone between nascent cross walls. *Molecular microbiology* 64, 195-206 (2007).
43. Kashyap, D. R., et al. Peptidoglycan recognition proteins kill bacteria by activating protein-sensing two-component systems. *Nature medicine* 17, 676-683 (2011).
44. Moise, P. A., North, D., Steenbergen, J. N. & Sakoulas, G. Susceptibility relationship between vancomycin and daptomycin in *Staphylococcus aureus*: facts and assumptions. *Lancet Infect Dis* 9, 617-624 (2009).
45. Jobson, S., Moise, P. A. & Eskandarian, R. Retrospective observational study comparing vancomycin versus daptomycin as initial therapy for *Staphylococcus aureus* infections. *Clinical therapeutics* 33, 1391-1399 (2011).
46. Schweizer, M. L., et al. Comparative effectiveness of nafcillin or cefazolin versus vancomycin in methicillin-susceptible *Staphylococcus aureus* bacteremia. *BMC infectious diseases* 11, 279 (2011).
47. Berti, A. D., et al. Altering the proclivity towards daptomycin resistance in methicillin-resistant *Staphylococcus aureus* using combinations with other antibiotics. *Antimicrobial agents and chemotherapy* 56, 5046-5053 (2012).
48. Sopirala, M. M., et al. Synergy testing by Etest, microdilution checkerboard, and time-kill methods for pan-drug-resistant *Acinetobacter baumannii*. *Antimicrobial agents and chemotherapy* 54, 4678-4683 (2010).
49. Methods for dilution antimicrobial susceptibility tests for bacteria that grow aerobically. Vol. 32 (Clinical and Laboratory Standards Institute (US), Wayne (Pa.), 2012).
50. *Clinical Microbiology Procedures Handbook* 3rd Ed. Washington D.C., (ASM Press, 2010).
51. Pereira, P. M., Filipe, S. R., Tomasz, A. & Pinho, M. G. Fluorescence ratio imaging microscopy shows decreased access of vancomycin to cell wall synthetic sites in vancomycin-resistant *Staphylococcus aureus*. *Antimicrobial agents and chemotherapy* 51, 3627-3633 (2007).
52. Zhang, Y. I-TASSER server for protein 3D structure prediction. *BMC bioinformatics* 9, 40 (2008).
53. Pettersen, E. F., et al. UCSF Chimera—a visualization system for exploratory research and analysis. *Journal of computational chemistry* 25, 1605-1612 (2004).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for disrupting or eradicating a Gram-positive bacterial biofilm comprising *Staphylococcus* and/or *Streptococcus* bacteria, wherein the method comprises:
   contacting the biofilm with a composition comprising a chimeric lysin polypeptide effective to kill *Staphylococcus* and/or *Streptococcus* bacteria in a biofilm,
   wherein the chimeric lysin polypeptide comprises a cysteine, histidine-dependent amidohydrolases/peptidases (CHAP) domain comprising SEQ ID NO: 3 or a variant thereof having at least 90% identity to the polypeptide of SEQ ID NO: 3, and a binding domain, or
   wherein the chimeric lysin polypeptide comprises a Src homology 3 (SH3) domain comprising SEQ ID NO: 4 or a variant thereof having at least 90% identity to the polypeptide of SEQ ID NO: 4 and a catalytic domain, and wherein the biofilm is disrupted or eradicated.

2. The method of claim 1, wherein the chimeric lysin polypeptide comprises the CHAP domain of SEQ ID NO: 3 or a variant thereof having at least 90% identity to the polypeptide of SEQ ID NO: 3.

3. The method of claim 1, wherein the CHAP domain comprises SEQ ID NO: 3.

4. The method of claim 1, wherein the chimeric lysin polypeptide comprises a variant of SEQ ID NO: 1, and wherein the variant comprises a replacement of the CHAP domain.

5. The method of claim 1, wherein the biofilm is on a surface of a tissue.

6. A method for disrupting or eradicating a Gram-positive bacterial biofilm comprising *Staphylococcus* and/or *Streptococcus* bacteria, wherein the method comprises:
   contacting the biofilm with a composition comprising a chimeric lysin polypeptide effective to kill *Staphylococcus* and/or *Streptococcus* bacteria in a biofilm,
   wherein the chimeric lysin polypeptide comprises a SH3 domain of SEQ ID NO: 4 or a variant thereof having at least 90% identity to the polypeptide of SEQ ID NO: 4 and a catalytic domain,
   and wherein the biofilm is disrupted or eradicated.

7. The method of claim 6, wherein the SH3 domain comprises SEQ ID NO: 4.

8. The method of claim 6, wherein the biofilm is on a surface of a medical device.

9. The method of claim 8, wherein the medical device is a catheter, a valve, a prosthetic device, a drug pump, a stent or an orthopedic material.

10. The method of claim 6, wherein the biofilm comprises one or more *Staphylococcus* and/or *Streptococcus* bacteria selected from *Staphylococcus aureus*, *Staphylococcus simulans*, *Streptococcus suis*, *Staphylococcus epidermidis*, *Streptococcus equi*, *Streptococcus equi* zoo, *Streptococcus agalactiae*, *Streptococcus pyogenes*, *Streptococcus sanguinis*, *Streptococcus gordonii*, *Streptococcus dysgalactiae*, Group G *Streptococcus*, Group E *Streptococcus* and *Streptococcus pneumonia*.

11. The method of claim 6, wherein the bacteria in the biofilm comprise antibiotic-resistant bacteria and/or bacteria comprising an altered antibiotic sensitivity.

12. The method of claim 11, wherein the antibiotic-resistant bacteria comprise methicillin-resistant *Staphylococcus aureus* (MRSA), vancomycin resistant *Staphylococcus aureus* (VRSA), daptomycin-resistant *Staphylococcus aureus* (DRSA), and/or linezolid-resistant *Staphylococcus aureus* (LRSA), and the altered antibiotic sensitivity bacteria comprise vancomycin intermediate-sensitivity *Staphylococcus aureus* (VISA).

13. The method of claim 6, wherein the composition further comprises one or more antibiotic(s).

14. The method of claim 8, wherein the method further comprises contacting the surface with one or more antibiotic(s).

15. The method of claim 14, wherein the one or more antibiotic(s) is a glycopeptide, a cephalosporin, a macrolide, a penicillin, or combinations thereof.

16. The method of claim 14, wherein the one or more antibiotic(s) is a penicillin, and wherein the penicillin is oxacillin, ampicillin, cloxacillin, or combinations thereof.

17. The method of claim 14, wherein the one or more antibiotic(s) is a glycopeptide, and wherein the glycopeptide is vancomycin, teicoplanin, or combinations thereof.

18. The method of claim 14, wherein the one or more antibiotic(s) is a macrolide, and wherein the macrolide is erythromycin, clarithromycin, azithromycin, roxithromycin, or combinations thereof.

19. The method of claim 14, wherein the one or more antibiotic(s) is daptomycin, vancomycin, linezolid, or combinations thereof.

20. A method for treating a Gram-positive bacterial biofilm infection comprising *Staphylococcus* and/or *Streptococcus* bacteria in a subject, wherein the method comprises:
    administering to the subject a composition comprising a chimeric lysin polypeptide effective to kill *Staphylococcus* and/or *Streptococcus* bacteria in a biofilm,
    wherein the chimeric lysin polypeptide comprises a CHAP domain comprising SEQ ID NO: 3 or a variant thereof having at least 90% identity to the polypeptide of SEQ ID NO: 3 and a SH3 domain, or
    wherein the chimeric lysin polypeptide comprises an SH3 domain comprising SEQ ID NO: 4 or a variant thereof having at least 90% identity to the polypeptide of SEQ ID NO: 4 and a CHAP domain,
    and wherein the biofilm is disrupted or eradicated.

21. The method of claim 20, wherein the chimeric lysin polypeptide comprises a SH3 domain comprising SEQ ID NO: 4 or a variant thereof having at least 90% identity to the polypeptide of SEQ ID NO: 4 and a CHAP domain.

22. The method of claim 20, wherein the chimeric lysin polypeptide comprises a SH3 domain comprising SEQ ID NO: 4 and a CHAP domain.

23. The method of claim 20, wherein the chimeric lysin polypeptide comprises a CHAP domain comprising SEQ ID NO: 3 or a variant thereof having at least 90% identity to the polypeptide of SEQ ID NO: 3 and a SH3 domain.

24. The method of claim 20, wherein the chimeric lysin polypeptide comprises a CHAP domain comprising SEQ ID NO: 3 and a SH3 domain.

25. The method of claim 20, wherein the biofilm is on a surface of a medical device implanted in the subject.

26. The method of claim 25, wherein the implanted medical device is a catheter, a valve, a prosthetic device, a drug pump, a stent or an orthopedic material.

27. The method of claim 25, wherein the medical device is implanted into the heart or heart vessels of the subject.

28. The method of claim 25, wherein the medical device is a stent.

29. The method of claim 20, wherein the Gram-positive bacterial biofilm infection is endocarditis, osteomyelitis or an infection of a replacement joint.

30. The method of claim 20, wherein the Gram-positive bacterial biofilm infection is endocarditis.

31. The method of claim 20, wherein the Gram-positive bacterial biofilm infection is osteomyelitis.

32. The method of claim 20, wherein the Gram-positive bacterial biofilm infection is an infection of a replacement joint.

33. The method of claim 20, wherein the biofilm comprises one or more *Staphylococcus* and/or *Streptococcus* bacteria selected from *Staphylococcus aureus*, *Staphylococcus simulans*, *Streptococcus suis*, *Staphylococcus epidermidis*, *Streptococcus equi*, *Streptococcus equi* zoo, *Streptococcus agalactiae*, *Streptococcus pyogenes*, *Streptococcus sanguinis*, *Streptococcus gordonii*, *Streptococcus dysgalactiae*, Group G *Streptococcus*, Group E *Streptococcus* and *Streptococcus pneumonia*.

34. The method of claim 20, wherein the *Staphylococcus* and/or *Streptococcus* bacteria comprise antibiotic-resistant bacteria and/or *Staphylococcus* and/or *Streptococcus* bacteria comprising an altered antibiotic sensitivity.

35. The method of claim 34, wherein the antibiotic-resistant *Staphylococcus* and/or *Streptococcus* bacteria comprise methicillin-resistant *Staphylococcus aureus* (MRSA), vancomycin resistant *Staphylococcus aureus* (VRSA), daptomycin-resistant *Staphylococcus aureus* (DRSA), and/or linezolid-resistant *Staphylococcus aureus* (LRSA), and the altered antibiotic sensitivity *Staphylococcus* and/or *Streptococcus* bacteria comprise vancomycin intermediate-sensitivity *Staphylococcus aureus* (VISA).

36. The method of claim 20, wherein the composition further comprises one or more antibiotic(s).

37. The method of claim 20, wherein the method further comprises administering one or more antibiotic(s) to the subject.

38. The method of claim 37, wherein the administrating of the one or more antibiotic(s) is before or simultaneous with, the administering of the composition.

39. The method of claim 37, wherein the one or more antibiotic(s) is a glycopeptide, a macrolide, a penicillin, or combinations thereof.

40. The method of claim 37, wherein the one or more antibiotic(s) is a penicillin, and wherein the penicillin is oxacillin, ampicillin, cloxacillin, or combinations thereof.

41. The method of claim 37, wherein the one or more antibiotic(s) is a glycopeptide, and wherein the glycopeptide is vancomycin, teicoplanin, or combinations thereof.

42. The method of claim 37, wherein the one or more antibiotic(s) is daptomycin, vancomycin, linezolid, or combinations thereof.

43. The method of claim 37, wherein the one or more antibiotic(s) is a macrolide, and wherein the macrolide is erythromycin, clarithromycin, azithromycin, roxithromycin or combinations thereof.

* * * * *

SEQUENCE LISTING

<160> NUMBER OF SEQ ID NOS: 5

<210> SEQ ID NO 1
<211> LENGTH: 245

```
<212> TYPE: PRT
<213> ORGANISM: Streptococcus suis

<400> SEQUENCE: 1

Met Thr Thr Val Asn Glu Ala Leu Asn Asn Val Arg Ala Gln Val Gly
1               5                   10                  15

Ser Gly Val Ser Val Gly Asn Gly Glu Cys Tyr Ala Leu Ala Ser Trp
            20                  25                  30

Tyr Glu Arg Met Ile Ser Pro Asp Ala Thr Val Gly Leu Gly Ala Gly
        35                  40                  45

Val Gly Trp Val Ser Gly Ala Ile Gly Asp Thr Ile Ser Ala Lys Asn
    50                  55                  60

Ile Gly Ser Ser Tyr Asn Trp Gln Ala Asn Gly Trp Thr Val Ser Thr
65                  70                  75                  80

Ser Gly Pro Phe Lys Ala Gly Gln Ile Val Thr Leu Gly Ala Thr Pro
                85                  90                  95

Gly Asn Pro Tyr Gly His Val Val Ile Val Glu Ala Val Asp Gly Asp
            100                 105                 110

Arg Leu Thr Ile Leu Glu Gln Asn Tyr Gly Gly Lys Arg Tyr Pro Val
        115                 120                 125

Arg Asn Tyr Tyr Ser Ala Ala Ser Tyr Arg Gln Gln Val Val His Tyr
    130                 135                 140

Ile Thr Pro Pro Gly Thr Val Ala Gln Ser Ala Pro Asn Leu Ala Gly
145                 150                 155                 160

Ser Arg Ser Tyr Arg Glu Thr Gly Thr Met Thr Val Thr Val Asp Ala
                165                 170                 175

Leu Asn Val Arg Arg Ala Pro Asn Thr Ser Gly Glu Ile Val Ala Val
            180                 185                 190

Tyr Lys Arg Gly Glu Ser Phe Asp Tyr Asp Thr Val Ile Ile Asp Val
        195                 200                 205

Asn Gly Tyr Val Trp Val Ser Tyr Ile Gly Gly Ser Gly Lys Arg Asn
    210                 215                 220

Tyr Val Ala Thr Gly Ala Thr Lys Asp Gly Lys Arg Phe Gly Asn Ala
225                 230                 235                 240

Trp Gly Thr Phe Lys
                245

<210> SEQ ID NO 2
<211> LENGTH: 738
<212> TYPE: DNA
<213> ORGANISM: Streptococcus suis

<400> SEQUENCE: 2
atgacaacag taaatgaagc attaaataat gtaagagctc aggttgggtc cggtgtgtct      60
gttggcaacg gcgaatgcta cgctttggct agttggtacg agcgcatgat tagtccggat     120
gcaactgtcg gacttggcgc tggtgtgggc tgggtcagcg gtgcaatcgg cgatacaatc     180
tctgccaaaa acatcggctc atcatacaac tggcaagcta acggctggac agtttccaca     240
tctggtccat ttaaagcagg tcagattgtg acgcttgggg caacaccagg aaacccttac     300
ggacatgtgg taatcgtcga agcagtggac ggcgatagat tgactatttt ggagcaaaac     360
tacggcggga aacgttatcc cgtccgtaat tattacagcg ctgcaagcta tcgtcaacag     420
gtcgtgcatt acatcacacc gcctggcacg gtcgcacagt cagcacccaa ccttgcaggc     480
tctcgttcct atcgcgagac gggcactatg actgtcacgg tcgatgctct caatgttcgc     540
```

| | | |
|---|---|---|
| agggcgccaa atacttcagg cgagattgta gcagtataca agcgtggtga atcatttgac | | 600 |
| tatgatactg tcatcatcga tgtcaatggc tatgtctggg tgtcttacat aggcggcagc | | 660 |
| ggcaaacgta actacgttgc gacgggcgct accaaagacg gtaagcgttt cggcaatgct | | 720 |
| tggggtacat ttaaataa | | 738 |

```
<210> SEQ ID NO 3
<211> LENGTH: 139
<212> TYPE: PRT
<213> ORGANISM: Streptococcus suis

<400> SEQUENCE: 3

Leu Asn Asn Val Arg Ala Gln Val Gly Ser Gly Val Ser Val Gly Asn
1               5                   10                  15

Gly Glu Cys Tyr Ala Leu Ala Ser Trp Tyr Glu Arg Met Ile Ser Pro
            20                  25                  30

Asp Ala Thr Val Gly Leu Gly Ala Gly Val Gly Trp Val Ser Gly Ala
        35                  40                  45

Ile Gly Asp Thr Ile Ser Ala Lys Asn Ile Gly Ser Ser Tyr Asn Trp
    50                  55                  60

Gln Ala Asn Gly Trp Thr Val Ser Thr Ser Gly Pro Phe Lys Ala Gly
65                  70                  75                  80

Gln Ile Val Thr Leu Gly Ala Thr Pro Gly Asn Pro Tyr Gly His Val
                85                  90                  95

Val Ile Val Glu Ala Val Asp Gly Asp Arg Leu Thr Ile Leu Glu Gln
            100                 105                 110

Asn Tyr Gly Gly Lys Arg Tyr Pro Val Arg Asn Tyr Tyr Ser Ala Ala
        115                 120                 125

Ser Tyr Arg Gln Gln Val Val His Tyr Ile Thr
    130                 135

<210> SEQ ID NO 4
<211> LENGTH: 67
<212> TYPE: PRT
<213> ORGANISM: Streptococcus suis

<400> SEQUENCE: 4

Arg Ser Tyr Arg Glu Thr Gly Thr Met Thr Val Thr Val Asp Ala Leu
1               5                   10                  15

Asn Val Arg Arg Ala Pro Asn Thr Ser Gly Glu Ile Val Ala Val Tyr
            20                  25                  30

Lys Arg Gly Glu Ser Phe Asp Tyr Asp Thr Val Ile Ile Asp Val Asn
        35                  40                  45

Gly Tyr Val Trp Val Ser Tyr Ile Gly Gly Ser Gly Lys Arg Asn Tyr
    50                  55                  60

Val Ala Thr
65

<210> SEQ ID NO 5
<211> LENGTH: 280
<212> TYPE: PRT
<213> ORGANISM: Staphylococcus aureus

<400> SEQUENCE: 5

Met Glu Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30
```

-continued

```
Ala Val Asp Tyr Ile Tyr His Val Thr Asp Gly Lys Ile Arg Met Trp
        35              40                  45
Gly Asn Ala Lys Asp Ala Ile Asn Asn Ser Phe Gly Gly Thr Ala Thr
        50              55                  60
Val Tyr Lys Asn Tyr Pro Ala Phe Arg Pro Lys Tyr Gly Asp Val Val
65              70                  75                      80
Val Trp Thr Thr Gly Asn Phe Ala Thr Tyr Gly His Ile Ala Ile Val
            85                  90                  95
Thr Asn Pro Asp Pro Tyr Gly Asp Leu Gln Tyr Val Thr Val Leu Glu
            100             105             110
Gln Asn Trp Asn Gly Asn Gly Ile Tyr Lys Thr Glu Leu Ala Thr Ile
        115             120             125
Arg Thr His Asp Tyr Thr Gly Ile Thr His Phe Ile Arg Pro Asn Phe
        130             135             140
Ala Thr Glu Ser Ser Val Lys Lys Lys Asp Thr Lys Lys Lys Pro Lys
145                 150             155                 160
Pro Ser Asn Arg Asp Gly Leu Asn Lys Asp Lys Ile Val Tyr Asp Arg
            165             170             175
Thr Asn Ile Asn Tyr Asn Met Val Leu Gln Gly Lys Ser Ala Ser Lys
            180             185             190
Ile Thr Val Gly Ser Lys Ala Pro Tyr Asn Leu Lys Trp Ser Lys Gly
        195             200             205
Ala Tyr Phe Asn Ala Lys Ile Asp Gly Leu Gly Ala Thr Ser Ala Thr
    210             215             220
Arg Tyr Gly Asp Asn Arg Thr Asn Tyr Arg Phe Asp Val Gly Gln Ala
225             230             235                     240
Val Tyr Ala Pro Gly Thr Leu Ile Tyr Val Phe Glu Ile Ile Asp Gly
            245             250             255
Trp Cys Arg Ile Tyr Trp Asn Asn His Asn Glu Trp Ile Trp His Glu
            260             265             270
Arg Leu Ile Val Lys Glu Val Phe
            275             280
```